(12) United States Patent
Pyring et al.

(10) Patent No.: US 7,173,030 B2
(45) Date of Patent: Feb. 6, 2007

(54) INHIBITORS OF 11-β-HYDROXY STEROID DEHYDROGENASE TYPE 1

(75) Inventors: David Pyring, Bromma (SE); Martin Henriksson, Stockholm (SE); Jan Vagberg, Sollentuna (SE); Meredith Williams, Uppsala (SE); Cecilia Nilsson, Solna (SE); Catrine Dreifeldt, Bromma (SE)

(73) Assignee: Biovitrum AB, Stockholm (SE)

( * ) Notice: Subject to any disclaimer, the term of this patent is extended or adjusted under 35 U.S.C. 154(b) by 8 days.

(21) Appl. No.: 10/850,464

(22) Filed: May 21, 2004

(65) Prior Publication Data

US 2005/0009821 A1    Jan. 13, 2005

Related U.S. Application Data

(60) Provisional application No. 60/494,701, filed on Aug. 12, 2003.

(30) Foreign Application Priority Data

| May 21, 2003 | (SE) | ................................. | 0301504 |
| Jun. 25, 2003 | (SE) | ................................. | 0301887 |
| Jun. 25, 2003 | (SE) | ................................. | 0301889 |

(51) Int. Cl.
*A61K 31/535* (2006.01)
*C07D 417/00* (2006.01)
(52) U.S. Cl. .................. 514/236.2; 544/134; 548/125; 548/128; 549/59; 549/68
(58) Field of Classification Search ............... 514/363, 514/236.2; 548/128; 544/134
See application file for complete search history.

(56) References Cited

U.S. PATENT DOCUMENTS 3,332,942 A    7/1967   Breivogel

FOREIGN PATENT DOCUMENTS

| EP | 1 277 729 A1 | 1/2003 |
| GB | 822947 A | 11/1959 |
| GB | 1053085 A | 12/1966 |
| GB | 1240545 A | 7/1971 |
| WO | WO 01/90090 A1 | 11/2001 |
| WO | WO 01/90091 A1 | 11/2001 |
| WO | WO 03/043999 A1 | 5/2003 |
| WO | WO 03/044000 A1 | 5/2003 |

OTHER PUBLICATIONS

U.S. Appl. No. 10/302,329.*
Small et al., Preventing local regeneration of glucocorticoids by 11βHSD1 enhances angiogenesis, PNAS, Aug. 23, 2005, vol. 102, No. 34, pp. 12165-12170, especially p. 12165.*
Walker et al., 11βHSD1 as a novel therapeutic target in metabolic and neurodegenerative disease, Expert Opin. Ther. Targets, Mar. 17, 2004, vol. 7, No. 6, pp. 771-783, especially p. 771.*
Ogg et al., The crystal structure of guinea pig 11βHSD1 provides a model for enzyme-lipid bilayer interactions, Feb. 4, 2005, vol. 280, No. 5, pp. 3789-3794, especially p. 3789.*
Tomlinson et al., 11βHSD1: a tissue specific regulator of glucocorticoid response, Oct. 2004, vol. 25, No. 5, pp. 831-866, especially p. 831; Valsamakis, et al., 11βHSD1 activity in lean and obese males with type-2 diabetes mellitus, J. Clin. Endocrinol. Metab., Sep. 2004, vol. 89, No. 9, pp. 4755-4761, especially p. 4755.*
Merck & Co., Merck Index; Monograph No. 4488 which discloses the antidiabetic compound N-(5-tert-butyl-1,3,4-thiadiazol-2-yl)benzenesulfonamide.*
Stozowska et al., "Urinary silver and sulfathiazole levels in thermally injured guinea pigs during treatment with silver sulfathiazole cream," *S.T.P. Pharma Sciences*, 1995, pp. 452-455, vol. 5.
Anton-Fos et al., "Pharmacological studies of the two new hypoglycemic compounds 4-(3-methyl-5-oxo-2-pyrazolin-1-yl)benzoic acid and 1-(mesitylen-2-sulfonyl)-1H-1,2,4-triazole," STN International, File HCAPLUS, HCAPLUS accession No. 1995:311976, document No. 122:204545, 1994.
Avetisyan, et al., "Synthesis and Hypoglycemic activity of sulfonamide-1,3,4-thiadiazoles," STN International, File HCAPLUS, HCAPLUS accession No. 1981-515404, document No. 95:115404, 1981.
Shoeb et al., "Possible oral hypoglycemic agents. III. Synthesis of some 3-amino-5-phenyl- and 5-amino-3-methyl-1,2,4-thiadiazole derivatives," STN International, File HCAPLUS, HCAPLUS accession No. 1963:441726, document No. 59:41726, 1963.
Kivman et al., "Penetration of sulfanilamides into inflammatory foci," STN International, File HCAPLUS, HCAPLUS accession No. 1982:484681, document No. 97:84681, 1982.
Scozzafava et al., "Carbonic anhydrase inhibitors: topically acting antiglaucoa sulfonamides incorporating phthaloyl and phthalimido moieties," STN International, File HCAPLUS, HCAPLUS accession No. 2001:884365, document No. 136:160861, 2001.
Ingle et al., "Synthesis of 2-sulfanilamidotiazole derivatives and their antibacterial activity," STN International, File HCAPLUS, HCAPLUS accession No. 1979:38829, document No. 90:38829, 1978.

* cited by examiner

*Primary Examiner*—Joseph K. McKane
*Assistant Examiner*—Susannah L. Chung
(74) *Attorney, Agent, or Firm*—Foley & Lardner LLP

(57) ABSTRACT

The present invention relates to compounds with the formula (I)

$$\underset{R^1}{\overset{O\diagdown\diagup O}{\underset{\|}{T-S-N}}}\overset{N-A_1}{\underset{S}{\diagdown\diagup A_2}}$$

and also to pharmaceutical compositions comprising the compounds, as well as to the use of the compounds in medicine and for the preparation of a medicament which acts on the human 11-β-hydroxysteroid dehydrogenase type 1 enzyme.

24 Claims, No Drawings

INHIBITORS OF 11-β-HYDROXY STEROID DEHYDROGENASE TYPE 1

RELATED APPLICATIONS

This application claims priority to Swedish application number 0301504-7, filed on May 21, 2003, Swedish application number 0301889-2, filed on Jun. 25, 2003, U.S. provisional application 60/494,701, filed on Aug. 12, 2003, and Swedish application number 0301887-6, filed on Jun. 25, 2003, the contents of which are incorporated herein by reference.

TECHNICAL FIELD

The present invention relates to novel compounds, to pharmaceutical compositions comprising the compounds, as well as to the use of the compounds in medicine and for the preparation of a medicament which acts on the human 11-β-hydroxysteroid dehydrogenase type 1 enzyme (11βHSD1).

BACKGROUND

1. Glucorticoids, Diabetes and Hepatic Glucose Production

It has been known for more than half a century that glucocorticoids have a central role in diabetes, e.g. the removal of the pituitary or the adrenal gland from a diabetic animal alleviates the most severe symptoms of diabetes and lowers the concentration of glucose in the blood (Long, C. D. and F. D. W. Leukins (1936) J. Exp. Med. 63: 465–490; Houssay, B. A. (1942) Endocrinology 30: 884–892). It is also well established that glucocorticoids enable the effect of glucagon on the liver.

The role of 11βHSD1 as an important regulator of local glucocorticoid effect and thus of hepatic glucose production is well substantiated (see e.g. Jamieson et al. (2000) J. Endocrinol. 165: p. 685–692). The hepatic insulin sensitivity was improved in healthy human volunteers treated with the non-specific 11βHSD1 inhibitor carbenoxolone (Walker, B. R. et al. (1995) J. Clin. Endocrinol. Metab. 80: 3155–3159). Furthermore, the expected mechanism has been established by different experiments with mice and rats. These studies showed that the mRNA levels and activities of two key enzymes in hepatic glucose production were reduced, namely: the rate-limiting enzyme in gluconeogenesis, phosphoenolpyruvate carboxykinase (PEPCK), and glucose-6-phosphatase (G6Pase) catalyzing the last common step of gluconeogenesis and glycogenolysis. Finally, the blood glucose level and hepatic glucose production is reduced in mice having the 11βHSD1 gene knocked-out. Data from this model also confirm that inhibition of 11βHSD1 will not cause hypoglycemia, as predicted since the basal levels of PEPCK and G6Pase are regulated independently of glucocorticoids (Kotelevtsev, Y. et al., (1997) Proc. Natl. Acad. Sci. USA 94: 14924–14929).

Arzneim.-Forsch./Drug Res; 44 (II), No. 7, 821–826, 1994, discloses the hypoglycemic compounds 4-(3-methyl-5-oxo-2-pyrazolin-1-yl)benzoic acid and 1-(mesitylen-2-sulfonyl)-1H-1,2,4-triazole. The structures of these compounds differ considerably from the structure of the compounds of the present invention, in that the latter are thiadiazoles having an (hetero)arylsulfonamido substituent.

Merck & Co, Merck Index; Monograph number 4488 discloses the antidiabetic compound N-(5-tert-butyl-1,3,4-thiadiazol-2-yl)benzenesulfonamide. However, nothing is said about the activity on 11βHSD1.

FR 2,384,498 discloses compounds having a high hypoglycemic effect. Therefore, treatment of hyperglycemia with these compounds may lead to hypoglycemia. Likewise, the phenylsulfonamides according to GB 822,947 possess a hypoglycemic action of a high order and may also lead to hypoglycemia.

2. Possible Reduction of Obesity and Obesity Related Cardiovascular Risk Factors Obesity is an important factor in syndrome X as well as in the majority (>80%) of type 2 diabetic, and omental fat appears to be of central importance. Abdominal obesity is closely associated with glucose intolerance, hyperinsulinemia, hypertriglyceridemia, and other factors of the so-called syndrome X (e.g. raised blood pressure, decreased levels of HDL and increased levels of VLDL) (Montague & O'Rahilly, Diabetes 49: 883–888, 2000). Inhibition of the enzyme in pre-adipocytes (stromal cells) has been shown to decrease the rate of differentiation into adipocytes. This is predicted to result in diminished expansion (possibly reduction) of the omental fat depot, i.e. reduced central obesity (Bujalska, I. J., S. Kumar, and P. M. Stewart (1997) Lancet 349: 1210–1213).

Inhibition of 11βHSD1 in mature adipocytes is expected to attenuate secretion of the plasminogen activator inhibitor 1 (PAI-1)—an independent cardiovascular risk factor (Halleux, C. M. et al. (1999) J. Clin. Endocrinol. Metab. 84: 4097–4105). Furthermore, there is a clear correlation between glucocorticoid "activity" and cardiovascular risk factore suggesting that a reduction of the glucocorticoid effects would be beneficial (Walker, B. R. et al. (1998) Hypertension 31: 891–895; Fraser, R. et al. (1999) Hypertension 33: 1364–1368).

Adrenalectomy attenuates the effect of fasting to increase both food intake and hypothalamic neuropeptide Y expression. This supports the role of glucocorticoids in promoting food intake and suggests that inhibition of 11βHSD1 in the brain might increase satiety and therefore reduce food intake (Woods, S. C. et al. (1998) Science, 280: 1378–1383).

3. Possible Beneficial Effect on the Pancreas

Inhibition of 11βHSD1 in isolated murine pancreatic β-cells improves the glucose-stimulated insulin secretion (Davani, B. et al. (2000) J. Biol. Chem. 2000 Nov. 10; 275(45): 34841–4). Glucocorticoids were previously known to reduce pancreatic insulin release in vivo (Billaudel, B. and B. C. J. Sutter (1979) Horm. Metab. Res. 11: 555–560). Thus, inhibition of 11βHSD1 is predicted to yield other beneficial effects for diabetes treatment, besides effects on liver and fat.

4. Possible Beneficial Effects on Cognition and Dementia

Stress and glucocorticoids influence cognitive function (de Quervain, D. J.-F., B. Roozendaal, and J. L. McGaugh (1998) Nature 394: 787–790). The enzyme 11βHSD1 controls the level of glucocorticoid action in the brain and thus contributes to neurotoxicity (Rajan, V., C. R. W. Edwards, and J. R. Seckl, J. (1996) Neuroscience 16: 65–70; Seckl, J. R., Front. (2000) Neuroendocrinol. 18: 49–99). Unpublished results indicate significant memory improvement in rats treated with a non-specific 11βHSD1 inhibitor (J. Seckl, personal communication). Based the above and on the known effects of glucocorticoids in the brain, it may also be suggested that inhibiting 11βHSD1 in the brain may result in reduced anxiety (Tronche, F. et al. (1999) Nature Genetics 23: 99–103). Thus, taken together, the hypothesis is that inhibition of 11βHSD1 in the human brain would prevent reactivation of cortisone into cortisol and protect against deleterious glucocorticoid-mediated effects on neuronal survival and other aspects of neuronal function, including cognitive impairment, depression, and increased appetite (previous section).

WO 98/27081 and WO 99/02502 disclose 5HT$_6$ receptor antagonists for the treatment of CNS disorders. None of these compounds fall within formula (I) according to the present invention. Furthermore, nothing is said about the activity on 11βHSD1.

5. Possible Use of Immuno-modulation Using 11βHSD1 Inhibitors

The general perception is that glucocorticoids suppress the immune system. But in fact there is a dynamic interaction between the immune system and the HPA (hypothalamo-pituitary-adrenal) axis (Rook, G. A. W. (1999) Baillièr's Clin. Endocrinol. Metab. 13: 576–581). The balance between the cell-mediated response and humoral responses is modulated by glucocorticoids. A high glucocorticoid activity, such as at a state of stress, is associated with a humoral response. Thus, inhibition of the enzyme 11βHSD1 has been suggested as a means of shifting the response towards a cell-based reaction.

In certain disease states, including tuberculosis, lepra and psoriasis the immune reaction is normaly biased towards a humoral response when in fact the appropriate response would be cell based. Temporal inhibition of 11βHSD1, local or systemic, might be used to push the immune system into the appropriate response (Mason, D. (1991) Immunology Today 12: 57–60; Rook et al., supra).

An analogous use of 11βHSD1 inhibition, in this case temporal, would be to booster the immune response in association with immunization to ensure that a cell based response would be obtained, when desired.

6. Reduction of Intraocular Pressure

Glucocorticoids have been shown to increase intraocular pressure in susceptible individuals and increasing the risk for developing glaucoma (Lewis et al (1988) Am J Ophthalmol 106:607–612). Local effects of glucocorticoids are influenced by levels of glucocorticoid target receptors and 11βHSD enzymes. Inhibition of 11βHSD with the non-specific inhibitor carbenoxolone, was recently presented as a novel approach to lower the intraocular pressure (Raus, S et al *Expression and Putative Role of 11β-Hydroxysteroid Dehydrogenase Isozymes within the Human Eye*, Invest. Opthamol Vis Sci, 2001, 42, 2037–2042). Treatment with carbenoxolone reduced the intraocular pressure by 20% in normal subjects. In the eye, expression of 11βHSD1 is, according to Raus et al, confined to basal cells of the corneal epithelium and the non-pigmented epithelialium of the cornea (the site of aqueous production), to ciliary muscle and to the sphincter and dilator muscles of the iris. In contrast, the distant isoenzyme 11βHSD2 is highly expressed in the non-pigmented ciliary epithelium and corneal endothelium. According to this study, none of the enzymes is found at the trabecular meshwork, the site of drainage. They suggest 11βHSD1 to play a role in aqueous production, rather than drainage. Another investigation (Stokes, J. et al, *Distribution of Glucocorticoid and Mineralocorticoid Receptors and 11b-Hydroxysteroid Dehydrogenases in Human and Rat Ocular Tissues*, Invest. Opthamol Vis Sci, 2000, 41(7) 1629–1638) found a different distribution of 11βHSD1 mRNA in the human eye. They found the enzyme to be predominantly expressed in the trabecular meshwork, the nonpigmented ciliary epitelium and the lens epitelium. The latter finding indicates that 11βHSD1 can be involved both in aqueous production and drainage. The effect on drainage might be via regulation of myocilin, a protein believed to be one of the causing factors for increased intraocular pressure (Stone E M, et al, *Identification of a gene that causes primary open angle glaucoma*. Science 1997 Jan. 31; 275 (5300): 668–70).

7. Reduced Osteoporosis

Glucocorticoids have an essential role in skeletal development and function but are detrimental in excess. Glucocorticoid-induced bone loss is derived, at least in part, via inhibition of bone formation, which includes suppression of osteoblast proliferation and collagen synthesis (Kim, C. H., S. L. Cheng, and G. S. Kim (1999) J. Endocrinol. 162: 371–379). The negative effect on bone nodule formation could be blocked by the non-specific inhibitor carbenoxolone suggesting an important role of 11βHSD1 in the glucocorticoid effect (Bellows, C. G., A. Ciaccia, and J. N. M. Heersche, (1998) Bone 23: 119–125). Other data suggest a role of 11βHSD1 in providing sufficiently high levels of active glucocorticoid in osteoclasts, and thus in augmenting bone resorption (Cooper, M. S. et al. (2000) Bone 27: 375–381). Taken together, these different data suggest that inhibition of 11βHSD1 may have beneficial effects against osteoporosis by more than one mechanism working in parallel.

8. Reduction of Hypertension

Bile acids inhibit 11β-hydroxysteroid dehydrogenase type 2. This results in a shift in the overall body balance in favour of cortisol over cortisone, as shown by studying the ratio of the urinary metabolites (Quattropani C, Vogt B, Odermatt A, Dick B, Frey B M, Frey F J. 2001. J Clin Invest. Nov; 108(9):1299–305. "Reduced activity of 11beta-hydroxysteroid dehydrogenase in patients with cholestasis".). Reducing the activity of 11βHSD1 in the liver by a selective inhibitor is predicted to reverse this imbalance, and acutely counter the symptoms such as hypertension, while awaiting surgical treatment removing the biliary obstruction.

WO 99/65884 discloses carbon substituted aminothiazole inhibitors of cyclin dependent kinases. These compounds may e.g. be used against cancer, inflammation and arthritis. U.S. Pat. No. 5,856,347 discloses an antibacterial preparation or bactericide comprising 2-aminothiazole derivative and/or salt thereof. Further, U.S. Pat. No. 5,403,857 discloses benzenesulfonamide derivatives having 5-lipoxygenase inhibitory activity. Additionally, tetrahydrothiazolo[5,4-c]pyridines are disclosed in: Analgesic tetrahydrothiazolo [5,4-c]pyridines. Fr. Addn. (1969), 18 pp, Addn. to Fr. 1498465. CODEN: FAXXA3; FR 94123 19690704 CAN 72:100685 AN 1970:100685 CAPLUS and 4,5,6,7-Tetrahydrothiazolo[5,4-c]pyridines. Neth. Appl. (1967), 39 pp. CODEN: NAXXAN NL 6610324 19670124 CAN 68:49593, AN 1968: 49593 CAPLUS. However, none of the above disclosures discloses the compounds according to the present invention, or their use for the treatment of diabetes, obesity, glaucoma, osteoporosis, cognitive disorders, immune disorders, depression, and hypertension.

WO 98/16520 discloses compounds inhibiting matrix metalloproteinases (MMPs) and TNF-α converting enzyme (TACE). EP 0 749 964 A1 and U.S. Pat. No. 5,962,490 disclose compounds having an endothelin receptor antagonist activity. None of these compounds fall within formula (I) according to the present invention. Furthermore, nothing is said about the activity on 11βHSD1.

U.S. Pat. No. 5,783,697 discloses thiophene derivatives as inhibitors of PGE2 and LTB4. Nothing is said about the activity on 11βHSD1.

9. Wound Healing

Cortisol performs a broad range of metabolic functions and other functions. The multitude of glucocorticoid action is exemplified in patients with prolonged increase in plasma glucocorticoids, so called "Cushing's syndrome". Patients with Cushing's syndrome have prolonged increase in plasma glucocorticoids and exhibit impaired glucose tolerance, type 2 diabetes, central obesity, and osteoporosis. These patients also have impaired wound healing and brittle skin (Ganong, W. F. Review of Medical Physiology. Eighteenth edition ed. Stamford, Conn.: Appleton & Lange; 1997).

Glucocorticoids have been shown to increase risk of infection and delay healing of open wounds (Anstead, G. M. Steroids, retinoids, and wound healing. Adv Wound Care 1998; 11(6):277–85). Patients treated with glucocorticoids have 2–5-fold increased risk of complications when undergoing surgery (Diethelm, A. G. Surgical management of complications of steroid therapy. Ann Surg 1977; 185(3): 251–63).

The European patent application No. EP 0902288 discloses a method for diagnosing the status of wound healing in a patient, comprising detecting cortisol levels in said wound. The authors suggest that elevated levels of cortisol in wound fluid, relative to normal plasma levels in healthy individuals, correlates with large, non-healing wounds (Hutchinson, T. C., Swaniker, H. P., Wound diagnosis by quantitating cortisol in wound fluids. European patent application No. EP 0 902 288, published Mar. 17, 1999).

In humans, the 11β-HSD catalyzes the conversion of cortisol to cortisone, and vice versa. The parallel function of 11β-HSD in rodents is the interconversion of corticosterone and 11-dehydrocorticosterone (Frey, F. J., Escher, G., Frey, B. M. Pharmacology of 11 beta-hydroxysteroid dehydrogenase. Steroids 1994; 59(2):74–9). Two isoenzymes of 11β-HSD, 11β-HSD1 and 11β-HSD2, have been characterized, and differ from each other in function and tissue distribution (Albiston, A. L., Obeyesekere, V. R., Smith, R. E., Krozowski, Z. S. Cloning and tissue distribution of the human 11 beta-hydroxysteroid dehydrogenase type 2 enzyme. Mol Cell Endocrinol 1994; 105(2):R11–7). Like GR, 11β-HSD1 is expressed in numerous tissues like liver, adipose tissue, adrenal cortex, gonads, lung, pituitary, brain, eye etc (Monder C, White P C. 11 beta-hydroxysteroid dehydrogenase. Vitam Horm 1993; 47:187–271; Stewart, P. M., Krozowski, Z. S. 11 beta-Hydroxysteroid dehydrogenase. Vitam Horm 1999; 57:249–324; Stokes, J., Noble, J., Brett, L., Phillips, C., Seckl, J. R., O'Brien, C., et al. Distribution of glucocorticoid and mineralocorticoid receptors and 11beta-hydroxysteroid dehydrogenases in human and rat ocular tissues. Invest Ophthalmol Vis Sci 2000; 41(7):1629–38). The function of 11βHSD1 is to fine-tune local glucocorticoid action. 11β-HSD activity has been shown in the skin of humans and rodents, in human fibroblasts and in rat skin pouch tissue (Hammami, M. M., Siiteri, P. K. Regulation of 11 beta-hydroxysteroid dehydrogenase activity in human skin fibroblasts: enzymatic modulation of glucocorticoid action. J Clin Endocrinol Metab 1991; 73(2):326–34); Cooper, M. S., Moore, J., Filer, A., Buckley, C. D., Hewison, M., Stewart, P. M. 11beta-hydroxysteroid dehydrogenase in human fibroblasts: expression and regulation depends on tissue of origin. ENDO 2003 Abstracts 2003; Teelucksingh, S., Mackie, A. D., Burt, D., McIntyre, M. A., Brett, L., Edwards, C. R. Potentiation of hydrocortisone activity in skin by glycyrrhetinic acid. Lancet 1990; 335(8697):1060–3; Slight, S. H., Chilakamarri, V. K., Nasr, S., Dhalla, A. K., Ramires, F. J., Sun, Y., et al. Inhibition of tissue repair by spironolactone: role of mineralocorticoids in fibrous tissue formation. Mol Cell Biochem 1998; 189(1–2): 47–54).

Wound healing consists of serial events including inflammation, fibroblast proliferation, secretion of ground substances, collagen production, angiogenesis, wound contraction and epithelialization. It can be divided in three phases; inflammatory, proliferative and remodeling phase (reviewed in Anstead et al., supra).

In surgical patients, treatment with glucocorticoids increases risk of wound infection and delay healing of open wounds. It has been shown in animal models that restraint stress slows down cutaneous wound healing and increases susceptibility to bacterial infection during wound healing. These effects were reversed by treatment with the glucocorticoid receptor antagonist RU486 (Mercado, A. M., Quan, N., Padgett, D. A., Sheridan, J. F., Marucha, P. T. Restraint stress alters the expression of interleukin-1 and keratinocyte growth factor at the wound site: an in situ hybridization study. J Neuroimmunol 2002; 129(1–2):74–83; Rojas, I. G., Padgett, D. A., Sheridan, J. F., Marucha, P. T. Stress-induced susceptibility to bacterial infection during cutaneous wound healing. Brain Behav Immun 2002; 16(1):74–84). Glucocorticoids produce these effects by suppressing inflammation, decrease wound strength, inhibit wound contracture and delay epithelialization (Anstead et al., supra). Glucocorticoids influence wound healing by interfering with production or action of cytokines and growth factors like IGF, TGF-β, EGF, KGF and PDGF (Beer, H. D., Fassler, R., Werner, S. Glucocorticoid-regulated gene expression during cutaneous wound repair. Vitam Horm 2000; 59:217–39; Hamon, G. A., Hunt, T. K., Spencer, E. M. In vivo effects of systemic insulin-like growth factor-I alone and complexed with insulin-like growth factor binding protein-3 on corticosteroid suppressed wounds. Growth Regul 1993; 3(1): 53–6; Laato, M., Heino, J., Kahari, V. M., Niinikoski, J., Gerdin, B. Epidermal growth factor (EGF) prevents methylprednisolone-induced inhibition of wound healing. J Surg Res 1989; 47(4):354–9; Pierce, G. F., Mustoe, T. A., Lingelbach, J., Masakowski, V. R., Gramates, P., Deuel, T. F. Transforming growth factor beta reverses the glucocorticoid-induced wound-healing deficit in rats: possible regulation in macrophages by platelet-derived growth factor. Proc Natl Acad Sci USA 1989; 86(7):2229–33). It has also been shown that glucocorticoids decrease collagen synthesis in rat and mouse skin in vivo and in rat and human fibroblasts (Oishi, Y., Fu, Z. W., Ohnuki, Y., Kato, H., Noguchi, T. Molecular basis of the alteration in skin collagen metabolism in response to in vivo dexamethasone treatment: effects on the synthesis of collagen type I and III, collagenase, and tissue inhibitors of metalloproteinases. Br J Dermatol 2002; 147(5):859–68).

WO 03/044000 discloses other compounds than the compounds of the formula (I) as defined hereinafter, which compounds inhibit the human 11β-HSD1, and may be useful for treating disorders such as diabetes, obesity, glaucoma, osteoporosis, cognitive disorders and immune disorders. Other 11β-HSD1 inhibitors are disclosed in e.g. WO 01/90090; WO 01/90091; WO 01/90092; WO 01/90093; WO 01/90094; WO 03/044009; and WO 03/043999. However, the use of 11β-HSD1 inhibitors for wound healing has not previously been disclosed. Consequently, there is a need of new compounds that are useful in the treatment of diabetes, obesity, glaucoma, osteoporosis, cognitive disorders, immune disorders, depression, hypertension, and wound healing.

SUMMARY OF THE INVENTION

The compounds according to the present invention solves the above problems and embraces a novel class of compounds which has been developed and which inhibit the human 11-β-hydroxysteroid dehydrogenase type 1 enzyme (11-β-HSD$_1$), and may therefore be of use in the treating disorders such as diabetes, obesity, glaucoma, osteoporosis, cognitive disorders, immune disorders, hypertension, and wound healing.

One object of the present invention is a compound of formula (I)

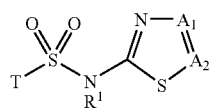

I wherein

T is selected from 2-acetylamino-4-methylthiazol-5-yl; benzyl; 5-bromo-6-chloropyridin-3-yl; 5-chloro-1,3-dimethyl-1H-pyrazol-4-yl; 2,3-dihydro-1,4-benzodioxin-6-yl; 2,3-dihydro-1-benzofuran-5-yl; 5-(dimethylamino)-1-naphthyl; 1,2-dimethyl-1H-imidazol-4-yl; 3,5-dimethylisoxazol-4-yl; 4-methyl-3,4-dihydro-2H-1,4-benzoxazin-7-yl; 1-methyl-1H-imidazol-4-yl; 5-methyl-2-(trifluoromethyl)-3-furyl; 4-morpholin-4-ylpyridin-3-yl; 1-naphthyl; 2-naphthyl; 2,2,4,6,7-pentamethyl-2,3-dihydro-1-benzofuran-5-yl; 6-phenoxypyridin-3-yl; quinolin-8-yl; 1,3,5-trimethyl-1H-pyrazol-4-yl;

thienyl optionally substituted with one or more of acetylamino; chloro; methyl; 2-(methylthio)pyrimidin-4-yl; nitro; phenylsulfonyl; pyridinyl;

phenyl optionally substituted with one or more of acetyl; acetylamino; amino; 4-(1,3-benzothiazol-2-ylthio)acetylamino; benzoylamino; bromo; chloro; 3-chloro-2-cyanophenoxy; (5-chloro-2-hydroxybenzyl)amino; 4-chloro-3-nitrophenylcarbonylamino; [(4-chlorophenyl)amino]carbonylamino; cyano; 2,4-dichlorophenoxyacetylamino; fluoro; 4-{[(4-fluorophenyl)amino]carbonothioyl}amino; 4-fluorophenylcarbonylamino; hydroxy; methoxy; methyl; 5-methyl-1,3,4-oxadiazol-2-yl; (4-methylphthalazin-1-yl)amino; 1,3-oxazol-5-yl; 2-methyl-4-pyrimidyl; n-butoxy; nitro; N-phthalimido; phenoxy; phenyl; 1H-pyrazol-1-yl; tert-butyl; tetrazolyl; 2,2,2-trifluoroethoxy; trifluoromethoxy; trifluoromethyl;

R$^1$ is hydrogen or methyl;

A$_1$ and A$_2$ are a nitrogen atom or C—Z, provided that A$_1$ and A$_2$ have different meanings, wherein:

Z is [(1,3-benzodioxol-5-ylaminocarbonyl)methyl]thio; n-butylthio; (R)-2-[(3-chloro-2-methylbenzenesulfonyl)oxy]propyl; cyclohexyl; cyclopropyl; ethoxycarbonylmethylthio; ethylthio; (R)-2-[(3-fluorophenyl)thio]propyl; 3-furyl; methoxy; 2-methylpyridin-3-yl; morpholin-4-yl; (R)-1-phenoxy-n-propyl; phenyl; (R)-1-phenyl-n-propyl; tert-butyl; tert-butylphenyl; 2-thienyl; 3-thienyl; (trichloromethyl); (trifluoromethyl); A$_3$; or is —CH(CH$_3$)A$_3$, wherein A$_3$ is selected from methyl; carbamoyl; N-(n-butanamidyl); phenylsulfonyl; phenyl; phenoxy optionally substituted with one or more fluoro; phenylthio optionally substituted with one or more acetylamino, methoxy, trifluoromethyl, fluoro; pyridin-3-yloxy; 4-methylpyrimidin-2-ylthio; pyridin-4-ylthio; 1-methyl-1H-imidazol-2-ylthio; or X—Y—R$^2$, wherein X is CH$_2$ or CO;

Y is CH$_2$, CO or a single bond;

R$^2$ is selected from 4-acetylaminophenylsulfonyl; 1-(3-chloro-2-methylphenylsulfonyloxyl)ethyl; 1-[(3-fluorophenyl)thio]ethyl; 4-chlorophenyl; 3-ethoxy-n-propyl; hydrogen; isopropyl; 4-methoxyphenyl; methyl; phenylsulfonyl; pyridin-3-yl; tert-butyl;

NR$^3$R$^4$, wherein R$^3$ and R$^4$ are each independently selected from 3-ethoxy-n-propyl; ethyl; hydrogen; methyl;

NR$^3$R$^4$ represent together 3-carbethoxypiperidin-1-yl; 4-carbethoxypiperidin-1-yl; 3-hydroxymethylpiperidin-1-yl; 3-hydroxypiperidin-1-yl; 4-methylpiperazin-1-yl; morpholin-4-yl; 3-oxopiperazin-1-yl;

R$^5$O, wherein R$^5$ is 2-allylphenyl; 4-chlorophenyl; ethyl; 2-fluorophenyl; 4-fluorophenyl; hydrogen; methyl; 4-nitrophenyl;

R$^6$S, wherein R$^6$ is 2-acetylaminophenyl; 3-acetylaminophenyl; 4-acetylaminophenyl; benzyl; 2,4-difluorophenyl; 3,4-difluorophenyl; 3,4-dimethoxyphenyl; 4-fluorobenzyl; 3-fluorophenyl; 2-methoxyphenyl; 3-methoxyphenyl; 1-methyl-1H-imidazol-2-yl; 2-(4-methylphenoxy)ethyl; 4-methylpyrimidin-2-yl; phenyl; pyridin-2-yl; pyridin-4-yl; pharmaceutically acceptable salts, solvates, hydrates, geometrical isomers, tautomers, optical isomers, N-oxides and prodrug forms thereof;

with the proviso that T is not selected from 4-acetylaminophenyl, 4-aminophenyl, 4-(4-chloro-3-nitrophenylcarbonylamino)phenyl, 4-{[(4-chlorophenyl)amino]carbonylamino}-phenyl, 4-(2,4-dichlorophenoxyacetylamino)phenyl, 4-({[(4-fluorophenyl)amino]-carbonothioyl}amino)phenyl, 4-methoxyphenyl, phenyl, 4-(N-phthalimido)phenyl, and 3-(trifluoromethyl)phenyl; and with the proviso that when R$^1$ is hydrogen and A$_1$ is a nitrogen atom and A$_2$ is C—Z and T is benzyl, then Z is not 2,2-dimethyl-n-propyl, methoxymethyl, isopropyl, tert-butyl, cyclohexyl, isobutyl, 4-methoxybenzyl, trifluoromethyl, and methyl;

A$_1$ is a nitrogen atom and A$_2$ is C—Z, X is CH$_2$, Y is a single bond, R$^2$ is hydrogen, then T is not 2-nitrophenyl;

A$_1$ is a nitrogen atom and A$_2$ is C—Z, X is CH$_2$, Y is a single bond, R$^2$ is hydrogen, then T is not 4-tert-butylphenyl;

A$_1$ is a nitrogen atom and A$_2$ is C—Z, X is CH$_2$, Y is CH$_2$, R$^2$ is hydrogen, then T is not 4-benzoylaminophenyl;

A$_1$ is a nitrogen atom and A$_2$ is C—Z, X is CH$_2$, Y is a single bond, R$^2$ is methyl, then T is not 4-benzoylaminophenyl;

A$_1$ is C—Z and A$_2$ is a nitrogen atom, Z is phenyl, then T is not 3-chloro-2-methylphenyl;

A$_1$ is C—Z and A$_2$ is a nitrogen atom, X is CH$_2$, Y is CH$_2$, R$^2$ is NR$^3$R$^4$, R$^3$ and R$^4$ are both ethyl, then T is not 3-chloro-2-methylphenyl;

A$_1$ is C—Z and A$_2$ is a nitrogen atom, X is CH$_2$, Y is CH$_2$, R$^2$ is NR$^3$R$^4$, R$^3$ and R$^4$ represent together morpholin-4-yl, then T is not 3-chloro-2-methylphenyl;

A$_1$ is C—Z and A$_2$ is a nitrogen atom, X is CH$_2$, Y is CH$_2$, R$^2$ is R$^5$O, R$^5$ is hydrogen, then T is not 3-chloro-2-methylphenyl;

A$_1$ is C—Z and A$_2$ is a nitrogen atom, X is CH$_2$, Y is CH$_2$, R$^2$ is R$^5$O, R$^5$ is methyl, then T is not 3-chloro-2-methylphenyl;

A$_1$ is C—Z and A$_2$ is a nitrogen atom, X is CH$_2$, Y is CH$_2$, R$^2$ is R$^5$O, R$^5$ is ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is methyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 3-chloro-2-methylphenyl;

$A^1$ is C—Z and $A_2$ is a nitrogen atom, X is $CH_2$, Y is CO, $R^2$ is $R^5O$, $R^5$ is hydrogen, then T is not 3-chloro-2-methylphenyl;

$A_1$ is C—Z and $A_2$ is a nitrogen atom, X is $CH_2$, Y is CO, $R^2$ is $R^5O$, $R^5$ is methyl, then T is not 3-chloro-2-methylphenyl;

$A_1$ is C—Z and $A_2$ is a nitrogen atom, X is $CH_2$, Y is CO, $R^2$ is $R^5O$, $R^5$ is ethyl, then T is not 3-chloro-2-methylphenyl;

$A_1$ is C—Z and $A_2$ is a nitrogen atom, X is $CH_2$, Y is a single bond, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is CO, Y is CO, $R^2$ is $R^5O$, $R^5$ is ethyl, then T is not 3-chloro-2-methylphenyl;

$A_1$ is a nitrogen atom and $A_2$ is C—Z, Z is phenyl, then T is not 3-chloro-2-methylphenyl;

$A_1$ is a nitrogen atom and $A_2$ is C—Z, X is $CH_2$, Y is $CH_2$, $R^2$ is $NR^3R^4$, $R^3$ and $R^4$ are both ethyl, then T is not 3-chloro-2-methylphenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 3-chloro-2-methylphenyl;

$A_1$ is a nitrogen atom and $A_2$ is C—Z, X is $CH_2$, Y is $CH_2$, $R^2$ is $R^5O$, $R^5$ is hydrogen, then T is not 3-chloro-2-methylphenyl;

$A_1$ is a nitrogen atom and $A_2$ is C—Z, X is $CH_2$, Y is $CH_2$, $R^2$ is $R^5O$, $R^5$ is methyl, then T is not 3-chloro-2-methylphenyl;

$A_1$ is a nitrogen atom and $A_2$ is C—Z, X is $CH_2$, Y is $CH_2$, $R^2$ is $R^5O$, $R^5$ is ethyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ are hydrogen, then T is not 3-chloro-2-methylphenyl;

$A_1$ is a nitrogen atom and $A_2$ is C—Z, X is $CH_2$, Y is CO, $R^2$ is $NR^3R^4$, $R^3$ is methyl and $R^4$ is hydrogen, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ are methyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ is ethyl and $R^4$ is hydrogen, then T is not 3-chloro-2-methylphenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 3-chloro-2-methylphenyl;

$A_1$ is a nitrogen atom and $A_2$ is C—Z, X is $CH_2$, Y is CO, $R^2$ is $R^5O$, $R^5$ is hydrogen, then T is not 3-chloro-2-methylphenyl;

$A_1$ is a nitrogen atom and $A_2$ is C—Z, X is $CH_2$, Y is CO, $R^2$ is $R^5O$, $R^5$ is methyl, then T is not 3-chloro-2-methylphenyl;

$A_1$ is a nitrogen atom and $A_2$ is C—Z, X is $CH_2$, Y is CO, $R^2$ is $R^5O$, $R^5$ is ethyl, then T is not 3-chloro-2-methylphenyl;

$A_1$ is a nitrogen atom and $A_2$ is C—Z, X is $CH_2$, Y is a single bond, $R^2$ is $NR^3R^4$, $R^3$ and $R^4$ represent together morpholin-4-yl, then T is not 3-chloro-2-methylphenyl;

$A_1$ is a nitrogen atom and $A_2$ is C—Z, X is CO, Y is CO, $R^2$ is $R^5O$, $R^5$ is ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 4-phenoxyphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-phenoxyphenyl"

$A_1$ is a nitrogen atom and $A_2$ is C—Z, X is $CH_2$, $R^2$ is hydrogen, then T is not 4-[(1,3-benzothiazol-2-ylthio)acetylamino]phenyl;

$A_1$ is a nitrogen atom and $A_2$ is C—Z, X is $CH_2$, Y is a single bond, $R^2$ is methyl, then T is not 4-[(1,3-benzothiazol-2-ylthio)acetylamino]phenyl;

$A_1$ is C—Z and $A_2$ is a nitrogen atom, Z is phenyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ are ethyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 1,1'-biphenyl-4-yl;

$A_1$ is a nitrogen atom and $A_2$ is C—Z, Z is phenyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ are both ethyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 4-bromo-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-bromo-2-methylphenyl;

$A_1$ is a nitrogen atom and $A_2$ is C—Z, Z is ethylthio, then T is not 4-bromophenyl;

$A_1$ is a nitrogen atom and $A_2$ is C—Z, Z is phenyl, then T is not 4-bromophenyl;

$A_1$ is a nitrogen atom and $A_2$ is C—Z, Z is tert-butyl, then T is not 4-bromophenyl;

$A_1$ is a nitrogen atom and $A_2$ is C—Z, Z is trifluoromethyl, then T is not 4-bromophenyl;

$A_1$ is a nitrogen atom and $A_2$ is C—Z, $A_3$ is methyl, then T is not 4-bromophenyl;

$A_1$ is a nitrogen atom and $A_2$ is C—Z, X is $CH_2$, Y is a single bond, $R^2$ is $R^5O$, $R^5$ is methyl, then T is not 4-bromophenyl;

$A_1$ is a nitrogen atom and $A_2$ is C—Z, X is $CH_2$, Y is a single bond, $R^2$ is hydrogen, then T is not 4-bromophenyl;

$A_1$ is C—Z and $A_2$ is a nitrogen atom, X is $CH_2$, Y is a single bond, $R^2$ is hydrogen, then T is not 4-n-butoxyphenyl;

$A_1$ is a nitrogen atom and $A_2$ is C—Z, X is $CH_2$, Y is $CH_2$, $R^2$ is hydrogen, then T is not 4-[(5-chloro-2-hydroxybenzyl)amino]phenyl;

$A_1$ is a nitrogen atom and $A_2$ is C—Z, X is $CH_2$, Y is a single bond, $R^2$ is methyl, then T is not 4-[(5-chloro-2-hydroxybenzyl)amino]phenyl;

$A_1$ is a nitrogen atom and $A_2$ is C—Z, Z is n-butylthio, then T is not 4-chlorophenyl;

$A_1$ is a nitrogen atom and $A_2$ is C—Z, Z is cyclohexyl, then T is not 4-chlorophenyl;

$A_1$ is a nitrogen atom and $A_2$ is C—Z, Z is ethylthio, then T is not 4-chlorophenyl;

$A_1$ is a nitrogen atom and $A_2$ is C—Z, Z is methoxy, then T is not 4-chlorophenyl;

$A_1$ is a nitrogen atom and $A_2$ is C—Z, Z is phenyl, then T is not 4-chlorophenyl;

$A_1$ is a nitrogen atom and $A_2$ is C—Z, Z is (trifluoromethyl), then T is not 4-chlorophenyl;

$A_1$ is a nitrogen atom and $A_2$ is C—Z, $A_3$ is methyl, then T is not 4-chlorophenyl;

$A_1$ is a nitrogen atom and $A_2$ is C—Z, X is $CH_2$, Y is a single bond, $R^2$ is hydrogen, then T is not 4-chlorophenyl;

$A_1$ is a nitrogen atom and $A_2$ is C—Z, X is $CH_2$, Y is a single bond, $R^2$ is 4-chlorophenyl, then T is not 4-chlorophenyl;

$A_1$ is a nitrogen atom and $A_2$ is C—Z, X is $CH_2$, Y is a single bond, $R^2$ is isopropyl, then T is not 4-chlorophenyl;

$A_1$ is a nitrogen atom and $A_2$ is Z, X is $CH_2$, Y is a single bond, $R^2$ is $NR^3R^4$, $R^3$ and $R^4$ are both methyl, then T is not 4-chlorophenyl;

$A_1$ is a nitrogen atom and $A_2$ is C—Z, X is $CH_2$, Y is a single bond, $R^2$ is $NR^3R^4$, $R^3$ and $R^4$ are both ethyl, then T is not 4-chlorophenyl;

$A_1$ is a nitrogen atom and $A_2$ is Z, X is $CH_2$, Y is $CH_2$, $R^2$ is $NR^3R^4$, $R^3$ and $R^4$ are both methyl, then T is not 4-chlorophenyl;

$A_1$ is a nitrogen atom and $A_2$ is C—Z, X is $CH_2$, Y is $CH_2$, $R^2$ is $NR^3R^4$, $R^3$ and $R^4$ are both ethyl, then T is not 4-chlorophenyl;

$A_1$ is a nitrogen atom and $A_2$ is C—Z, Z is cyclopropyl, then T is not 3,4-dichlorophenyl;

$A_1$ is a nitrogen atom and $A_2$ is C—Z, Z is trifluoromethyl, then T is not 3,4-dichlorophenyl;

$A_1$ is C—Z and $A_2$ is a nitrogen atom, Z is phenyl, then T is not 2,4-dichloro-6-methylphenyl;

$A_1$ is C—Z and $A_2$ is a nitrogen atom, X is $CH_2$, Y is $CH_2$, $R^2$ is $NR^1R^4$, $R^3$ and $R^4$ represent together morpholin-4-yl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, Z is phenyl, then T is not 2,4-dichloro-6-methylphenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, Z is cyclohexyl, then T is not 4-fluorophenyl;

$A_1$ is a nitrogen atom and $A_2$ is C—Z, Z is ethylthio, then T is not 4-fluorophenyl;

$A_1$ is a nitrogen atom and $A_2$ is C—Z, Z is tert-butyl then T is not 4-fluorophenyl;

$A_1$ is a nitrogen atom and $A_2$ is C—Z, Z is (trifluoromethyl), then T is not 4-fluorophenyl;

$A_1$ is a nitrogen atom and $A_2$ is C—Z, X is $CH_2$, Y is a single bond, $R^2$ is isopropyl, then T its not 4-fluorophenyl;

$A_1$ is a nitrogen atom and $A_2$ is C—Z, X is $CH_2$, Y is a single bond, $R^2$ is $R^5O$, $R^5$ is methyl, then T is not 4-fluorophenyl;

$A_1$ is C—Z and $A_2$ is a nitrogen atom, Z is ethylthio, then T is not 4-methylphenyl;

$A_1$ is C—Z and $A_2$ is a nitrogen atom, Z is phenyl, then T is not 4-methylphenyl;

$A_1$ is C—Z and $A_2$ is a nitrogen atom, X is $CH_2$, Y is $CH_2$, $R^2$ is hydrogen, then T is not 4-methylphenyl;

$A_1$ is C—Z and $A_2$ is a nitrogen atom, X is $CH_2$, Y is $CH_2$, $R^2$ is $R^5O$, $R^5$ is ethyl, then T is not 4-methylphenyl;

$A_1$ is C—Z and $A_2$ is a nitrogen atom, X is $CH_2$, Y is a single bond, $R^2$ is hydrogen, then T is not 4-methylphenyl;

$A_1$ is C—Z and $A_2$ is a nitrogen atom, X is $CH_2$, Y is a single bond, $R^2$ is methyl, then T is not 4-methylphenyl;

$A_1$ is a nitrogen atom and $A_2$ is C—Z, Z is [(1,3-benzodioxol-5-ylaminocarbonyl)methyl]-thio, then T is not 4-methylphenyl;

$A_1$ is a nitrogen atom and $A_2$ is C—Z, Z is n-butylthio, then T is not 4-methylphenyl;

$A_1$ is a nitrogen atom and $A_2$ is C—Z, Z is cyclohexyl, then T is not 4-methylphenyl;

$A_1$ is a nitrogen atom and $A_2$ is C—Z, Z is ethylthio, then T is not 4-methylphenyl;

$A_1$ is a nitrogen atom and $A_2$ is C—Z, Z is methoxy, then T is not 4-methylphenyl;

$A_1$ is a nitrogen atom and $A_2$ is C—Z, Z is phenyl, then T is not 4-methylphenyl;

$A_1$ is a nitrogen atom and $A_2$ is C—Z, Z is (trifluoromethyl), then T is not 4-methylphenyl;

$A_1$ is a nitrogen atom and $A_2$ is C—Z, $A_3$ is methyl, then T is not 4-methylphenyl;

A₁ is a nitrogen atom and A₂ is C—Z, X is CH₂, Y is a single bond, R² is isopropyl, then T is not 4-methylphenyl;

A₁ is a nitrogen atom and A₂ is C—Z, X is CH₂, Y is a single bond, R² is 4-methoxyphenyl, then T is not 4-methylphenyl;

A₁ is a nitrogen atom and A₂ is Z, X is CH₂, Y is a single bond, R² is NR³R⁴, R³ and R⁴ are both methyl, then T is not 4-methylphenyl;

A₁ is a nitrogen atom and A₂ is C—Z, X is CH₂, Y is a single bond, R² is NR³R⁴, R³ and R⁴ are both ethyl, then T is not 4-methylphenyl;

A₁ is a nitrogen atom and A₂ is Z, X is CH₂, Y is CH₂, R² is NR³R⁴, R³ and R⁴ are both methyl, then T is not 4-methylphenyl;

A₁ is a nitrogen atom and A₂ is C—Z, X is CH₂, Y is CH₂, R² is NR³R⁴, R³ and R⁴ are both ethyl, then T is not 4-methylphenyl;

A₁ is a nitrogen atom and A₂ is C—Z, X is CH₂, Y is CH₂, R² is hydrogen, then T is not 4-[(4-methylphthalazin-1-yl)amino]phenyl;

A₁ is a nitrogen atom and A₂ is C—Z, X is CH₂, Y is a single bond, R is methyl, then T is not 4-[(4-methylphthalazin-1-yl)amino]phenyl;

A₁ is a nitrogen atom and A₂ is C—Z, Z is ethylthio, then T is not 2-naphthyl;

A₁ is a nitrogen atom and A₂ is C—Z, X is CH₂, Y is a single bond, R² is hydrogen, then T is not 2-naphthyl;

A₁ is a nitrogen atom and A₂ is C—Z, Z is cyclohexyl, then T is not 4-nitrophenyl;

A₁ is a nitrogen atom and A₂ is C—Z, Z is methoxy, then T is not 4-nitrophenyl;

A₁ is a nitrogen atom and A₂ is C—Z, Z is ethylthio, then T is not 4-nitrophenyl;

A₁ is a nitrogen atom and A₂ is C—Z, Z is trifluoromethyl, then T is not 4-nitrophenyl;

A₁ is a nitrogen atom and A₂ is C—Z, Z is tert-butyl, then T is not 4-nitrophenyl;

A₁ is a nitrogen atom and A₂ is C—Z, X is CH₂, Y is a single bond, R² is hydrogen, then T is not 4-nitrophenyl;

A₁ is a nitrogen atom and A₂ is C—Z, X is CH₂, Y is a single bond, R² is 4-chlorophenyl, then T is not 4-nitrophenyl;

A₁ is a nitrogen atom and A₂ is C—Z, X is CH₂, Y is a single bond, R² is isopropyl, then T is not 4-nitrophenyl;

A₁ is a nitrogen atom and A₂ is C—Z, X is CH₂, Y is a single bond, R² is 4-methoxyphenyl, then T is not 4-nitrophenyl;

A₁ is a nitrogen atom and A₂ is C—Z, X is CH₂, Y is a single bond, R² is tert-butyl, then T is not 4-nitrophenyl;

A₁ is C—Z and A₂ is a nitrogen atom, Z is phenyl, then T is not 2,4,6-trichlorophenyl;

A₁ is C—Z and A₂ is a nitrogen atom, X is CH₂, Y is CH₂, R² is NR³R⁴, R³ and R⁴ represent together morpholin-4-yl, then T is not 2,4,6-trichlorophenyl;

A₁ is C—Z and A₂ is a nitrogen atom, X is CH₂, Y is CO, R² is NR³R⁴, R³ is ethyl and R⁴ is methyl, then T is not 2,4,6-trichlorophenyl;

A₁ is C—Z and A₂ is a nitrogen atom, X is CH₂, Y is CO, R² is NR³R⁴, R³ and R⁴ are both ethyl, then T is not 2,4,6-trichlorophenyl;

A₁ is C—Z and A₂ is a nitrogen atom, X is CH₂, Y is CO, R² is NR³R⁴, R³ and R⁴ represent together morpholin-4-yl, then T is not 2,4,6-trichlorophenyl;

A₁ is a nitrogen atom and A₂ is C—Z, Z is phenyl, then T is not 2,4,6-trichlorophenyl;

A₁ is a nitrogen atom and A₂ is C—Z, X is CH₂, Y is CH₂, R² is NR³R⁴, R³ and R⁴ represent together morpholin-4-yl, then T is not 2,4,6-trichlorophenyl;

A₁ is a nitrogen atom and A₂ is C—Z, X is CH₂, Y is CO, R² is NR³R⁴, R³ is ethyl and R⁴ is methyl, then T is not 2,4,6-trichlorophenyl;

A₁ is a nitrogen atom and A₂ is C—Z, X is CH₂, Y is CO, R² is NR³R⁴, R³ and R⁴ are both ethyl, then T is not 2,4,6-trichlorophenyl;

A₁ is a nitrogen atom and A₂ is C—Z, X is CH₂, Y is CO, R² is NR³R⁴, R³ and R⁴ represent together morpholin-4-yl, then T is not 2,4,6-trichlorophenyl;

A₁ is a nitrogen atom and A₂ is C—Z, X is CH₂, Y is CH₂, R² is hydrogen, then T is not 4-(trifluoromethoxy)phenyl;

A₁ is a nitrogen atom and A₂ is C—Z, X is CH₂, Y is a single bond, R² is hydrogen, then T is not 4-(trifluoromethoxy)phenyl;

A₁ is a nitrogen atom and A₂ is C—Z, X is CH₂, Y is a single bond, R² is methyl, then T is not 4-(trifluoromethoxy)phenyl;

A₁ is a nitrogen atom and A₂ is C—Z, Z is cyclohexyl, then T is not 2,4,6-trimethylphenyl;

A₁ is a nitrogen atom and A₂ is C—Z, A₃ is methyl, then T is not 2,4,6-trimethylphenyl;

A₁ is a nitrogen atom and A₂ is C—Z, Z is (trifluoromethyl), then T is not 2,4,6-trimethylphenyl;

A₁ is a nitrogen atom and A₂ is C—Z, X is CH₂, Y is a single bond, R² is hydrogen, then T is not 2,4,6-trimethylphenyl;

A₁ is a nitrogen atom and A₂ is C—Z, X is CH₂, Y is a single bond, R² is R⁵O, R⁵ is methyl, then T is not 2,4,6-trimethylphenyl.

It is preferred that T is selected from the group consisting of 2-acetylamino-4-methylthiazol-5-yl, 4-acetylphenyl, 4-benzoylaminophenyl, benzyl, 2,5-bis(2,2,2-trifluoroethoxy)phenyl, 3,5-bis(trifluoromethyl)phenyl, 5-bromo-6-chloropyridin-3-yl, 5-bromo-2-methoxyphenyl, 4-(3-chloro-2-cyanophenoxy)phenyl, 5-chloro-1,3-dimethyl-1H-pyrazol-4-yl, 3-chloro-5-fluoro-2-methylphenyl, 3-chloro-4-fluorophenyl, 3-chloro-4-methylphenyl, 4-chloro-3-nitrophenyl, 5-chloro-4-nitro-2-thienyl, 5-chlorothien-2-yl, 2-cyanophenyl, 3-cyanophenyl, 4-cyanophenyl, 3,5-dichloro-2-hydroxyphenyl, 2,6-dichlorophenyl, 4,5-dichloro-2-thienyl, 2,4-difluorophenyl, 2,6-difluorophenyl, 2,3-dihydro-1,4-benzodioxin-6-yl, 2,3-dihydro-1-benzofuran-5-yl, 3,4-dimethoxyphenyl, 5-(dimethylamino)-1-naphthyl, 1,2-dimethyl-1H-imidazol-4-yl, 3,5-dimethylisoxazol-4-yl, 5-fluoro-2-methylphenyl, 3-fluorophenyl, 4-(4-fluorophenylcarbonylamino)phenyl, 4-methoxy-2,3,6-trimethylphenyl, 4-methyl-3,4-dihydro-2H-1,4-benzoxazin-7-yl, 1-methyl-1H-imidazol-4-yl, 2-methyl-5-nitrophenyl, 3-(5-methyl-1,3,4-oxadiazol-2-yl)phenyl, 3-(2-methylpyrimidin-4-yl)phenyl, 5-[2-(methylthio)pyrimidin-4-yl)-2-thienyl, 5-methyl-2-(trifluoromethyl)-3-furyl, 4-morpholin-4-ylpyridin-3-yl, 1-naphthyl, 2-nitrophenyl, 3-nitrophenyl, 4-(1,3-oxazol-5-yl)phenyl, 2,2,4,6,7-pentamethyl-2,3-dihydro-1-benzofuran-5-yl, 6-phenoxypyridin-3-yl, 4-(phenylsulfonyl)-2-thienyl, 4-(1H-pyrazol-1-yl)phenyl, 5-pyridin-2-yl-2-thienyl, quinolin-8-yl, 4-tert-butylphenyl, 4-(1H-tetrazol-1-yl)phenyl, 2-thienyl, 3-(trifluoromethoxy)phenyl, 2-(trifluoromethyl)phenyl, and 1,3,5-trimethyl-1H-pyrazol-4-yl;

with the proviso that when R¹ is hydrogen and
A₁ is a nitrogen atom and A₂ is C—Z and T is benzyl, then Z is not 2,2-dimethyl-n-propyl, methoxymethyl, isopropyl, tert-butyl, cyclohexyl, isobutyl, 4-methoxybenzyl, trifluoromethyl, and methyl;
A₁ is a nitrogen atom and A₂ is C—Z, X is CH₂, Y is a single bond, R² is hydrogen, then T is not 2-nitrophenyl;
A₁ is a nitrogen atom and A₂ is C—Z, X is CH₂, Y is a single bond, R² is hydrogen, then T is not 4-tert-butylphenyl;
A₁ is a nitrogen atom and A₂ is C—Z, X is CH₂, Y is CH₂, R² is hydrogen, then T is not 4-benzoylaminophenyl;
A₁ is a nitrogen atom and A₂ is C—Z, X is CH₂, Y is a single bond, R² is methyl, then T is not 4-benzoylaminophenyl.

Preferred compounds are:
N-(3-isopropyl-1,2,4-thiadiazol-5-yl)quinoline-8-sulfonamide;
3-cyano-N-(3-ethyl-1,2,4-thiadiazol-5-yl)benzenesulfonamide;
N-(3-isopropyl-1,2,4-thiadiazol-5-yl)-3-(2-methylpyrimidin-4-yl)benzenesulfonamide;
N-(3-isopropyl-1,2,4-thiadiazol-5-yl)-1,3,5-trimethyl-1H-pyrazole-4-sulfonamide;
N-(3-isopropyl-1,2,4-thiadiazol-5-yl)-3,5-dimethylisoxazole-4-sulfonamide;
N-(3-tert-butyl-1,2,4-thiadiazol-5-yl)-3-cyanobenzenesulfonamide;
N-(3-ethyl-1,2,4-thiadiazol-5-yl)-5-fluoro-2-methylbenzenesulfonamide;
N-(3-isopropyl-1,2,4-thiadiazol-5-yl)-1-methyl-1H-imidazole-4-sulfonamide;
N-(3-isopropyl-1,2,4-thiadiazol-5-yl)-1-phenylmethanesulfonamide;
3-chloro-4-methyl-N-(3-phenyl-1,2,4-thiadiazol-5-yl)benzenesulfonamide;
N-(5-{[(3-isopropyl-1,2,4-thiadiazol-5-yl)amino]sulfonyl}-4-methyl-1,3-thiazol-2-yl)acetamide;
N-(3-isopropyl-1,2,4-thiadiazol-5-yl)-3-(5-methyl-1,3,4-oxadiazol-2-yl)benzenesulfonamide;
3-cyano-N-(3-isopropyl-1,2,4-thiadiazol-5-yl)benzenesulfonamide;
2-cyano-N-(3-isopropyl-1,2,4-thiadiazol-5-yl)benzenesulfonamide;
5-bromo-N-(3-isopropyl-1,2,4-thiadiazol-5-yl)-2-methoxybenzenesulfonamide;
N-(3-isopropyl-1,2,4-thiadiazol-5-yl)-6-morpholin-4-ylpyridine-3-sulfonamide;
N-(3-isopropyl-1,2,4-thiadiazol-5-yl)-3-(trifluoromethoxy)benzenesulfonamide;
N-(3-isopropyl-1,2,4-thiadiazol-5-yl)thiophene-2-sulfonamide;
5-chloro-N-(3-isopropyl-1,2,4-thiadiazol-5-yl)-1,3-dimethyl-1H-pyrazole-4-sulfonamide;
N-(3-isopropyl-1,2,4-thiadiazol-5-yl)-4-methyl-3,4-dihydro-2H-1,4-benzoxazine-7-sulfonamide;
5-chloro-N-(3-phenyl-1,2,4-thiadiazol-5-yl)thiophene-2-sulfonamide;
4-chloro-3-nitro-N-[3-(2-thienyl)-1,2,4-thiadiazol-5-yl]benzenesulfonamide;
4-cyano-N-(3-isopropyl-1,2,4-thiadiazol-5-yl)benzenesulfonamide;
N-(3-isopropyl-1,2,4-thiadiazol-5-yl)-2,3-dihydro-1-benzofuran-5-sulfonamide;
N-(3-isopropyl-1,2,4-thiadiazol-5-yl)-3,4-dimethoxybenzenesulfonamide;
N-(3-isopropyl-1,2,4-thiadiazol-5-yl)-2,3-dihydro-1,4-benzodioxine-6-sulfonamide;
N-(3-isopropyl-1,2,4-thiadiazol-5-yl)-6-phenoxypyridine-3-sulfonamide;
3-fluoro-N-(3-isopropyl-1,2,4-thiadiazol-5-yl)benzenesulfonamide;
N-(3-isopropyl-1,2,4-thiadiazol-5-yl)-3-nitrobenzenesulfonamide;
N-(3-isopropyl-1,2,4-thiadiazol-5-yl)-2-nitrobenzenesulfonamide;
N-(3-isopropyl-1,2,4-thiadiazol-5-yl)-3,5-bis(trifluoromethyl)benzenesulfonamide;
5-(dimethylamino)-N-(3-isopropyl-1,2,4-thiadiazol-5-yl)naphthalene-1-sulfonamide;
4-acetyl-N-(3-isopropyl-1,2,4-thiadiazol-5-yl)benzenesulfonamide;
N-(3-isopropyl-1,2,4-thiadiazol-5-yl)naphthalene-1-sulfonamide;
2,6-difluoro-N-(3-isopropyl-1,2,4-thiadiazol-5-yl)benzenesulfonamide;
N-(3-isopropyl-1,2,4-thiadiazol-5-yl)-2-(trifluoromethyl)benzenesulfonamide;
3,5-dichloro-2-hydroxy-N-(3-isopropyl-1,2,4-thiadiazol-5-yl)benzenesulfonamide;
5-fluoro-N-(3-isopropyl-1,2,4-thiadiazol-5-yl)-2-methylbenzenesulfonamide;
N-(3-isopropyl-1,2,4-thiadiazol-5-yl)-2-methyl-5-nitrobenzenesulfonamide;
2,4-difluoro-N-(3-isopropyl-1,2,4-thiadiazol-5-yl)benzenesulfonamide;
N-(3-isopropyl-1,2,4-thiadiazol-5-yl)-5-methyl-2-(trifluoromethyl)furan-3-sulfonamide;
N-(3-isopropyl-1,2,4-thiadiazol-5-yl)-4-(phenylsulfonyl)thiophene-2-sulfonamide;
3-chloro-4-fluoro-N-(3-isopropyl-1,2,4-thiadiazol-5-yl)benzenesulfonamide;
N-(3-ethyl-1,2,4-thiadiazol-5-yl)-5-[2-(methylthio)pyrimidin-4-yl]thiophene-2-sulfonamide;
5-bromo-6-chloro-N-(3-isopropyl-1,2,4-thiadiazol-5-yl)pyridine-3-sulfonamide;
3-chloro-N-(3-isopropyl-1,2,4-thiadiazol-5-yl)-4-methylbenzenesulfonamide;
N-(3-isopropyl-1,2,4-thiadiazol-5-yl)-4-(1H-pyrazol-1-yl)benzenesulfonamide;
N-(3-isopropyl-1,2,4-thiadiazol-5-yl)-2,2,4,6,7-pentamethyl-2,3-dihydro-1-benzofuran-5-sulfonamide;
N-(3-isopropyl-1,2,4-thiadiazol-5-yl)-4-methoxy-2,3,6-trimethylbenzenesulfonamide;
N-(3-isopropyl-1,2,4-thiadiazol-5-yl)-5-pyridin-2-ylthiophene-2-sulfonamide;
N-(3-isopropyl-1,2,4-thiadiazol-5-yl)-4-(1,3-oxazol-5-yl)benzenesulfonamide;
2,6-dichloro-N-(3-isopropyl-1,2,4-thiadiazol-5-yl)benzenesulfonamide;
4-(3-chloro-2-cyanophenoxy)-N-(3-isopropyl-1,2,4-thiadiazol-5-yl)benzenesulfonamide;
5-chloro-N-(3-isopropyl-1,2,4-thiadiazol-5-yl)-4-nitrothiophene-2-sulfonamide;
3-chloro-5-fluoro-N-(3-isopropyl-1,2,4-thiadiazol-5-yl)-2-methylbenzenesulfonamide;
4,5-dichloro-N-(3-isopropyl-1,2,4-thiadiazol-5-yl)thiophene-2-sulfonamide;
5-fluoro-2-methyl-N-[3-(2-thienyl)-1,2,4-thiadiazol-5-yl]benzenesulfonamide;
4-tert-butyl-N-(3-phenyl-1,2,4-thiadiazol-5-yl)benzenesulfonamide;

4-chloro-N-(3-morpholin-4-yl-1,2,4-thiadiazol-5-yl)-3-nitrobenzenesulfonamide
3-chloro-4-fluoro-N-(3-phenyl-1,2,4-thiadiazol-5-yl)benzenesulfonamide
N-(3-isopropyl-1,2,4-thiadiazol-5-yl)-2,5-bis(2,2,2-trifluoroethoxy)benzenesulfonamide
N-(3-isopropyl-1,2,4-thiadiazol-5-yl)-1,2-dimethyl-1H-imidazole-4-sulfonamide
N-(3-phenyl-1,2,4-thiadiazol-5-yl)naphthalene-1-sulfonamide
N-(3-phenyl-1,2,4-thiadiazol-5-yl)thiophene-2-sulfonamide
2-nitro-N-(3-phenyl-1,2,4-thiadiazol-5-yl)benzenesulfonamide
5-fluoro-2-methyl-N-(3-morpholin-4-yl-1,2,4-thiadiazol-5-yl)benzenesulfonamide
4-tert-butyl-N-(3-methyl-1,2,4-thiadiazol-5-yl)benzenesulfonamide
4-cyano-N-(3-methyl-1,2,4-thiadiazol-5-yl)benzenesulfonamide
N-(4-{[(5-ethyl-1,3,4-thiadiazol-2-yl)amino]sulfonyl}phenyl)-4-fluorobenzamide;
5-fluoro-N-(5-isopropyl-1,3,4-thiadiazol-2-yl)-2-methylbenzenesulfonamide;
4-chloro-N-[5-(ethylthio)-1,3,4-thiadiazol-2-yl]-3-nitrobenzenesulfonamide;
N-(4-{[(5-methyl-1,3,4-thiadiazol-2-yl)amino]sulfonyl}phenyl)benzamide;
N-(5-ethyl-1,3,4-thiadiazol-2-yl)-4-(1H-tetrazol-1-yl)benzenesulfonamide;
3-cyano-N-(5-isopropyl-1,3,4-thiadiazol-2-yl)benzenesulfonamide;
3-cyano-N-(5-phenyl-1,3,4-thiadiazol-2-yl)benzenesulfonamide;
5-bromo-N-(5-isopropyl-1,3,4-thiadiazol-2-yl)-2-methoxybenzenesulfonamide.

It is also preferred that T is 3-chloro-2-methylphenyl; with the proviso that when $R^1$ is hydrogen and $A_1$ is C—Z and $A_2$ is a nitrogen atom, Z is phenyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is hydrogen, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is methyl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is methyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are methyl, then T is not 3-chloro-2-methylphenyl;

$A_1$ is C—Z and $A_2$ is a nitrogen atom, X is $CH_2$, Y is CO, $R^2$ is $NR^3R^4$ $R^3$ is ethyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is $CH_2$, Y is CO, $R^2$ is $R^5O$, $R^5$ is hydrogen, then T is not 3-chloro-2-methylphenyl;

$A_1$ is C—Z and $A_2$ is a nitrogen atom, X is $CH_2$, Y is CO, $R^2$ is $R^5O$, $R^5$ is methyl, then T is not 3-chloro-2-methylphenyl;

$A_1$ is C—Z and $A_2$ is a nitrogen atom, X is $CH_2$, Y is CO, $R^2$ is $R^5O$, $R^5$ is ethyl, then T is not 3-chloro-2-methylphenyl;

$A_1$ is C—Z and $A_2$ is a nitrogen atom, X is $CH_2$, Y is a single bond, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is CO, Y is CO, $R^2$ is $R^5O$, $R^5$ is ethyl, then T is not 3-chloro-2-methylphenyl;

$A_1$ is a nitrogen atom and $A_2$ is C—Z, Z is phenyl, then T is not 3-chloro-2-methylphenyl;

$A_1$ is a nitrogen atom and $A_2$ is C—Z, X is $CH_2$, Y is $CH_2$, $R^2$ is $NR^3R^4$, $R^3$ and $R^4$ are both ethyl, then T is not 3-chloro-2-methylphenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 3-chloro-2-methylphenyl;

$A_1$ is a nitrogen atom and $A_2$ is C—Z, X is $CH_2$, Y is $CH_2$, $R^2$ is $R^5O$, $R^5$ is hydrogen, then T is not 3-chloro-2-methylphenyl;

$A_1$ is a nitrogen atom and $A_2$ is C—Z, X is $CH_2$, Y is $CH_2$, $R^2$ is $R^5O$, $R^5$ is methyl, then T is not 3-chloro-2-methylphenyl;

$A_1$ is a nitrogen atom and $A_2$ is C—Z, X is $CH_2$, Y is $CH_2$, $R^2$ is $R^5O$, $R^5$ is ethyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ are both hydrogen, then T is not 3-chloro-2-methylphenyl;

$A_1$ is a nitrogen atom and $A_2$ is C—Z, X is $CH_2$, Y is CO, $R^2$ is $NR^3R^4$, $R^3$ is methyl and $R^4$ is hydrogen, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ are both methyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ is ethyl and $R^4$ is hydrogen, then T is not 3-chloro-2-methylphenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 3-chloro-2-methylphenyl;

$A_1$ is a nitrogen atom and $A_2$ is C—Z, X is $CH_2$, Y is CO, $R^2$ is $R^5O$, $R^5$ is hydrogen, then T is not 3-chloro-2-methylphenyl;

A₁ is a nitrogen atom and A₂ is C—Z, X is CH₂, Y is CO, R² is R⁵O, R⁵ is methyl, then T is not 3-chloro-2-methylphenyl;

A₁ is a nitrogen atom and A₂ is C—Z, X is CH₂, Y is CO, R² is R⁵O, R⁵ is ethyl, then T is not 3-chloro-2-methylphenyl;

A₁ is a nitrogen atom and A₂ is C—Z, X is CH₂, Y is a single bond, R² is NR³R⁴, R³ and R⁴ represent together morpholin-4-yl, then T is not 3-chloro-2-methylphenyl;

A₁ is a nitrogen atom and A₂ is C—Z, X is CO, Y is CO, R² is R⁵O, R⁵ is ethyl, then T is not 3-chloro-2-methylphenyl.

Preferred compounds are:

Ethyl 1-[(5-{[(3-chloro-2-methylphenyl)sulfonyl]amino}-1,2,4-thiadiazol-3-yl)carbonyl]piperidine-4-carboxylate;

5-{[(3-chloro-2-methylphenyl)sulfonyl]amino}-N-methyl-1,2,4-thiadiazole-3-carboxamide;

5-{[(3-chloro-2-methylphenyl)sulfonyl]amino}-1,2,4-thiadiazole-3-carboxamide;

5-{[(3-chloro-2-methylphenyl)sulfonyl]amino}-1,2,4-thiadiazole-3-carboxylic acid;

3-chloro-2-methyl-N-{3-[(4-methylpiperazin-1-yl)carbonyl]-1,2,4-thiadiazol-5-yl}benzenesulfonamide;

3-chloro-N-[3-(3-furyl)-1,2,4-thiadiazol-5-yl]-2-methylbenzenesulfonamide;

3-chloro-N-(3-{[3-(hydroxymethyl)piperidin-1-yl]carbonyl}-1,2,4-thiadiazol-5-yl)-2-methylbenzenesulfonamide;

3-chloro-2-methyl-N-(3-methyl-1,2,4-thiadiazol-5-yl)benzenesulfonamide;

(R)-2-(5-{[(3-chloro-2-methylphenyl)sulfonyl]amino}-1,2,4-thiadiazol-3-yl)propanamide;

N-(4-{[(5-{[(3-chloro-2-methylphenyl)sulfonyl]amino}-1,2,4-thiadiazol-3-yl)methyl]thio}phenyl)acetamide;

3-chloro-2-methyl-N-(3-morpholin-4-yl-1,2,4-thiadiazol-5-yl)benzenesulfonamide;

(R)-N-(4-{[1-(5-{[(3-chloro-2-methylphenyl)sulfonyl]amino}-1,2,4-thiadiazol-3-yl)ethyl]thio}phenyl)acetamide;

5-{[(3-chloro-2-methylphenyl)sulfonyl]amino}-N-(3-ethoxypropyl)-1,2,4-thiadiazole-3-carboxamide;

3-chloro-2-methyl-N-{3-[(phenylsulfonyl)methyl]-1,2,4-thiadiazol-5-yl}benzenesulfonamide;

3-chloro-2-methyl-N-[3-(3-thienyl)-1,2,4-thiadiazol-5-yl]benzenesulfonamide;

(R)-N-[2-(5-{[(3-chloro-2-methylphenyl)sulfonyl]amino}-1,2,4-thiadiazol-3-yl)propyl]butanamide;

3-chloro-2-methyl-N-[3-(morpholin-4-ylcarbonyl)-1,2,4-thiadiazol-5-yl]benzenesulfonamide;

Ethyl 1-[(5-{[(3-chloro-2-methylphenyl)sulfonyl]amino}-1,2,4-thiadiazol-3-yl)carbonyl]piperidine-3-carboxylate;

3-chloro-N-{3-[(3-hydroxypiperidin-1-yl)carbonyl]-1,2,4-thiadiazol-5-yl}-2-methylbenzenesulfonamide;

3-chloro-2-methyl-N-[3-(trichloromethyl)-1,2,4-thiadiazol-5-yl]benzenesulfonamide;

3-chloro-2-methyl-N-[3-(2-thienyl)-1,2,4-thiadiazol-5-yl]benzenesulfonamide;

3-chloro-N-(3-methoxy-1,2,4-thiadiazol-5-yl)-2-methylbenzenesulfonamide;

(R)-3-chloro-N-(3-{1-[(3,4-dimethoxyphenyl)thio]ethyl}-1,2,4-thiadiazol-5-yl)-2-methylbenzenesulfonamide;

3-chloro-N-(3-ethyl-1,2,4-thiadiazol-5-yl)-2-methylbenzenesulfonamide;

N-(3-{[(5-{[(3-chloro-2-methylphenyl)sulfonyl]amino}-1,2,4-thiadiazol-3-yl)methyl]thio}phenyl)acetamide;

3-chloro-2-methyl-N-(3-{[(4-methylpyrimidin-2-yl)thio]methyl}-1,2,4-thiadiazol-5-yl)benzenesulfonamide;

(R)-3-chloro-2-methyl-N-(3-{1-[(4-methylpyrimidin-2-yl)thio]ethyl}-1,2,4-thiadiazol-5-yl)benzenesulfonamide;

(R)-2-(5-{[(3-chloro-2-methylphenyl)sulfonyl]amino}-1,2,4-thiadiazol-3-yl)-1-methylethyl 3-chloro-2-methylbenzenesulfonate;

3-chloro-2-methyl-N-{3-[(3-oxopiperazin-1-yl)carbonyl]-1,2,4-thiadiazol-5-yl}benzenesulfonamide;

3-chloro-N-(3-{[(3,4-dimethoxyphenyl)thio]methyl}-1,2,4-thiadiazol-5-yl)-2-methylbenzenesulfonamide;

(R)-3-chloro-2-methyl-N-{3-[1-(phenylsulfonyl)ethyl]-1,2,4-thiadiazol-5-yl}benzenesulfonamide;

3-chloro-N-(3-{[(2-methoxyphenyl)thio]methyl)}-1,2,4-thiadiazol-5-yl)-2-methylbenzenesulfonamide;

(R)-3-chloro-2-methyl-N-{3-[1-(pyridin-3-yloxy)ethyl]-1,2,4-thiadiazol-5-yl}benzenesulfonamide;

(R)-3-chloro-2-methyl-N-{3-[1-(pyridin-4-ylthio)ethyl]-1,2,4-thiadiazol-5-yl}benzenesulfonamide;

3-chloro-2-methyl-N-(3-{[(1-methyl-1H-imidazol-2-yl)thio]methyl}-1,2,4-thiadiazol-5-yl)benzenesulfonamide;

3-chloro-2-methyl-N-{3-[(pyridin-4-ylthio)methyl]-1,2,4-thiadiazol-5-yl}benzenesulfonamide;

(R)-3-chloro-N-(3-{1-[(2-methoxyphenyl)thio]ethyl}-1,2,4-thiadiazol-5-yl)-2-methylbenzenesulfonamide;

N-(2-{[(5-{[(3-chloro-2-methylphenyl)sulfonyl]amino}-1,2,4-thiadiazol-3-yl)methyl]thio}phenyl)acetamide;

3-chloro-2-methyl-N-{3-[(pyridin-2-ylthio)methyl]-1,2,4-thiadiazol-5-yl}benzenesulfonamide;

(R)-3-chloro-N-(3-{2-[(3-fluorophenyl)thio]propyl}-1,2,4-thiadiazol-5-yl)-2-methylbenzenesulfonamide;

N-(3-tert-butyl-1,2,4-thiadiazol-5-yl)-3-chloro-2-methylbenzenesulfonamide;

(R)-3-chloro-N-{3-[1-(2,3-difluorophenoxy)ethyl]-1,2,4-thiadiazol-5-yl}-2-methylbenzenesulfonamide;

5-{[(3-chloro-2-methylphenyl)sulfonyl]amino}-N,N-diethyl-1,2,4-thiadiazole-3-carboxamide;

3-chloro-N-(3-{[(3-methoxyphenyl)thio]methyl}-1,2,4-thiadiazol-5-yl)-2-methylbenzenesulfonamide;

(R)-3-chloro-N-(3-{1-[(3-methoxyphenyl)thio]ethyl}-1,2,4-thiadiazol-5-yl)-2-methylbenzenesulfonamide;

3-chloro-N-(3-isopropyl-1,2,4-thiadiazol-5-yl)-2-methylbenzenesulfonamide;

3-chloro-2-methyl-N-{3-[(phenylthio)methyl]-1,2,4-thiadiazol-5-yl}benzenesulfonamide;

(R)-3-chloro-2-methyl-N-[3-(1-phenoxyethyl)-1,2,4-thiadiazol-5-yl]benzenesulfonamide;

(R)-3-chloro-2-methyl-N-(3-{1-[(1-methyl-1H-imidazol-2-yl)thio]ethyl}-1,2,4-thiadiazol-5-yl)benzenesulfonamide;

(R)-3-chloro-2-methyl-N-[3-(1-{[3-(trifluoromethyl)phenyl]thio}ethyl)-1,2,4-thiadiazol-5-yl]benzenesulfonamide;

(R)-3-chloro-N-{3-[1-(3-fluorophenoxy)ethyl]-1,2,4-thiadiazol-5-yl}-2-methylbenzenesulfonamide;

(R)-3-chloro-N-{3-[1-(3,5-difluorophenoxy)ethyl]-1,2,4-thiadiazol-5-yl}-2-methylbenzenesulfonamide;

3-chloro-N-(3-{[(3-fluorophenyl)thio]methyl}-1,2,4-thiadiazol-5-yl)-2-methylbenzenesulfonamide;

3-chloro-N-(3-isobutyl-1,2,4-thiadiazol-5-yl)-2-methylbenzenesulfonamide;

3-chloro-N-(3-{[(2,4-difluorophenyl)thio]methyl}-1,2,4-thiadiazol-5-yl)-2-methylbenzenesulfonamide;

(R)-3-chloro-N-(3-{1-[(3-fluorophenyl)thio]ethyl}-1,2,4-thiadiazol-5-yl)-2-methylbenzenesulfonamide;
(R)-3-chloro-2-methyl-N-{3-[1-(phenylthio)ethyl]-1,2,4-thiadiazol-5-yl}benzenesulfonamide;
3-chloro-N-(3-{[(3,4-difluorophenyl)thio]methyl}-1,2,4-thiadiazol-5-yl)-2-methylbenzenesulfonamide;
3-chloro-2-methyl-N-{3-[2-(4-methylpiperazin-1-yl)ethyl]-1,2,4-thiadiazol-5-yl}benzenesulfonamide;
N-(4-{[(5-{[(3-chloro-2-methylphenyl)sulfonyl]amino}-1,2,4-thiadiazol-3-yl)methyl]sulfonyl}phenyl)acetamide;
3-chloro-N-{3-[(diethylamino)methyl]-1,2,4-thiadiazol-5-yl}-2-methylbenzenesulfonamide trifluoroacetate;
5-{[(3-chloro-2-methylphenyl)sulfonyl]amino}-1,3,4-thiadiazole-2-carboxylic acid;
N-[5-(4-tert-butylphenyl)-1,3,4-thiadiazol-2-yl]-3-chloro-2-methylbenzenesulfonamide;
3-chloro-2-methyl-N-[5-(2-methylpyridin-3-yl)-1,3,4-thiadiazol-2-yl]benzenesulfonamide;
3-chloro-2-methyl-N-[5-(pyridin-3-ylmethyl)-1,3,4-thiadiazol-2-yl]benzenesulfonamide;
3-chloro-2-methyl-N-{5-[(4-nitrophenoxy)methyl]-1,3,4-thiadiazol-2-yl}benzenesulfonamide;
3-chloro-2-methyl-N-[5-(trifluoromethyl)-1,3,4-thiadiazol-2-yl]benzenesulfonamide;
3-chloro-N-(5-ethyl-1,3,4-thiadiazol-2-yl)-2-methylbenzenesulfonamide;
Ethyl [(5-{[(3-chloro-2-methylphenyl)sulfonyl]amino}-1,3,4-thiadiazol-2-yl)thio]acetate;
3-chloro-N-(5-isopropyl-1,3,4-thiadiazol-2-yl)-2-methylbenzenesulfonamide;
3-chloro-N-{5-[(4-fluorophenoxy)methyl]-1,3,4-thiadiazol-2-yl}-2-methylbenzenesulfonamide;
3-chloro-N-{5-[(4-chlorophenoxy)methyl]-1,3,4-thiadiazol-2-yl}-2-methylbenzenesulfonamide;
N-(5-tert-butyl-1,3,4-thiadiazol-2-yl)-3-chloro-2-methylbenzenesulfonamide;
N-{5-[(2-allylphenoxy)methyl]-1,3,4-thiadiazol-2-yl}-3-chloro-2-methylbenzenesulfonamide;
(R)-3-chloro-2-methyl-N-[5-(1-phenoxypropyl)-1,3,4-thiadiazol-2-yl]benzenesulfonamide;
3-chloro-2-methyl-N-[5-({[2-(4-methylphenoxy)ethyl]thio}methyl)-1,3,4-thiadiazol-2-yl]benzenesulfonamide;
(R)-3-chloro-2-methyl-N-[5-(1-phenylethyl)-1,3,4-thiadiazol-2-yl]benzenesulfonamide;
3-chloro-N-[5-(ethylthio)-1,3,4-thiadiazol-2-yl]-2-methylbenzenesulfonamide;
3-chloro-N-{5-[(2-fluorophenoxy)methyl]-1,3,4-thiadiazol-2-yl}-2-methylbenzenesulfonamide;
(R)-3-chloro-2-methyl-N-[5-(1-phenylpropyl)-1,3,4-thiadiazol-2-yl]benzenesulfonamide;
3-chloro-2-methyl-N-{5-[(phenylthio)methyl]-1,3,4-thiadiazol-2-yl}benzenesulfonamide;
3-chloro-N-(5-{[(4-fluorobenzyl)thio]methyl}-1,3,4-thiadiazol-2-yl)-2-methylbenzenesulfonamide;
N-{5-[(benzylthio)methyl]-1,3,4-thiadiazol-2-yl}-3-chloro-2-methylbenzenesulfonamide.

It is also preferred that T is 4-phenoxyphenyl;
with the proviso that when $R^1$ is hydrogen and
$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 4-phenoxyphenyl;
$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-phenoxyphenyl.

Preferred compounds are:
(R)-N-(4-{[1-(5-{[(4-phenoxyphenyl)sulfonyl]amino}-1,2,4-thiadiazol-3-yl)ethyl]thio}phenyl)acetamide;
N-(3-morpholin-4-yl-1,2,4-thiadiazol-5-yl)-4-phenoxybenzenesulfonamide;
N-[3-(3-furyl)-1,2,4-thiadiazol-5-yl]-4-phenoxybenzenesulfonamide;
4-phenoxy-N-[3-(3-thienyl)-1,2,4-thiadiazol-5-yl]benzenesulfonamide;
N,N-diethyl-2-(5-{[(4-phenoxyphenyl)sulfonyl]amino}-1,2,4-thiadiazol-3-yl)acetamide;
4-phenoxy-N-[3-(2-thienyl)-1,2,4-thiadiazol-5-yl]benzenesulfonamide;
N-[3-(morpholin-4-ylcarbonyl)-1,2,4-thiadiazol-5-yl]-4-phenoxybenzenesulfonamide;
N-(3-methyl-1,2,4-thiadiazol-5-yl)-4-phenoxybenzenesulfonamide;
N-(3-methoxy-1,2,4-thiadiazol-5-yl)-4-phenoxybenzenesulfonamide;
N-(3-tert-butyl-1,2,4-thiadiazol-5-yl)-4-phenoxybenzenesulfonamide;
N-(3-ethyl-1,2,4-thiadiazol-5-yl)-4-phenoxybenzenesulfonamide;
N-(3-isopropyl-1,2,4-thiadiazol-5-yl)-4-phenoxybenzenesulfonamide;
N,N-diethyl-5-{[(4-phenoxyphenyl)sulfonyl]amino}-1,2,4-thiadiazole-3-carboxamide;
4-phenoxy-N-{3-[(phenylthio)methyl]-1,2,4-thiadiazol-5-yl} benzenesulfonamide;
N-(3-cyclopropyl-1,2,4-thiadiazol-5-yl)-4-phenoxybenzenesulfonamide;
N-{3-[(diethylamino)methyl]-1,2,4-thiadiazol-5-yl}-4-phenoxybenzenesulfonamide trifluoroacetate;
N-[3-(2-ethoxyethyl)-1,2,4-thiadiazol-5-yl]-4-phenoxybenzenesulfonamide;
N-[3-(morpholin-4-ylmethyl)-1,2,4-thiadiazol-5-yl]-4-phenoxybenzenesulfonamide trifluoroacetate;
4-phenoxy-N-(5-phenyl-1,3,4-thiadiazol-2-yl)benzenesulfonamide;
N-(5-isopropyl-1,3,4-thiadiazol-2-yl)-4-phenoxybenzenesulfonamide.

It is also preferred that T is selected from the group consisting of 4-[(1,3-benzothiazol-2-ylthio)acetylamino]phenyl, 1,1'-biphenyl-4-yl, 4-bromo-2-methylphenyl, 4-bromophenyl, 4-n-butoxyphenyl, 4-[(5-chloro-2-hydroxybenzyl)amino]phenyl, 4-chlorophenyl, 3,4-dichlorophenyl, 2,4-dichloro-6-methylphenyl, 4-fluorophenyl, 4-methylphenyl, 4-[(4-methylphthalazin-1-yl)amino]phenyl, 2-naphthyl, 4-nitrophenyl, 2,4,6-trichlorophenyl, 4-(trifluoromethoxy)phenyl, and 2,4,6-trimethylphenyl;
with the proviso that when $R^1$ is hydrogen and
$A_1$ is a nitrogen atom and $A_2$ is C—Z, X is $CH_2$, Y is $CH_2$, $R^2$ is hydrogen, then T is not 4-[(1,3-benzothiazol-2-ylthio)acetylamino]phenyl;
$A_1$ is a nitrogen atom and $A_2$ is C—Z, X is $CH_2$, Y is a single bond, $R^2$ is methyl, then T is not 4-[(1,3-benzothiazol-2-ylthio)acetylamino]phenyl;
$A_1$ is C—Z and $A_2$ is a nitrogen atom, Z is phenyl, then T is not 1,1'-biphenyl-4-yl;
$A_1$ is C—Z and $A_2$ is a nitrogen atom, X is $CH_2$, Y is CO, $R^2$ is $NR^3R^4$, $R^3$ is ethyl and $R^4$ is methyl, then T is not 1,1'-biphenyl-4-yl;
$A_1$ is C—Z and $A_2$ is a nitrogen atom, X is $CH_2$, Y is CO, $R^2$ is $NR^3R^4$, $R^3$ and $R^4$ are both ethyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 1,1'-biphenyl-4-yl;

$A_1$ is a nitrogen atom and $A_2$ is C—Z, Z is phenyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ are both ethyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 4-bromo-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-bromo-2-methylphenyl;

$A_1$ is a nitrogen atom and $A_2$ is C—Z, Z is ethylthio, then T is not 4-bromophenyl;

$A_1$ is a nitrogen atom and $A_2$ is C—Z, Z is phenyl, then T is not 4-bromophenyl;

$A_1$ is a nitrogen atom and $A_2$ is C—Z, Z is tert-butyl, then T is not 4-bromophenyl;

$A_1$ is a nitrogen atom and $A_2$ is C—Z, Z is trifluoromethyl, then T is not 4-bromophenyl;

$A_1$ is a nitrogen atom and $A_2$ is C—Z, $A_3$ is methyl, then T is not 4-bromophenyl;

$A_1$ is a nitrogen atom and $A_2$ is C—Z, X is $CH_2$, Y is a single bond, $R^2$ is $R^5O$, $R^5$ is methyl, then T is not 4-bromophenyl;

$A_1$ is a nitrogen atom and $A_2$ is C—Z, X is $CH_2$, Y is a single bond, $R^2$ is hydrogen, then T is not 4-bromophenyl;

$A_1$ is C—Z and $A_2$ is a nitrogen atom, X is $CH_2$, Y is a single bond, $R^2$ is hydrogen, then T is not 4-n-butoxyphenyl;

$A_1$ is a nitrogen atom and $A_2$ is C—Z, X is $CH_2$, Y is $CH_2$, $R^2$ is hydrogen, then T is not 4-[(5-chloro-2-hydroxybenzyl)amino]phenyl;

$A_1$ is a nitrogen atom and $A_2$ is C—Z, X is $CH_2$, Y is a single bond, $R^2$ is methyl, then T is not 4-[(5-chloro-2-hydroxybenzyl)amino]phenyl;

$A_1$ is a nitrogen atom and $A_2$ is C—Z, Z is n-butylthio, then T is not 4-chlorophenyl;

$A_1$ is a nitrogen atom and $A_2$ is C—Z, Z is cyclohexyl, then T is not 4-chlorophenyl;

$A_1$ is a nitrogen atom and $A_2$ is C—Z, Z is ethylthio, then T is not 4-chlorophenyl;

$A_1$ is a nitrogen atom and $A_2$ is C—Z, Z is methoxy, then T is not 4-chlorophenyl;

$A_1$ is a nitrogen atom and $A_2$ is C—Z, Z is phenyl, then T is not 4-chlorophenyl;

$A_1$ is a nitrogen atom and $A_2$ is C—Z, Z is (trifluoromethyl), then T is not 4-chlorophenyl;

$A_1$ is a nitrogen atom and $A_2$ is C—Z, $A_3$ is methyl, then T is not 4-chlorophenyl;

$A_1$ is a nitrogen atom and $A_2$ is C—Z, X is $CH_2$, Y is a single bond, $R^2$ is hydrogen, then T is not 4-chlorophenyl;

$A_1$ is a nitrogen atom and $A_2$ is C—Z, X is $CH_2$, Y is a single bond, $R^2$ is 4-chlorophenyl, then T is not 4-chlorophenyl;

$A_1$ is a nitrogen atom and $A_2$ is C—Z, X is $CH_2$, Y is a single bond, $R^2$ is isopropyl, then T is not 4-chlorophenyl;

$A_1$ is a nitrogen atom and $A_2$ is Z, X is $CH_2$, Y is a single bond, $R^2$ is $NR^3R^4$, $R^3$ and $R^4$ are both methyl, then T is not 4-chlorophenyl;

$A_1$ is a nitrogen atom and $A_2$ is C—Z, X is $CH_2$, Y is a single bond, $R^2$ is $NR^3R^4$, $R^3$ and $R^4$ are both ethyl, then T is not 4-chlorophenyl;

$A_1$ is a nitrogen atom and $A_2$ is Z, X is $CH_2$, Y is $CH_2$, $R^2$ is $NR^3R^4$, $R^3$ and $R^4$ are both methyl, then T is not 4-chlorophenyl;

$A_1$ is a nitrogen atom and $A_2$ is C—Z, X is $CH_2$, Y is $CH_2$, $R^2$ is $NR^3R^4$, $R^3$ and $R^4$ are both ethyl, then T is not 4-chlorophenyl;

$A_1$ is a nitrogen atom and $A_2$ is C—Z, Z is cyclopropyl, then T is not 3,4-dichlorophenyl;

$A_1$ is a nitrogen atom and $A_2$ is C—Z, Z is trifluoromethyl, then T is not 3,4-dichlorophenyl;

$A_1$ is C—Z and $A_2$ is a nitrogen atom, Z is phenyl, then T is not 2,4-dichloro-6-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, Z is phenyl, then T is not 2,4-dichloro-6-methylphenyl;

$A_1$ is a nitrogen atom and $A_2$ is C-Z, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, Z is cyclohexyl, then T is not 4-fluorophenyl;

$A_1$ is a nitrogen atom and $A_2$ is C—Z, Z is ethylthio, then T is not 4-fluorophenyl;

$A_1$ is a nitrogen atom and $A_2$ is C—Z, Z is tert-butyl then T is not 4-fluorophenyl;

$A_1$ is a nitrogen atom and $A_2$ is C—Z, Z is (trifluoromethyl), then T is not 4-fluorophenyl;

$A_1$ is a nitrogen atom and $A_2$ is C—Z, X is $CH_2$, Y is a single bond, $R^2$ is isopropyl, then T is not 4-fluorophenyl;

$A_1$ is a nitrogen atom and $A_2$ is C—Z, X is $CH_2$, Y is a single bond, $R^2$ is $R^5O$, $R^5$ is methyl, then T is not 4-fluorophenyl;

$A_1$ is C—Z and $A_2$ is a nitrogen atom, Z is ethylthio, then T is not 4-methylphenyl;

$A_1$ is C—Z and $A_2$ is a nitrogen atom, Z is phenyl, then T is not 4-methylphenyl;

$A_1$ is C—Z and $A_2$ is a nitrogen atom, X is $CH_2$, Y is $CH_2$, $R^2$ is hydrogen, then T is not 4-methylphenyl;

$A_1$ is C—Z and $A_2$ is a nitrogen atom, X is $CH_2$, Y is $CH_2$, $R^2$ is $R^5O$, $R^5$ is ethyl, then T is not 4-methylphenyl;

$A_1$ is C—Z and $A_2$ is a nitrogen atom, X is $CH_2$, Y is a single bond, $R^2$ is hydrogen, then T is not 4-methylphenyl;

$A_1$ is C—Z and $A_2$ is a nitrogen atom, X is $CH_2$, Y is a single bond, $R^2$ is methyl, then T is not 4-methylphenyl;

$A_1$ is a nitrogen atom and $A_2$ is C—Z, Z is [(1,3-benzodioxol-5-ylaminocarbonyl)methyl]-thio, then T is not 4-methylphenyl;

$A_1$ is a nitrogen atom and $A_2$ is C—Z, Z is n-butylthio, then T is not 4-methylphenyl;

$A_1$ is a nitrogen atom and $A_2$ is C—Z, Z is cyclohexyl, then T is not 4-methylphenyl;

$A_1$ is a nitrogen atom and $A_2$ is C—Z, Z is ethylthio, then T is not 4-methylphenyl;

$A_1$ is a nitrogen atom and $A_2$ is C—Z, Z is methoxy, then T is not 4-methylphenyl;

$A_1$ is a nitrogen atom and $A_2$ is C—Z, Z is phenyl, then T is not 4-methylphenyl;

$A_1$ is a nitrogen atom and $A_2$ is C—Z, Z is (trifluoromethyl), then T is not 4-methylphenyl;

$A_1$ is a nitrogen atom and $A_2$ is C—Z, $A_3$ is methyl, then T is not 4-methylphenyl;

$A_1$ is a nitrogen atom and $A_2$ is C—Z, X is $CH_2$, Y is a single bond, $R^2$ is isopropyl, then T is not 4-methylphenyl;

$A_1$ is a nitrogen atom and $A_2$ is C—Z, X is $CH_2$, Y is a single bond, $R^2$ is 4-methoxyphenyl, then T is not 4-methylphenyl;

$A_1$ is a nitrogen atom and $A_2$ is Z, X is $CH_2$, Y is a single bond, $R^2$ is $NR^3R^4$, $R^3$ and $R^4$ are both methyl, then T is not 4-methylphenyl;

$A_1$ is a nitrogen atom and $A_2$ is C—Z, X is $CH_2$, Y is a single bond, $R^2$ is $NR^3R^4$, $R^3$ and $R^4$ are both ethyl, then T is not 4-methylphenyl;

$A_1$ is a nitrogen atom and $A_2$ is Z, X is $CH_2$, Y is $CH_2$, $R^2$ is $NR^3R^4$, $R^3$ and R are both methyl, then T is not 4-methylphenyl;

$A_1$ is a nitrogen atom and $A_2$ is C—Z, X is $CH_2$, Y is $CH_2$, $R^2$ is $NR^3$, $R^3$ and $R^4$ are both ethyl, then T is not 4-methylphenyl;

$A_1$ is a nitrogen atom and $A_2$ is C—Z, X is $CH_2$, Y is $CH_2$, $R^2$ is hydrogen, then T is not 4-[(4-methylphthalazin-1-yl)amino]phenyl;

$A_1$ is a nitrogen atom and $A_2$ is C—Z, X is $CH_2$, Y is a single bond, $R^2$ is methyl, then T is not 4-[(4-methylphthalazin-1-yl)amino]phenyl;

$A_1$ is a nitrogen atom and $A_2$ is C—Z, Z is ethylthio, then T is not 2-naphthyl;

$A_1$ is a nitrogen atom and $A_2$ is C—Z, X is $CH_2$, Y is a single bond, $R^2$ is hydrogen, then T is not 2-naphthyl;

$A_1$ is a nitrogen atom and $A_2$ is C—Z, Z is cyclohexyl, then T is not 4-nitrophenyl;

$A_1$ is a nitrogen atom and $A_2$ is C—Z, Z is methoxy, then T is not 4-nitrophenyl;

$A_1$ is a nitrogen atom and $A_2$ is C—Z, Z is ethylthio, then T is not 4-nitrophenyl;

$A_1$ is a nitrogen atom and $A_2$ is C—Z, Z is trifluoromethyl, then T is not 4-nitrophenyl;

$A_1$ is a nitrogen atom and $A_2$ is C—Z, Z is tert-butyl, then T is not 4-nitrophenyl;

$A_1$ is a nitrogen atom and $A_2$ is C—Z, X is $CH_2$, Y is a single bond, $R^2$ is hydrogen, then T is not 4-nitrophenyl;

$A_1$ is a nitrogen atom and $A_2$ is C—Z, X is $CH_2$, Y is a single bond, $R^2$ is 4-chlorophenyl, then T is not 4-nitrophenyl;

$A_1$ is a nitrogen atom and $A_2$ is C—Z, X is $CH_2$, Y is a single bond, $R^2$ is isopropyl, then T is not 4-nitrophenyl;

$A_1$ is a nitrogen atom and $A_2$ is C—Z, X is $CH_2$, Y is a single bond, $R^2$ is 4-methoxyphenyl, then T is not 4-nitrophenyl;

$A_1$ is a nitrogen atom and $A_2$ is C—Z, X is $CH_2$, Y is a single bond, $R^2$ is tert-butyl, then T is not 4-nitrophenyl;

$A_1$ is C—Z and $A_2$ is a nitrogen atom, Z is phenyl, then T is not 2,4,6-trichlorophenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 2,4,6-trichlorophenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 2,4,6-trichlorophenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4,6-trichlorophenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4,6-trichlorophenyl;

$A_1$ is a nitrogen atom and $A_2$ is C—Z, Z is phenyl, then T is not 2,4,6-trichlorophenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 2,4,6-trichlorophenyl;

$A_1$ is a nitrogen atom and $A_2$ is C-Z, X is $CH_2$, Y is CO, $R^2$ is $NR^3R^4$, $R^3$ is ethyl and $R^4$ is methyl, then T is not 2,4,6-trichlorophenyl;

$A_1$ is a nitrogen atom and $A_2$ is C-Z, X is $CH_2$, Y is CO, $R^2$ is $NR^3R^4$, $R^3$ and $R^4$ are both ethyl, then T is not 2,4,6-trichlorophenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4,6-trichlorophenyl;

$A_1$ is a nitrogen atom and $A_2$ is C—Z, X is $CH_2$, Y is $CH_2$, $R^2$ is hydrogen, then T is not 4-(trifluoromethoxy)phenyl;

$A_1$ is a nitrogen atom and $A_2$ is C—Z, X is $CH_2$, Y is a single bond, $R^2$ is hydrogen, then T is not 4-(trifluoromethoxy)phenyl;

$A_1$ is a nitrogen atom and $A_2$ is C—Z, X is $CH_2$, Y is a single bond, $R^2$ is methyl, then T is not 4-(trifluoromethoxy)phenyl;

$A_1$ is a nitrogen atom and $A_2$ is C—Z, Z is cyclohexyl, then T is not 2,4,6-trimethylphenyl;

$A_1$ is a nitrogen atom and $A_2$ is C—Z, $A_3$ is methyl, then T is not 2,4,6-trimethylphenyl;

$A_1$ is a nitrogen atom and $A_2$ is C—Z, Z is (trifluoromethyl), then T is not 2,4,6-trimethylphenyl;

$A_1$ is a nitrogen atom and $A_2$ is C—Z, X is $CH_2$, Y is a single bond, $R^2$ is hydrogen, then T is not 2,4,6-trimethylphenyl;

$A_1$ is a nitrogen atom and $A_2$ is C—Z, X is $CH_2$, Y is a single bond, $R^2$ is $R^5O$, $R^5$ is methyl, then T is not 2,4,6-trimethylphenyl.

Preferred compounds are:

4-nitro-N-(3-phenyl-1,2,4-thiadiazol-5-yl)benzenesulfonamide;

N-(3-methoxy-1,2,4-thiadiazol-5-yl)-4-methylbenzenesulfonamide;

Ethyl 5-{[(4-bromo-2-methylphenyl)sulfonyl]amino}-1,2,4-thiadiazole-3-carboxylate;
4-chloro-N-(3-phenyl-1,2,4-thiadiazol-5-yl)benzenesulfonamide;
4-fluoro-N-(3-isopropyl-1,2,4-thiadiazol-5-yl)benzenesulfonamide;
4-methyl-N-[3-(morpholin-4-ylcarbonyl)-1,2,4-thiadiazol-5-yl]benzenesulfonamide;
N-[3-(3-furyl)-1,2,4-thiadiazol-5-yl]naphthalene-2-sulfonamide;
(R)-N-{4-[(1-{5-[(biphenyl-4-ylsulfonyl)amino]-1,2,4-thiadiazol-3-yl}ethyl)thio]phenyl}acetamide;
2,4,6-trichloro-N-(3-morpholin-4-yl-1,2,4-thiadiazol-5-yl)benzenesulfonamide;
N-(3-isopropyl-1,2,4-thiadiazol-5-yl)-4-methylbenzenesulfonamide;
N-(3-isopropyl-1,2,4-thiadiazol-5-yl)-4-nitrobenzenesulfonamide;
N-[3-(3-thienyl)-1,2,4-thiadiazol-5-yl]biphenyl-4-sulfonamide;
N-[3-(3-furyl)-1,2,4-thiadiazol-5-yl]biphenyl-4-sulfonamide;
4-methyl-N-[3-(trichloromethyl)-1,2,4-thiadiazol-5-yl]benzenesulfonamide;
N-(3-isopropyl-1,2,4-thiadiazol-5-yl)-2,4,6-trimethylbenzenesulfonamide;
4-bromo-N-(3-cyclopropyl-1,2,4-thiadiazol-5-yl)benzenesulfonamide;
4-methyl-N-{3-[(phenylthio)methyl]-1,2,4-thiadiazol-5-yl}benzenesulfonamide;
4-bromo-N-(3-tert-butyl-1,2,4-thiadiazol-5-yl)benzenesulfonamide;
N-(3-cyclopropyl-1,2,4-thiadiazol-5-yl)naphthalene-2-sulfonamide;
4-bromo-N-{3-[(phenylthio)methyl]-1,2,4-thiadiazol-5-yl}benzenesulfonamide;
N-(3-isopropyl-1,2,4-thiadiazol-5-yl)naphthalene-2-sulfonamide;
4-bromo-N-[3-(trichloromethyl)-1,2,4-thiadiazol-5-yl]benzenesulfonamide;
N-(3-tert-butyl-1,2,4-thiadiazol-5-yl)naphthalene-2-sulfonamide;
4-butoxy-N-(3-isopropyl-1,2,4-thiadiazol-5-yl)benzenesulfonamide;
(R)-N-(3-{1-[(3-fluorophenyl)thio]ethyl}-1,2,4-thiadiazol-5-yl)biphenyl-4-sulfonamide;
N-(3-tert-butyl-1,2,4-thiadiazol-5-yl)biphenyl-4-sulfonamide;
2,4-dichloro-N-(3-isopropyl-1,2,4-thiadiazol-5-yl)-6-methylbenzenesulfonamide;
2,4,6-trichloro-N-(3-isopropyl-1,2,4-thiadiazol-5-yl)benzenesulfonamide;
N-[3-(3-furyl)-1,2,4-thiadiazol-5-yl]-4-methylbenzenesulfonamide;
4-methyl-N-[3-(3-thienyl)-1,2,4-thiadiazol-5-yl]benzenesulfonamide;
4-fluoro-N-(3-phenyl-1,2,4-thiadiazol-5-yl)benzenesulfonamide;
N-(5-isopropyl-1,3,4-thiadiazol-2-yl)-4-nitrobenzenesulfonamide;
N-(5-isopropyl-1,3,4-thiadiazol-2-yl)-N-methylbiphenyl-4-sulfonamide;
N-(5-phenyl-1,3,4-thiadiazol-2-yl)naphthalene-2-sulfonamide;
4-bromo-N-[5-(4-methoxybenzyl)-1,3,4-thiadiazol-2-yl]benzenesulfonamide;
N-(5-isopropyl-1,3,4-thiadiazol-2-yl)naphthalene-2-sulfonamide;
4-bromo-N-(5-tert-butyl-1,3,4-thiadiazol-2-yl)benzenesulfonamide;
4-bromo-N-[5-(4-chlorobenzyl)-1,3,4-thiadiazol-2-yl]benzenesulfonamide;
N-(5-tert-butyl-1,3,4-thiadiazol-2-yl)naphthalene-2-sulfonamide;
N-[5-(2,2-dimethylpropyl)-1,3,4-thiadiazol-2-yl]-4-fluorobenzenesulfonamide;
N-(5-isopropyl-1,3,4-thiadiazol-2-yl)biphenyl-4-sulfonamide;
4-bromo-N-[5-(2,2-dimethylpropyl)-1,3,4-thiadiazol-2-yl]benzenesulfonamide;
N-[5-(methoxymethyl)-1,3,4-thiadiazol-2-yl]-4-nitrobenzenesulfonamide;
4-fluoro-N-(5-isopropyl-1,3,4-thiadiazol-2-yl)benzenesulfonamide.

The compound of formula (I) above may be of formula (II):

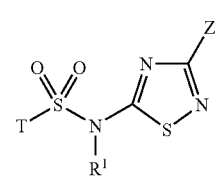

wherein T, $R^1$ and Z are as defined above.

The compound of formula (I) above may also be of formula (III):

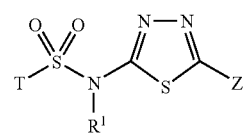

wherein T, $R^1$ and Z are as defined above.

Another object of the present invention is a compound as defined above for medical use.

Another object of the present invention is a method for the treatment or prevention of a disease or disorder by inhibition of the human 11-β-hydroxysteroid dehydrogenase type 1 enzyme, and to achieve immuno-modulation, said method comprising administering to a mammal, including a human, in need of such treatment an effective amount of a compound of formula (I)

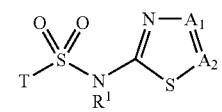

wherein

T is selected from 2-acetylamino-4-methylthiazol-5-yl; benzyl; 5-bromo-6-chloropyridin-3-yl; 5-chloro-1,3-dimethyl-1H-pyrazol-4-yl; 2,3-dihydro-1,4-benzodioxin-6-yl; 2,3-dihydro-1-benzofuran-5-yl; 5-(dimethylamino)-1-naphthyl; 1,2-dimethyl-1H-imidazol-4-yl; 3,5-dimethylisoxazol-4-yl; 4-methyl-3,4-dihydro-2H-1,4-benzoxazin-7-yl; 1-methyl-1H-imidazol-4-yl; 5-methyl-2-(trifluoromethyl)-3-furyl; 4-morpholin-4-ylpyridin-3-yl; 1-naphthyl; 2-naphthyl; 2,2,4,6,7-pentamethyl-2,3-dihydro-1-benzofuran-5-yl; 6-phenoxypyridin-3-yl; quinolin-8-yl; 1,3,5-trimethyl-1H-pyrazol-4-yl;

thienyl optionally substituted with one or more of acetylamino; chloro; methyl; 2-(methylthio)pyrimidin-4-yl; nitro; phenylsulfonyl; pyridinyl;

phenyl optionally substituted with one or more of acetyl; acetylamino; amino; 4-(1,3-benzothiazol-2-ylthio)acetylamino; benzoylamino; bromo; chloro; 3-chloro-2-cyanophenoxy; (5-chloro-2-hydroxybenzyl)amino; 4-chloro-3-nitrophenylcarbonylamino; [(4-chlorophenyl)amino]carbonylamino; cyano; 2,4-dichlorophenoxyacetylamino; fluoro; 4-{[(4-fluorophenyl)amino]carbonothioyl}amino; 4-fluorophenylcarbonylamino; hydroxy; methoxy; methyl; 5-methyl-1,3,4-oxadiazol-2-yl; (4-methylphthalazin-1-yl)amino; 1,3-oxazol-5-yl; 2-methyl-4-pyrimidyl; n-butoxy; nitro; N-phthalimido; phenoxy; phenyl; 1H-pyrazol-1-yl; tert-butyl; tetrazolyl; 2,2,2-trifluoroethoxy; trifluoromethoxy; trifluoromethyl;

$R^1$ is hydrogen or methyl;

$A_1$ and $A_2$ are a nitrogen atom or C—Z, provided that $A_1$ and $A_2$ have different meanings, wherein:

Z is [(1,3-benzodioxol-5-ylaminocarbonyl)methyl]thio; n-butylthio; (R)-2-[(3-chloro-2-methylbenzenesulfonyl)oxy]propyl; cyclohexyl; cyclopropyl; ethoxycarbonylmethylthio; ethylthio; (R)-2-[(3-fluorophenyl)thio]propyl; 3-furyl; methoxy; 2-methylpyridin-3-yl; morpholin-4-yl; (R)-1-phenoxy-n-propyl; phenyl; (R)-1-phenyl-n-propyl; tert-butyl; tert-butylphenyl; 2-thienyl; 3-thienyl; (trichloromethyl); (trifluoromethyl); $A_3$ or is —CH(CH$_3$)$A_3$, wherein $A_3$ is selected from methyl; carbamoyl; N-(n-butanamidyl); phenylsulfonyl; phenyl; phenoxy optionally substituted with one or more fluoro; phenylthio optionally substituted with one or more acetylamino, methoxy, trifluoromethyl, fluoro; pyridin-3-yloxy; 4-methylpyrimidin-2-ylthio; pyridin-4-ylthio; 1-methyl-1H-imidazol-2-ylthio; or X—Y—$R^2$, wherein X is CH$_2$ or CO;

Y is CH$_2$, CO or a single bond;

$R^2$ is selected from 4-acetylaminophenylsulfonyl; 1-(3-chloro-2-methylphenylsulfonyloxyl)ethyl; 1-[(3-fluorophenyl)thio]ethyl; 4-chlorophenyl; 3-ethoxy-n-propyl; hydrogen; isopropyl; 4-methoxyphenyl; methyl; phenylsulfonyl; pyridin-3-yl; tert-butyl;

NR$^3$R$^4$, wherein R$^3$ and R$^4$ are each independently selected from 3-ethoxy-n-propyl; ethyl; hydrogen; methyl;

NR$^3$R$^4$ represent together 3-carbethoxypiperidin-1-yl; 4-carbethoxypiperidin-1-yl; 3-hydroxymethylpiperidin-1-yl; 3-hydroxypiperidin-1-yl; 4-methylpiperazin-1-yl; morpholin-4-yl; 3-oxopiperazin-1-yl;

R$^5$O, wherein R$^5$ is 2-allylphenyl; 4-chlorophenyl; ethyl; 2-fluorophenyl; 4-fluorophenyl; hydrogen; methyl; 4-nitrophenyl;

R$^6$S, wherein R$^6$ is 2-acetylaminophenyl; 3-acetylaminophenyl; 4-acetylaminophenyl; benzyl; 2,4-difluorophenyl; 3,4-difluorophenyl; 3,4-dimethoxyphenyl; 4-fluorobenzyl; 3-fluorophenyl; 2-methoxyphenyl; 3-methoxyphenyl; 1-methyl-1H-imidazol-2-yl; 2-(4-methylphenoxy)ethyl; 4-methylpyrimidin-2-yl; phenyl; pyridin-2-yl; pyridin-4-yl;

pharmaceutically acceptable salts, solvates, hydrates, geometrical isomers, tautomers, optical isomers, N-oxides and prodrug forms thereof;

with the proviso that T is not selected from 4-acetylaminophenyl, 4-aminophenyl, 4-(4-chloro-3-nitrophenylcarbonylamino)phenyl, 4-{[(4-chlorophenyl)amino]carbonylamino}-phenyl, 4-(2,4-dichlorophenoxyacetylamino)phenyl, 4-({[(4-fluorophenyl)amino]-carbonothioyl}amino)phenyl, 4-methoxyphenyl, phenyl, 4-(N-phthalimido)phenyl, and 3-(trifluoromethyl)phenyl; and with the proviso that when $R^1$ is hydrogen and $A_1$ is C—Z and $A_2$ is a nitrogen atom, Z is phenyl, then T is not 3-chloro-2-methylphenyl;

$A_1$ is C—Z and $A_2$ is a nitrogen atom, X is CH$_2$, Y is CH$_2$, $R^2$ is NR$^3$R$^4$, R$^3$ and R$^4$ are both ethyl, then T is not 3-chloro-2-methylphenyl;

$A_1$ is C—Z and $A_2$ is a nitrogen atom, X is CH$_2$, Y is CH$_2$, $R^2$ is NR$^3$R$^4$, R$^3$ and R$^4$ represent together morpholin-4-yl, then T is not 3-chloro-2-methylphenyl;

$A_1$ is C—Z and $A_2$ is a nitrogen atom, X is CH$_2$, Y is CH$_2$, $R^2$ is R$^5$O, R$^5$ is hydrogen, then T is not 3-chloro-2-methylphenyl;

$A_1$ is C—Z and $A_2$ is a nitrogen atom, X is CH$_2$, Y is CH$_2$, $R^2$ is R$^5$O, R$^5$ is methyl, then T is not 3-chloro-2-methylphenyl;

$A_1$ is C—Z and $A_2$ is a nitrogen atom, X is CH$_2$, Y is CH$_2$, $R^2$ is R$^5$O, R$^5$ is ethyl, then T is not 3-chloro-2-methylphenyl;

$A_1$ is C—Z and $A_2$ is a nitrogen atom, X is CH$_2$, Y is CO, $R^2$ is NR$^3$R$^4$, R$^3$ and R$^4$ are both hydrogen, then T is not 3-chloro-2-methylphenyl;

$A_1$ is C—Z and $A_2$ is a nitrogen atom, X is CH$_2$, Y is CO, $R^2$ is NR$^3$R$^4$, R$^3$ is methyl and R$^4$ is hydrogen, then T is not 3-chloro-2-methylphenyl;

$A_1$ is C—Z and $A_2$ is a nitrogen atom, X is CH$_2$, Y is CO, $R^2$ is NR$^3$R$^4$, R$^3$ and R$^4$ are both methyl, then T is not 3-chloro-2-methylphenyl;

$A_1$ is C—Z and $A_2$ is a nitrogen atom, X is CH$_2$, Y is CO, $R^2$ is NR$^3$R$^4$, R$^3$ is ethyl and R$^4$ is hydrogen, then T is not 3-chloro-2-methylphenyl;

$A_1$ is C—Z and $A_2$ is a nitrogen atom, X is CH$_2$, Y is CO, $R^2$ is NR$^3$R$^4$, R$^3$ is ethyl and R$^4$ is methyl, then T is not 3-chloro-2-methylphenyl;

$A_1$ is C—Z and $A_2$ is a nitrogen atom, X is CH$_2$, Y is CO, $R^2$ is NR$^3$R$^4$, R$^3$ and R$^4$ are both ethyl, then T is not 3-chloro-2-methylphenyl;

$A_1$ is C—Z and $A_2$ is a nitrogen atom, X is CH$_2$, Y is CO, $R^2$ is NR$^3$R$^4$, R$^3$ and R$^4$ represent together morpholin-4-yl, then T is not 3-chloro-2-methylphenyl;

$A_1$ is C—Z and $A_2$ is a nitrogen atom, X is CH$_2$, Y is CO, $R^2$ is R$^5$O, R$^5$ is hydrogen, then T is not 3-chloro-2-methylphenyl;

$A_1$ is C—Z and $A_2$ is a nitrogen atom, X is CH$_2$, Y is CO, $R^2$ is R$^5$O, R$^5$ is methyl, then T is not 3-chloro-2-methylphenyl;

$A_1$ is C—Z and $A_2$ is a nitrogen atom, X is CH$_2$, Y is CO, $R^2$ is R$^5$O, R$^5$ is ethyl, then T is not 3-chloro-2-methylphenyl;

$A_1$ is C—Z and $A_2$ is a nitrogen atom, X is CH$_2$, Y is a single bond, $R^2$ is NR$^3$R$^4$, R$^3$ and R$^4$ represent together morpholin-4-yl, then T is not 3-chloro-2-methylphenyl;

$A_1$ is C—Z and $A_2$ is a nitrogen atom, X is CO, Y is CO, $R^2$ is R$^5$O, R$^5$ is ethyl, then T is not 3-chloro-2-methylphenyl;

$A_1$ is a nitrogen atom and $A_2$ is C—Z, X is CH$_2$, Y is CO, $R^2$ is NR$^3$R$^4$, R$^3$ and R$^4$ represent together morpholin-4-yl, then T is not 4-phenoxyphenyl;

A₁ is C—Z and A₂ is a nitrogen atom, Z is phenyl, then T is not 1,1'-biphenyl-4-yl;

A₁ is C—Z and A₂ is a nitrogen atom, X is CH₂, Y is CO, R² is NR³R⁴, R³ is ethyl and R⁴ is methyl, then T is not 1,1'-biphenyl-4-yl;

A₁ is C—Z and A₂ is a nitrogen atom, X is CH₂, Y is CO, R² is NR³R⁴, R³ and R⁴ are both ethyl, then T is not 1,1'-biphenyl-4-yl;

A₁ is C—Z and A₂ is a nitrogen atom, X is CH₂, Y is CO, R² is NR³R⁴, R³ and R⁴ represent together morpholin-4-yl, then T is not 1,1'-biphenyl-4-yl;

A₁ is a nitrogen atom and A₂ is C—Z, Z is phenyl, then T is not 1,1'-biphenyl-4-yl;

A₁ is a nitrogen atom and A₂ is C—Z, X is CH₂, Y is CO, R² is NR³R⁴, R³ is ethyl and R⁴ is methyl, then T is not 1,1'-biphenyl-4-yl;

A₁ is a nitrogen atom and A₂ is C—Z, X is CH₂, Y is CO, R² is NR³R⁴, R³ and R⁴ are both ethyl, then T is not 1,1'-biphenyl-4-yl;

A₁ is a nitrogen atom and A₂ is C—Z, X is CH₂, Y is CO, R² is NR³R⁴, R³ and R⁴ represent together morpholin-4-yl, then T is not 1,1'-biphenyl-4-yl;

A₁ is C—Z and A₂ is a nitrogen atom, X is CH₂, Y is CO, R² is NR³R⁴, R³ and R⁴ represent together morpholin-4-yl, then T is not 4-bromo-2-methylphenyl;

A₁ is a nitrogen atom and A₂ is C—Z, X is CH₂, Y is CO, R² is NR³R⁴, R³ and R⁴ represent together morpholin-4-yl, then T is not 4-bromo-2-methylphenyl;

A₁ is C—Z and A₂ is a nitrogen atom, Z is phenyl, then T is not 2,4-dichloro-6-methylphenyl;

A₁ is C—Z and A₂ is a nitrogen atom, X is CH₂, Y is CH₂, R² is NR³R⁴, R³ and R⁴ represent together morpholin-4-yl, then T is not 2,4-dichloro-6-methylphenyl;

A₁ is C—Z and A₂ is a nitrogen atom, X is CH₂, Y is CO, R² is NR³R⁴, R³ is ethyl and R⁴ is methyl, then T is not 2,4-dichloro-6-methylphenyl;

A₁ is C—Z and A₂ is a nitrogen atom, X is CH₂, Y is CO, R² is NR³R⁴, R³ and R⁴ are both ethyl, then T is not 2,4-dichloro-6-methylphenyl;

A₁ is C—Z and A₂ is a nitrogen atom, X is CH₂, Y is CO, R² is NR³R⁴, R³ and R⁴ represent together morpholin-4-yl, then T is not 2,4-dichloro-6-methylphenyl;

A₁ is a nitrogen atom and A₂ is C—Z, Z is phenyl, then T is not 2,4-dichloro-6-methylphenyl;

A₁ is a nitrogen atom and A₂ is C—Z, X is CH₂, Y is CH₂, R² is NR³R⁴, R³ and R⁴ represent together morpholin-4-yl, then T is not 2,4-dichloro-6-methylphenyl;

A₁ is a nitrogen atom and A₂ is C—Z, X is CH₂, Y is CO, R² is NR³R⁴, R³ is ethyl and R⁴ is methyl, then T is not 2,4-dichloro-6-methylphenyl;

A₁ is a nitrogen atom and A₂ is C—Z, X is CH₂, Y is CO, R² is NR³R⁴, R³ and R⁴ are both ethyl, then T is not 2,4-dichloro-6-methylphenyl;

A₁ is a nitrogen atom and A₂ is C—Z, X is CH₂, Y is CO, R² is NR³R⁴, R³ and R⁴ represent together morpholin-4-yl, then T is not 2,4-dichloro-6-methylphenyl;

A₁ is C—Z and A₂ is a nitrogen atom, Z is phenyl, then T is not 2,4,6-trichlorophenyl;

A₁ is C—Z and A₂ is a nitrogen atom, X is CH₂, Y is CO, R² is NR³R⁴, R³ is ethyl and R⁴ methyl, then T is not 2,4,6-trichlorophenyl;

A₁ is C—Z and A₂ is a nitrogen atom, X is CH₂, Y is CO, R² is NR³R⁴, R³ and R⁴ are both ethyl, then T is not 2,4,6-trichlorophenyl;

A₁ is C—Z and A₂ is a nitrogen atom, X is CH₂, Y is CH₂, R² is NR³R⁴, R³ and R⁴ is represent together morpholin-4-yl, then T is not 2,4,6-trichlorophenyl;

A₁ is C—Z and A₂ is a nitrogen atom, X is CH₂, Y is CO, R² is NR³R⁴, R³ and R⁴ represent together morpholin-4-yl, then T is not 2,4,6-trichlorophenyl;

A₁ is a nitrogen atom and A₂ is C—Z, Z is phenyl, then T is not 2,4,6-trichlorophenyl;

A₁ is a nitrogen atom and A₂ is C—Z, X is CH₂, Y is CO, R² is NR³R⁴, R³ is ethyl and R⁴ is methyl, then T is not 2,4,6-trichlorophenyl;

A₁ is a nitrogen atom and A₂ is C—Z, X is CH₂, Y is CO, R² is NR³R⁴, R³ and R⁴ are both ethyl, then T is not 2,4,6-trichlorophenyl;

A₁ is a nitrogen atom and A₂ is C—Z, X is CH₂, Y is CH₂, R² is NR³R⁴, R³ and R⁴ represent together morpholin-4-yl, then T is not 2,4,6-trichlorophenyl;

A₁ is a nitrogen atom and A₂ is C—Z, X is CH₂, Y is CO, R² is NR³R⁴, R³ and R⁴ represent together morpholin-4-yl, then T is not 2,4,6-trichlorophenyl.

One object comprises a compound of Formula (I)

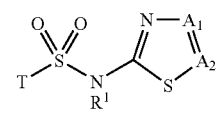

wherein

A₁ and A₂ are a nitrogen atom or C—Z, provided that A₁ and A₂ have different meanings, wherein, when A₂ is nitrogen and A₁ is C—Z, then Z is:

methoxy;

—C(O)-piperidinyl-(Rᴮ)ₙ;

—CH(Rᴬ)-phenyl-(Rᴮ)ₙ;

—CH(Rᴬ)—C(O)—NR₂ᴬ;

—(CH₂)ₘ—CH(Rᴬ)—Rᴰ-phenyl-(Rᴮ)ₙ;

—CR₃ᶜ; where Rᶜ is halogen;

—(CH₂)ₘ—CH(Rᴬ)—Rᴰ-heteroaryl-(Rᴮ)ₙ;

—C(O)NR₂ᴬ;

—CH(Rᴬ)—(CH₂)ₘ—N—C₁₋₆ amido;

—C₃–C₆-cycloalkyl; or

-morpholinyl;

where Rᴬ is independently H or C₁₋₆ alkyl or C₁₋₆ alkyl substituted with C₁₋₆ alkoxy;

Rᴮ is independently COORᴬ, CH₂OH, N—C₁₋₆ amido, C₁₋₆ alkoxy, optionally halogenated C₁₋₆ alkyl, halogen, or nitro;

Rᴰ is O, S, SO, SO₂ or OSO₂;

n is 0–4 and m is 0–1;

where T is selected from the group consisting of 2-acetylamino-4-methylthiazol-5-yl; benzyl; 5-bromo-6-chloropyridin-3-yl; 5-chloro-1,3-dimethyl-1H-pyrazol-4-yl; 2,3-dihydro-1,4-benzodioxin-6-yl; 2,3-dihydro-1-benzofuran-5-yl; 5-(dimethylamino)-1-naphthyl; 1,2-dimethyl-1H-imidazol-4-yl; 3,5-dimethylisoxazol-4-yl; 4-methyl-3,4-dihydro-2H-1,4-benzoxazin-7-yl; 1-methyl-1H-imidazol-4-yl; 5-methyl-2-(trifluoromethyl)-3-furyl; 4-morpholin-4-ylpyridin-3-yl; 1-naphthyl; 2-naphthyl; 2,2,4,6,7-pentamethyl-2,3-dihydro-1-benzofuran-5-yl; 6-phenoxypyridin-3-yl; quinolin-8-yl; and 1,3,5-trimethyl-1H-pyrazol-4-yl;

thienyl optionally substituted with one or more of acetylamino; chloro; methyl; 2-(methylthio)pyrimidin-4-yl; nitro; phenylsulfonyl; pyridinyl;

phenyl substituted with one or more of acetyl; acetylamino; amino; 4-(1,3-benzothiazol-2-ylthio)acetylamino; benzoylamino; bromo; chloro; 3-chloro-2-cyanophenoxy; (5-chloro-2-hydroxybenzyl)amino; 4-chloro-3-nitrophenylcarbonylamino; [(4-chlorophenyl)amino]carbonylamino; cyano; 2,4-dichlorophenoxyacetylamino; fluoro; 4-{[(4-fluorophenyl)amino]carbonothioyl}amino; 4-fluorophenylcarbonylamino; hydroxy; methoxy; methyl; 5-methyl-1,3,4-oxadiazol-2-yl; (4-methylphthalazin-1-yl)amino; 1,3-oxazol-5-yl; 2-methyl-4-pyrimidyl; n-butoxy; nitro; N-phthalimido; phenoxy; phenyl; 1H-pyrazol-1-yl; tert-butyl; tetrazolyl; 2,2,2-trifluoroethoxy; trifluoromethoxy; trifluoromethyl; and $R^1$ is hydrogen or methyl, pharmaceutically acceptable salts, solvates, hydrates, geometrical isomers, tautomers, optical isomers, N-oxides and prodrug forms thereof.

Another object comprises a compound of Formula (I)

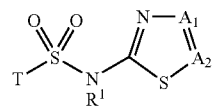

I wherein $A_1$ and $A_2$ are a nitrogen atom or C—Z, provided that $A_1$ and $A_2$ have different meanings, wherein:
when $A_1$ is nitrogen and $A_2$ is C—Z, then
Z is:
—S—$C_{1-6}$ alkyl;
—S—$CH_2$—C(O)—O—$C_{1-6}$ alkyl;
t-butyl;
—$CH_2$—S—$CH_2$—$CH_2$—O-phenyl-4-methyl; or
—S—$CH_2$—C(O)—NH-benzodioxol-5-yl, where T is selected from the group consisting of 2-acetylamino-4-methylthiazol-5-yl; benzyl; 5-bromo-6-chloropyridin-3-yl; 5-chloro-1,3-dimethyl-1H-pyrazol-4-yl; 2,3-dihydro-1,4-benzodioxin-6-yl; 2,3-dihydro-1-benzofuran-5-yl; 5-(dimethylamino)-1-naphthyl; 1,2-dimethyl-1H-imidazol-4-yl; 3,5-dimethylisoxazol-4-yl; 4-methyl-3,4-dihydro-2H-1,4-benzoxazin-7-yl; 1-methyl-1H-imidazol-4-yl; 5-methyl-2-(trifluoromethyl)-3-furyl; 4-morpholin-4-ylpyridin-3-yl; 1-naphthyl; 2-naphthyl; 2,2,4,6,7-pentamethyl-2,3-dihydro-1-benzofuran-5-yl; 6-phenoxypyridin-3-yl; quinolin-8-yl; and 1,3,5-trimethyl-1H-pyrazol-4-yl;

thienyl optionally substituted with one or more of acetylamino; chloro; methyl; 2-(methylthio)pyrimidin-4-yl; nitro; phenylsulfonyl; pyridinyl;

phenyl substituted with one or more of acetyl; acetylamino; amino; 4-(1,3-benzothiazol-2-ylthio)acetylamino; benzoylamino; bromo; chloro; 3-chloro-2-cyanophenoxy; (5-chloro-2-hydroxybenzyl)amino; 4-chloro-3-nitrophenylcarbonylamino; [(4-chlorophenyl)amino]carbonylamino; cyano; 2,4-dichlorophenoxyacetylamino; fluoro; 4-{[(4-fluorophenyl)amino]carbonothioyl}amino; 4-fluorophenylcarbonylamino; hydroxy; methoxy; methyl; 5-methyl-1,3,4-oxadiazol-2-yl; (4-methylphthalazin-1-yl)amino; 1,3-oxazol-5-yl; 2-methyl-4-pyrimidyl; n-butoxy; nitro; N-phthalimido; phenoxy; phenyl; 1H-pyrazol-1-yl; tert-butyl; tetrazolyl; 2,2,2-trifluoroethoxy; trifluoromethoxy; trifluoromethyl; and $R^1$ is hydrogen or methyl, pharmaceutically acceptable salts, solvates, hydrates, geometrical isomers, tautomers, optical isomers, N-oxides and prodrug forms thereof.

Another object comprises a compound of Formula (I)

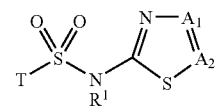

I wherein $A_1$ and $A_2$ are a nitrogen atom or C—Z, provided that $A_1$ and $A_2$ have different meanings, wherein, when $A_1$ is nitrogen and $A_2$ is C—Z, then
T is phenyl substituted with:
4-methylphthalazinylamino;
3-nitro-4-chloro-phenyl-carbonylamino;
4-fluorophenylcarbonylamino;
4-chlorophenylurea;
4-fluorophenylthiourea;
1,3-benzothiazolylthioacetamido;
2,4-dichlorophenoxyacetamido or
5-chloro-2-hydroxy-benzylamino;
Z is [(1,3-benzodioxol-5-ylaminocarbonyl)methyl]thio; n-butylthio; (R)-2-[(3-chloro-2-methylbenzenesulfonyl)oxy]propyl; cyclohexyl; cyclopropyl; ethoxycarbonylmethylthio; ethylthio; (R)-2-[(3-fluorophenyl)thio]propyl; 3-furyl; methoxy; 2-methylpyridin-3-yl; morpholin-4-yl; (R)-1-phenoxy-n-propyl; phenyl; (R)-1-phenyl-n-propyl; tert-butyl; tert-butylphenyl; 2-thienyl; 3-thienyl; (trichloromethyl); (trifluoromethyl); $A_3$, or —$CH(CH_3)A_3$, wherein $A_3$ is selected from methyl; carbamoyl; N-(n-butanamidyl); phenylsulfonyl; phenyl; phenoxy optionally substituted with one or more fluoro; phenylthio optionally substituted with one or more acetylamino, methoxy, trifluoromethyl, fluoro; pyridin-3-yloxy; 4-methylpyrimidin-2-ylthio; pyridin-4-ylthio; 1-methyl-1H-imidazol-2-ylthio;

or X—Y—$R^2$, wherein
X is $CH_2$ or CO;
Y is $CH_2$, CO or a single bond;
$R^2$ is selected from the group consisting of 4-acetylaminophenylsulfonyl; N-(n-butanamidyl); 1-(3-chloro-2-methylphenylsulfonyloxyl)ethyl; 1-[(3-fluorophenyl)thio]ethyl; 4-chlorophenyl; 3-ethoxy-n-propyl-, hydrogen; isopropyl; 4-methoxyphenyl; methyl; phenylsulfonyl; pyridin-3-yl; tert-butyl;

$NR^3R^4$, wherein $R^3$ and $R^4$ are each independently selected from 3-ethoxy-n-propyl; ethyl; hydrogen; methyl;
$NR^3R^4$ represent together 3-carbethoxypiperidin-1-yl; 4-carbethoxypiperidin-1-yl; 3-hydroxymethylpiperidin-1-yl; 3-hydroxypiperidin-1-yl; 4-methylpiperazin-1-yl; morpholin-4-yl; 3-oxopiperazin-1-yl;

$R^5O$, wherein $R^5$ is 2-allylphenyl; 4-chlorophenyl; ethyl; 2-fluorophenyl; 4-fluorophenyl; hydrogen; methyl; 4-nitrophenyl; and $R^6S$, wherein $R^6$ is 2-acetylaminophenyl; 3-acetylaminophenyl; 4-acetylaminophenyl; benzyl; 2,4-difluorophenyl; 3,4-difluorophenyl; 3,4-dimethoxyphenyl; 4-fluorobenzyl; 3-fluorophenyl; 2-methoxyphenyl; 3-methoxyphenyl; 1-methyl-1H-imidazol-2-yl; 2-(4-methylphenoxy)ethyl; 4-methylpyrimidin-2-yl; phenyl; pyridin-2-yl; pyridin-4-yl;

pharmaceutically acceptable salts, solvates, hydrates, geometrical isomers, tautomers, optical isomers, N-oxides and prodrug forms thereof.

Another object of the present invention is a method for the treatment or prevention of a disease or disorder by inhibition of the human 11-β-hydroxysteroid dehydrogenase type 1 enzyme, and to achieve immuno-modulation, said method comprising administering to a mammal, including a human, in need of such treatment an effective amount of a compound of any of the formulae described herein.

These compounds may also be used to manufacture a medicament for the prevention, management or treatment of a disease or disorder by inhibition of the human 11-β-hydroxysteroid dehydrogenase type 1 enzyme and to achieve immuno-modulation.

It is preferred that the medicament is intended for promoting wound healing.

It is preferred that the disease or disorder is selected from diabetes, syndrome X, obesity, glaucoma, hyperlipidemia, hyperglycemia, hyperinsulinemia, hypertension, osteoporosis, dementia, depression, and inflammatory disorders.

In one aspect of the invention, the said method is a method for the treatment or prophylaxis of a medical condition involving delayed or impaired wound healing. Examples of such medical conditions are diabetes, and conditions caused by treatment with steroids, in particular glucocorticoids. The method according to the invention is also intended for the promotion of wound healing in chronic wounds, such as diabetic ulcers, venous ulcers or pressure ulcers.

It is preferred that the immuno-modulation is done in the treatment or prevention of virus diseases, tuberculosis, lepra, and psoriasis.

It is preferred that T is selected from the group consisting of 2-acetylamino-4-methylthiazol-5-yl, 4-acetylphenyl, 4-benzoylaminophenyl, benzyl, 2,5-bis(2,2,2-trifluoroethoxy)phenyl, 3,5-bis(trifluoromethyl)phenyl, 5-bromo-6-chloropyridin-3-yl, 5-bromo-2-methoxyphenyl, 4-(3-chloro-2-cyanophenoxy)phenyl, 5-chloro-1,3-dimethyl-1H-pyrazol-4-yl, 3-chloro-5-fluoro-2-methylphenyl, 3-chloro-4-fluorophenyl, 3-chloro-4-methylphenyl, 4-chloro-3-nitrophenyl, 5-chloro-4-nitro-2-thienyl, 5-chlorothien-2-yl, 2-cyanophenyl, 3-cyanophenyl, 4-cyanophenyl, 3,5-dichloro-2-hydroxyphenyl, 2,6-dichlorophenyl, 4,5-dichloro-2-thienyl, 2,4-difluorophenyl, 2,6-difluorophenyl, 2,3-dihydro-1,4-benzodioxin-6-yl, 2,3-dihydro-1-benzofuran-5-yl, 3,4-dimethoxyphenyl, 5-(dimethylamino)-1-naphthyl, 1,2-dimethyl-1H-imidazol-4-yl, 3,5-dimethylisoxazol-4-yl, 5-fluoro-2-methylphenyl, 3-fluorophenyl, 4-(4-fluorophenylcarbonylamino)phenyl, 4-methoxy-2,3,6-trimethylphenyl, 4-methyl-3,4-dihydro-2H-1,4-benzoxazin-7-yl, 1-methyl-1H-imidazol-4-yl, 2-methyl-5-nitrophenyl, 3-(5-methyl-1,3,4-oxadiazol-2-yl)phenyl, 3-(2-methylpyrimidin-4-yl)phenyl, 5-[2-(methylthio)pyrimidin-4-yl]-2-thienyl, 5-methyl-2-(trifluoromethyl)-3-furyl, 4-morpholin-4-ylpyridin-3-yl, 1-naphthyl, 2-nitrophenyl, 3-nitrophenyl, 4-(1,3-oxazol-5-yl)phenyl, 2,2,4,6,7-pentamethyl-2,3-dihydro-1-benzofuran-5-yl, 6-phenoxypyridin-3-yl, 4-(phenylsulfonyl)-2-thienyl, 4-(1H-pyrazol-1-yl)phenyl, 5-pyridin-2-yl-2-thienyl, quinolin-8-yl, 4-tert-butylphenyl, 4-(1H-tetrazol-1-yl)phenyl, 2-thienyl, 3-(trifluoromethoxy)phenyl, 2-(trifluoromethyl)phenyl, and 1,3,5-trimethyl-1H-pyrazol-4-yl.

Preferred compounds are given above.

It is also preferred that T is 3-chloro-2-methylphenyl; with the proviso that when $R^1$ is hydrogen and $A_1$ is C—Z and $A_2$ is a nitrogen atom, Z is phenyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is hydrogen, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is methyl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is methyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is $CH_2$, Y is CO, $R^2$ is $R^5O$, $R^5$ is hydrogen, then T is not 3-chloro-2-methylphenyl;

$A_1$ is C—Z and $A_2$ is a nitrogen atom, X is $CH_2$, Y is CO, $R^2$ is $R^5O$, $R^5$ is methyl, then T is not 3-chloro-2-methylphenyl;

$A_1$ is C—Z and $A_2$ is a nitrogen atom, X is $CH_2$, Y is CO, $R^2$ is $R^5O$, $R^5$ is ethyl, then T is not 3-chloro-2-methylphenyl;

$A_1$ is C—Z and $A_2$ is a nitrogen atom, X is $CH_2$, Y is a single bond, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is CO, Y is CO, $R^2$ is $R^5O$, $R^5$ is ethyl, then T is not 3-chloro-2-methylphenyl.

Preferred compounds are given above.

It is also preferred that T is 4-phenoxyphenyl; with the proviso that when $R^1$ is hydrogen and $A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-phenoxyphenyl.

Preferred compounds are given above.

It is also preferred that T is selected from the group consisting of 4-[(1,3-benzothiazol-2-ylthio)acetylamino]phenyl, 1,1'-biphenyl-4-yl, 4-bromo-2-methylphenyl, 4-bromophenyl, 4-n-butoxyphenyl, 4-[(5-chloro-2-hydroxybenzyl)amino]phenyl, 4-chlorophenyl, 3,4-dichlorophenyl, 2,4-dichloro-6-methylphenyl, 4-fluorophenyl, 4-methylphenyl, 4-[(4-methylphthalazin-1-yl)amino]phenyl, 2-naphthyl, 4-nitrophenyl, 2,4,6-trichlorophenyl, 4-(trifluoromethoxy)phenyl, and 2,4,6-trimethylphenyl.

with the proviso that when $R^1$ is hydrogen and $A_1$ is C—Z and $A_2$ is a nitrogen atom, Z is phenyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ are both ethyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 1,1'-biphenyl-4-yl;

$A_1$ is a nitrogen atom and $A_2$ is C—Z, Z is phenyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ are both ethyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 4-bromo-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-bromo-2-methylphenyl;

$A_1$ is C—Z and $A_2$ is a nitrogen atom, Z is phenyl, then T is not 2,4-dichloro-6-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, Z is phenyl, then T is not 2,4-dichloro-6-methylphenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is C—Z and $A_2$ is a nitrogen atom, Z is phenyl, then T is not 2,4,6-trichlorophenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 2,4,6-trichlorophenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4,6-trichlorophenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 2,4,6-trichlorophenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4,6-trichlorophenyl;

$A_1$ is a nitrogen atom and $A_2$ is C—Z, Z is phenyl, then T is not 2,4,6-trichlorophenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 2,4,6-trichlorophenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 2,4,6-trichlorophenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 2,4,6-trichlorophenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4,6-trichlorophenyl.

Preferred compounds are given above, and also the following compounds:

4-methyl-N-(3-methyl-1,2,4-thiadiazol-5-yl)benzenesulfonamide;

N-(5-ethyl-1,3,4-thiadiazol-2-yl)-4-(trifluoromethoxy)benzenesulfonamide;

4-chloro-N-(5-isopropyl-1,3,4-thiadiazol-2-yl)benzenesulfonamide;

4-fluoro-N-[5-(trifluoromethyl)-1,3,4-thiadiazol-2-yl]benzenesulfonamide;

4-bromo-N-[5-(methoxymethyl)-1,3,4-thiadiazol-2-yl]benzenesulfonamide;

2-(1,3-benzothiazol-2-ylthio)-N-(4-{[(5-ethyl-1,3,4-thiadiazol-2-yl)amino]sulfonyl}phenyl)acetamide;

N-(5-methyl-1,3,4-thiadiazol-2-yl)-4-(trifluoromethoxy)benzenesulfonamide;

4-methyl-N-[5-(trifluoromethyl)-1,3,4-thiadiazol-2-yl]benzenesulfonamide;

4-chloro-N-[5-(trifluoromethyl)-1,3,4-thiadiazol-2-yl]benzenesulfonamide;

4-bromo-N-(5-phenyl-1,3,4-thiadiazol-2-yl)benzenesulfonamide;

4-bromo-N-(5-isopropyl-1,3,4-thiadiazol-2-yl)benzenesulfonamide;

N-[5-(4-methoxybenzyl)-1,3,4-thiadiazol-2-yl]-4-nitrobenzenesulfonamide;

3,4-dichloro-N-[5-(trifluoromethyl)-1,3,4-thiadiazol-2-yl]benzenesulfonamide;

4-fluoro-N-(5-isobutyl-1,3,4-thiadiazol-2-yl)benzenesulfonamide;

3,4-dichloro-N-(5-cyclopropyl-1,3,4-thiadiazol-2-yl)benzenesulfonamide;

4-bromo-N-[5-(trifluoromethyl)-1,3,4-thiadiazol-2-yl]benzenesulfonamide;

N-(5-cyclohexyl-1,3,4-thiadiazol-2-yl)-4-nitrobenzenesulfonamide;

N-(5-isobutyl-1,3,4-thiadiazol-2-yl)-4-methylbenzenesulfonamide;

N-(5-isobutyl-1,3,4-thiadiazol-2-yl)-4-nitrobenzenesulfonamide;

4-[(5-chloro-2-hydroxybenzyl)amino]-N-(5-ethyl-1,3,4-thiadiazol-2-yl)benzenesulfonamide;

4-chloro-N-[5-(4-chlorobenzyl)-1,3,4-thiadiazol-2-yl]benzenesulfonamide;

N-(5-cyclohexyl-1,3,4-thiadiazol-2-yl)-4-methylbenzenesulfonamide;

N-[5-(4-chlorobenzyl)-1,3,4-thiadiazol-2-yl]-4-nitrobenzenesulfonamide;

N-[5-(ethylthio)-1,3,4-thiadiazol-2-yl]-4-methylbenzenesulfonamide;

4-bromo-N-[5-(ethylthio)-1,3,4-thiadiazol-2-yl]benzene-sulfonamide;
N-(5-cyclohexyl-1,3,4-thiadiazol-2-yl)-4-fluorobenzene-sulfonamide;
4-chloro-N-(5-isobutyl-1,3,4-thiadiazol-2-yl)benzene-sulfonamide;
N-(5-cyclohexyl-1,3,4-thiadiazol-2-yl)-2,4,6-trimethyl-benzenesulfonamide;
4-chloro-N-(5-cyclohexyl-1,3,4-thiadiazol-2-yl)benzene-sulfonamide;
N-[5-(2,2-dimethylpropyl)-1,3,4-thiadiazol-2-yl]-4-nitrobenzenesulfonamide;
N-1,3-benzodioxol-5-yl-2-[(5-{[(4-methylphenyl)sulfonyl]amino}-1,3,4-thiadiazol-2-yl)thio]acetamide;
N-(5-ethyl-1,3,4-thiadiazol-2-yl)-4-[(4-methylphthalazin-1-yl)amino]benzenesulfonamide;
N-(5-isopropyl-1,3,4-thiadiazol-2-yl)-4-methylbenzene-sulfonamide.

In yet another aspect, the invention provides a method for the treatment of a human or animal subject suffering from a 11-β-hydroxysteroid dehydrogenase type I enzyme-related, such as diabetes, obesity, glaucoma, osteoporosis, cognitive disorders, immune disorders, hypertension, and wound healing, by administering a compound or composition delineated herein. The method can include administering to a subject (e.g., a human or an animal) in need thereof an effective amount of one or more compounds of any of the formulae herein, their salts, or compositions containing the compounds or salts.

Another aspect of the invention provides the use of the compounds according to any of the formulae herein for the manufacture of a medicament for the treatment of a disorder or condition, particularly 11-β-hydroxysteroid dehydrogenase type I enzyme-related disorder or condition, such as diabetes, obesity, glaucoma, osteoporosis, cognitive disorders, immune disorders, hypertension, and wound healing.

Another aspect of the invention provides methods for modulating 11-β-hydroxysteroid dehydrogenase type I enzyme function comprising contacting the receptor with an effective inhibitory amount of a compound according to any of the formulae herein.

The methods delineated herein can also include the step of identifying that the subject is in need of treatment of the 11-β-hydroxysteroid dehydrogenase type I enzyme-related disorder or condition. Identifying a subject in need of such treatment can be in the judgment of a subject or a health care professional and can be subjective (e.g., opinion) or objective (e.g., measurable by a test or diagnostic method).

This invention also features a method for preparing a composition. The method includes combining a compound of any of the formulae herein with a pharmaceutically acceptable carrier. The invention thus, envisions a pharmaceutical composition comprising at least one compound of any of the formulae described herein.

Still another aspect of the invention provides methods for the preparation of the compounds according to any of the formulae herein, including processes, reactions, reagents and intermediates specifically delineated herein.

A further aspect of the invention relates to a method for treating a disorder or condition, comprising administering to a subject in need thereof an effective amount of any of the formulae herein, wherein the disorder or condition is diabetes, obesity, glaucoma, osteoporosis, cognitive disorders, immune disorders, hypertension, or wound healing. The method can include administering to a subject (e.g., a human or an animal) in need thereof an effective amount of one or more compounds of any of the formulae herein, their salts, or compositions containing the compounds or salts.

A still further aspect of the invention relates to the use of the compounds of any of the formulae herein for the manufacture of a medicament for the treatment of disorders including diabetes, obesity, glaucoma, osteoporosis, cognitive disorders, immune disorders, hypertension, or wound healing.

Another object of the present invention is a pharmaceutical composition comprising at least one compound of formula as defined above, and a pharmaceutically acceptable carrier.

DETAILED DESCRIPTION OF THE INVENTION

The compounds according to the present invention may be used in several indications which involve 11-β-hydroxysteroid dehydrogenase type 1 enzyme. Thus, the compounds according to the present invention may be used against dementia (see WO97/07789), osteoporosis (see Canalis E 1996, Mechanisms of glucocorticoid action in bone: implications to glucocorticoid-induced osteoporosis, Journal of Clinical Endocrinology and Metabolism, 81, 3441–3447) and may also be used to address disorders in the immune system (see Franchimont et al, "Inhibition of Th1 immune response by glucocorticoids: dexamethasone selectively inhibits IL-12-induced Stat 4 phosphorylation in T lymphocytes", The Journal of Immunology 2000, Feb. 15, vol 164 (4), pages 1768–74) and also in the above listed indications.

The various terms used, separately and in combinations, in the above definition of the compounds having the formula (I) will be explained.

The term "aryl" in the present description refers to aromatic rings (monocyclic or bicyclic) having from 6 to 10 ring carbon atoms, such as phenyl (Ph) and naphthyl, which optionally may be substituted by $C_{1-6}$-alkyl. Examples of substituted aryl groups are benzyl, and 2-methylphenyl.

The term "heteroaryl" means in the present description a monocyclic, bi- or tricyclic aromatic ring system (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen or selenium and the remaining ring atoms are carbon. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, phthalimide, quinoline, quinoxaline, isoquinoline, phthalazine, cinnoline, quinazoline, indole, isoindole, indoline, isoindoline, benzothiophene, benzofuran, isobenzofuran, benzoxazole, 2,1,3-benzoxadiazole, benzothiazole, 2,1,3-benzothiazole, 2,1,3-benzoselenadiazole, benzimidazole, indazole, benzodioxane, indane, 1,2,3,4-tetrahydroquinoline, 3,4-dihydro-2H-1,4-benzoxazine, 2,3-dihydro-1,4-benzodioxine; 2,3-dihydro-1-benzofuran; 1,5-naphthyridine, 1,8-naphthyridine, acridine, fenazine and xanthene. Also encompassed by the present invention are heteroaryl rings substituted by $C_{1-6}$-alkyl, such as 1-methylimidazole, 5-methyl-1,3,4-oxadiazole, and 2-methylpyrimidine.

The term "heterocyclic" in the present description refers to unsaturated as well as partially and fully saturated mono-, bi- and tricyclic rings having from 4 to 14, preferably 4 to 10 ring atoms having one or more heteroatoms (e.g., oxygen, sulfur, or nitrogen) as part of the ring system and the reminder being carbon, such as, for example, the heteroaryl groups mentioned above as well as the corresponding partially saturated or fully saturated heterocyclic rings. Exemplary saturated heterocyclic rings are azetidine, pyrrolidine, piperidine, piperazine, morpholine, thiomorpholine and 1,4-oxazepane.

$C_{1-6}$-alkyl in the compound of formula (I) according to the present application, which may be straight or branched, is preferably $C_{1-4}$-alkyl. Exemplary alkyl groups include methyl, ethyl, n-propyl, isopropyl, n-butyl, sec-butyl, tert-butyl, pentyl, isopentyl, hexyl, isohexyl, and cyclohexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc.

$C_{1-6}$-amido refers to a group of the following: —N($C_{1-6}$-alkyl)—C(O)—$C_{1-6}$-alkyl in the compounds of formula (I) according to the present application, wherein the alkyl group may be straight or branched, is preferably $C_{1-4}$-alkyl. Exemplary alkyl groups include methyl, ethyl, n-propyl, isopropyl, n-butyl, sec-butyl, tert-butyl, pentyl, isopentyl, hexyl, isohexyl, and cyclohexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc.

$C_{3-6}$-cycloalkyl, in the compound of formula (I) according to the present invention, includes, but is not limited to cyclopropyl, cyclobutyl, cyclopentyl and cyclohexyl and includes $C_{1-6}$ alkyl substituents off of the cycloalkyl groups.

$C_{1-6}$-alkoxy, in the compound of formula (I) according to the present application may be straight or branched, is preferably $C_{1-4}$-alkoxy. Exemplary alkoxy groups include methoxy, ethoxy, propoxy, isopropoxy, butoxy, sec-butoxy, tert-butoxy, pentyloxy, isopentyloxy, hexyloxy, and isohexyloxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc.

$C_{1-6}$ acyl, in the compound of formula (I) according to the present application may be saturated or unsaturated and is preferably $C_{1-4}$-acyl. Exemplary acyl groups include formyl, acetyl, propionyl, butyryl, isobutyryl, valeryl, isovaleryl, butenoyl (e.g. 3-butenoyl), hexenoyl (e.g. 5-hexenoyl). For parts of the range "$C_{1-6}$-acyl" all subgroups thereof are contemplated such as $C_{1-5}$-acyl, $C_{1-4}$-acyl, $C_{1-3}$-acyl, $C_{1-2}$-acyl, $C_{2-6}$-acyl, $C_{2-5}$-acyl, $C_{2-4}$-acyl, $C_{2-3}$-acyl, $C_{3-6}$-acyl, $C_{4-5}$-acyl, etc.

$C_{2-6}$-alkenyl in the compound of formula (I) according to the present application, which may be straight, branched or cyclic, is preferably $C_{2-4}$-alkenyl. Exemplary alkenyl groups include vinyl, 1-propenyl, 2-propenyl, isopropenyl, 1-butenyl, 2-butenyl, 1-pentenyl, 2-pentenyl, 1-hexenyl, 2-hexenyl, and 1-cyclohexenyl. For parts of the range "$C_{2-6}$-alkenyl" all subgroups thereof are contemplated such as $C_{2-5}$-alkenyl, $C_{2-4}$-alkenyl, $C_{2-3}$-alkenyl, $C_{3-6}$-alkenyl, $C_{4-5}$-alkenyl, etc.

The term "halogen" in the present description refers to fluorine, chlorine, bromine and iodine.

The term "carbethoxy" in the present description refers to ethoxycarbonyl.

With the expression "mono- or di-substituted" is meant in the present description that the functionalities in question may be substituted with independently $C_{1-6}$-acyl, $C_{2-6}$-alkenyl, $C_{1-6}$-(cyclo)alkyl, aryl, arylcarbonyl, pyridylmethyl, or heterocyclic rings e.g. azetidine, pyrrolidine, piperidine, piperazine, morpholine and thiomorpholine, which heterocyclic rings optionally may be substituted with $C_{1-6}$-alkyl. The compounds according to the present invention may also be substituted by 4-(1,3-benzothiazol-2-ylthio)acetyl, 4-chloro-3-nitrophenylcarbonyl, [(4-chlorophenyl)amino]carbonyl, 2,4-dichlorophenoxyacetyl, [(4-fluorophenyl)amino]carbonothioyl, 4-fluorophenylcarbonyl, and 5-chloro-2-hydroxybenzyl. With the expression "optionally mono- or disubstituted" is meant in the present description that the functionalities in question may also be substituted with independently hydrogen.

Certain compounds of formula (I) are capable of existing in stereoisomeric forms including diastereomers and enantiomers and the invention extends to each of these stereoisomeric forms and to mixtures thereof including racemates. The different stereoisomeric forms may be separated from each other by conventional methods. Any given isomer may be obtained by stereospecific or asymmetric synthesis. The invention also extends to any tautomeric forms and mixtures thereof.

Compounds of formula (I) may also form solvates such as hydrates and the invention also extends to these forms. When referred to herein, it is understood that the term "compound of formula (I)" also includes these forms.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject for the treatment of disease, 11-β-HSD1 inhibition, 11-β-HSD1-mediated disease).

The term "prodrug forms" in the present description means a pharmacologically acceptable derivative, such as an ester or an amide, which derivative is biotransformed in the body to form the active drug (see Goodman and Gilman's, The Pharmacological basis of Therapeutics, $8^{th}$ ed., McGraw-Hill, Int. Ed. 1992, "Biotransformation of Drugs, p. 13–15).

"Pharmaceutically acceptable" means in the present description being useful in preparing a pharmaceutical composition that is generally safe, non-toxic and neither biologically nor otherwise undesirable and includes being useful for veterinary use as well as human pharmaceutical use.

"Pharmaceutically acceptable salts" mean in the present description salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, methanesulfonic acid, trifluoroacetic acid, fumaric acid, succinic acid, tartaric acid, citric acid, benzoic acid, ascorbic acid and the like. Base addition salts may be formed with organic and inorganic bases, such as sodium, ammonia, potassium, calcium, ethanolamine, diethanolamine, N-methylglucamine, choline and the like. Included in the invention are pharmaceutically acceptable salts or compounds of any of the formulae herein.

Pharmaceutical compositions according to the present invention contain a pharmaceutically acceptable carrier together with at least one of the compounds comprising the formula (I) as described herein above, dissolved or dispersed therein as an active, antimicrobial, ingredient. Such compositions are made by combining a compound of any of the formulae delineated herein with a pharmaceutically acceptable carrier, or alternatively multiple carriers. In a preferred embodiment, the therapeutic composition is not immunogenic when administered to a human patient for therapeutic purposes, unless that purpose is to induce an immune response.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient may be mixed with excipients, which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition may contain minor amounts of auxiliary substances such as wetting or emulsifying agents, pH buffering agents and the like which enhance the effectiveness of the active ingredient. Adjuvants may also be present in the composition.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerine, vegetable oils such as cottonseed oil, organic esters such as ethyl oleate, and water-oil emulsions.

The pharmaceutical composition according to one of the preferred embodiments of the present invention comprising compounds comprising the formula (I), may include pharmaceutically acceptable salts of that component therein as set out above. Pharmaceutically acceptable salts include the acid addition salts (formed with the free amino groups of the polypeptide) that are formed with inorganic acids such as, for example, hydrochloric or phosphoric acids, or such organic acids as acetic acid, tartaric acid, mandelic acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

The preparations according to the preferred embodiments may be administered orally, topically, intraperitoneally, intraarticularly, intracranially, intradermally, intramuscularly, intraocularly, intrathecally, intravenously, subcutaneously. Other routes are known to those of ordinary skill in the art.

The orally administrable compositions according to the present invention may be in the form of tablets, capsules, powders, granules, lozenges, liquid or gel preparations, such as oral, topical or sterile parenteral solutions or suspensions. Tablets and capsules for oral administration may be in unit dose presentation form and may contain conventional excipients such as binding agents, for example syrup, acacia, gelatin, sorbitol, traganath or polyvinyl-pyrrolidone; fillers e.g. lactose, sugar, maize-starch, calcium phosphate, sorbitol or glycine; tabletting lubricant e.g. magnesium stearate, talc, polyethylene glycol or silica; disintegrants e.g. potato starch, or acceptable wetting agents such as sodium lauryl sulfate. The tablets may be coated according to methods well known in normal pharmaceutical practice. Oral liquid preparations may be in the form of e.g. aqueous or oily suspensions, solutions, emulsions, syrups or elixirs or may be presented as a dry product for reconstitution with water or other suitable vehicle before use. Such liquid preparations may contain conventional additives such as suspending agents, e.g. sorbitol, syrup, methyl cellulose, glucose syrup, gelatin hydrogenated edible fats; emulsifying agents e.g. lecithin, sorbitan monooleate or acacia, non-aqueous vehicles (which may include edible oils), e.g. almond oil, fractionated coconut oil, oily esters such as glycerine, propylene glycol, or ethyl alcohol; preservatives e.g. methyl or propyl p-hydroxybenzoate or sorbic acid, and if desired conventional flavouring or colouring agents.

"An effective amount" refers to an amount of a compound which confers a therapeutic effect on the treated subject. The therapeutic effect may be objective (i.e., measurable by some test or marker) or subjective (i.e., subject gives an indication of or feels an effect). A pharmaceutical composition according to the present invention, may comprise typically an amount of at least 0.1 weight percent of compound comprising the formula (I) per weight of total therapeutic composition. A weight percent is a ratio by weight of total composition. Thus, for example, 0.1 weight percent is 0.1 grams of compound comprising the formula (I) per 100 grams of total composition. A suitable daily oral dose for a mammal, preferably a human being, may vary widely depending on the condition of the patient. However a dose of compound comprising the formula (I) of about 0.1 to 300 mg/kg body weight may be appropriate.

The compositions according to the present invention may also be used veterinarily and thus they may comprise a veterinarily acceptable excipient or carrier. The compounds and compositions may be thus administered to animals, e.g., cats, dogs, or horses, in treatment methods.

The compounds of the present invention in labelled form, e.g. isotopically labelled, may be used as a diagnostic agent. Examples of such labels are known in the art and include $^{131}I$, $^{35}S$, $^{32}P$, $^{18}F$, $^{14}C$, $^{11}C$, $^{3}H$, and the like.

This invention relates to methods of making compounds of any of the formulae herein comprising reacting any one or more of the compounds of the formulae delineated herein, including any processes delineated herein. The compounds of formula (I) above may be prepared by, or in analogy with, conventional methods, and especially according to or in analogy with the following methods. Further, the pharmacology in-vitro was studied using the following reagents and methods.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic*

*Synthesis*, John Wiley and Sons (1994); and L. Paquette, ed., *Encyclopedia of Reagents for Organic Synthesis*, John Wiley and Sons (1995) and subsequent editions thereof.

All publications mentioned herein are hereby incorporated by reference. By the expression "comprising" means "including but not limited to." Thus, other non-mentioned substances, additives or carriers may be present.

The invention will now be described in reference to the following Examples. These Examples are not to be regarded as limiting the scope of the present invention, but shall only serve in an illustrative manner.

EXAMPLES

The compounds of the present invention have been prepared using one of the following methodologies and each of the prepared substances have been named using the nomenclature software ACD 6.0.

Experimental Methods

Scintillation Proximity Assay

[1,2(n)-$^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma. The human 11-β-hydroxysteroid dehydrogenase type-1 enzyme (11-β-HSD1) was expressed in *Pichia pastoris*. 18-β-glycyrrhetinic acid (GA) was obtained from Sigma. The serial dilutions of the compounds were performed on a Tecan Genesis RSP 150. Compounds to be tested were dissolved in DMSO (1 mM) and diluted in 50 mM Tris-HCl, pH 7.2 containing 1 mM EDTA.

The multiplication of plates was done on a WallacQuadra. The amount of the product [$^3$H]-cortisol, bound to the beads was determined in a Packard, Top Count microplate liquid scintillation counter.

The 11-β-HSD$_1$ enzyme assay was carried out in 96 well microtiter plates (Packard, Optiplate) in a total well volume of 220 µL and contained 30 mM Tris-HCl, pH 7.2 with 1 mM EDTA, a substrate mixture tritiated Cortisone/NADPH (175 nM/181 µM), G-6-P (1 mM) and inhibitors in serial dilutions (9 to 0.15 µM). Reactions were initiated by the addition of human 11-β-HSD$_1$, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 µL 1 mM GA stop solution. Monoclonal mouse antibody was then added (10 µL of 4 µM) followed by 100 µL of SPA beads (suspended according to the manufacturers instructions). Appropriate controls were set up by omitting the 11-β-HSD$_1$ to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter.

The calculation of the $K_i$ values for the inhibitors was performed by use of Activity Base. The $K_i$ value is calculated from IC$_{50}$ and the $K_m$ value is calculated using the Cheng Prushoff equation (with reversible inhibition that follows the Michaelis-Menten equation): $K_i=IC_{50}(1+[S]/K_m)$ [Cheng, Y. C.; Prushoff, W. H. Biochem. Pharmacol. 1973, 22, 3099–3108]. The IC$_{50}$ is measured experimentally in an assay wherein the decrease of the turnover of cortisone to cortisol is dependent on the inhibition potential of each substance. The Ki values of the compounds of the present invention for the 11-β-HSD1 enzyme lie typically between about 10 nM and about 10 µM. Illustrative of the invention, the following Ki values have been determined in the human 11-β-HSD1 enzyme assay (see Table 1):

TABLE 1

Ki values determined in the human 11-β-HSD1 enzyme assay.

| Compound of Example | Ki(nM) |
|---|---|
| 80 | 321.06 |
| 244 | 218.95 |

Compound Preparation

General:

For preparative straight phase HPLC purification a Phenomenex column (250×21.1 mm, 10 µm) was used on a Gilson system eluting with ethanol in chloroform (gradient from 0–10% in 10 min) with a flow of 20 mL/min. Column chromatography was performed on silica using Silica gel 60 (230–400 mesh), Merck. Melting points were determined on a Gallenkamp apparatus. Elemental analyses were recorded using a Vario EL instrument. HPLC analyses were performed using a YMC ODS QA (33×3.0 mm, 3µ) with a flow of 1 mL/min on a Agilent 1100 system with monitoring at 215–395 nm. Reverse phase preparative HPLC was carried out on a 50×21.2 mm, 5µ YMC ODS QA column eluting with of mixture of acetonitrile and H$_2$O (0.1% TFA buffer) as eluent over 10 mins at a flow rate of 25 mL/min with the UV detector set at 254 and 220 nm. Thin layer chromatography was carried out using pre-coated silica gel F-254 plates (thickness 0.25 mm). Electrospray MS spectra were obtained on a Micromass platform LCMS spectrometer. Crude, worked up compounds were purified by flash column chromatography using pre packed silica SPE columns (10 g silica) on an Isco Foxy 200 Combiflash system, and a gradient of 16.67% ethyl acetate in hexane increasing incrementally to 100% ethyl acetate.

List of Abbreviations

ACN=acetonitrile
AIBN=azobisisobutyronitrile
Boc=tert-butoxycarbonyl
DCM=dichloromethane
DIEA=N,N-diisopropylethylamine
DMAP=4-dimethylaminopyridine
DME=ethyleneglycol dimethyl ether
DMF=dimethylformamide
DMSO=dimethyl sulfoxide
EDCI=1-(3-dimethylaminopropyl)-3-ethylcarbodiimide hydrochloride
EDTA=ethylenediaminetetraacetic acid
HCOOH=formic acid
HOAT=1-hydroxy-7-azabenzotriazole
HOBT=1-hydroxybenzotriazole hydrate
MTBE=tert-butyl methyl ether
NBS=N-bromosuccinimide
NMM=N-methylmorpholine
Py=pyridine
TEA=triethylamine
TFA=trifluoroacetic acid
THF=tetrahydrofuran
Sulfonamide Couplings Method A 1 equivalent (eq) of the heterocyclic compound (i.e., a 1,2,4-thiadiazole or 1,3,4-thiadiazole derivative) with an exocyclic amino group was dissolved in pyridine (0.5 M solution). The sulfonyl chloride (1.2 eq) was added and the reaction mixture was heated to 80° C. for 1–3 hours. Alternatively, the reaction mixture was heated in a microwave oven at 150° C. for 5–20 min. The reaction mixture was poured into aqueous HCl (1 M). If the product precipitated it was collected on a filter and washed with aqueous HCl (1 M) and recrystallised from ethanol. In case an oil was obtained, the crude was extracted with DCM and worked up and purified using standard procedures.

Method B

A solution of the heterocyclic compound (i.e., a 1,2,4-thiadiazole or 1,3,4-thiadiazole derivative) with an exocyclic amino group (1 eq), triethylamine (2 eq) and DMAP (1 eq) in DMF (1 M) and DCM (0.225 M) was dispensed into a reaction vial. The sulfonyl chloride (1.2 eq) was dissolved in DCM (0.33 M) and added. The reaction mixture was kept at room temperature over-night. The mixture was then added to petroleum ether (10 times reaction volume). After some hours in the refrigerator the supernatant was decanted and the residual material purified using standard procedures.

Method C 1 eq of the heterocyclic compound (i.e., a 1,2,4-thiadiazole or 1,3,4-thiadiazole derivative) with an exocyclic amino group was dissolved in THF. 1.8 eq of the sulfonyl chloride were then added in dry THF. 5 eq of NaH were added and the reaction left at room temperature for 24 hours. The reaction was quenched with. The reaction was worked up and purified using standard procedures.

Amide Couplings

Method D 5-(Arylsulfonylamino)-1,2,4-thiadiazole-3-carboxylic acid (1.5 mmol) was suspended in 10 ml $SOCl_2$ and heated to 70° C. for 2 hours. The solvent was removed by evaporation. The remaining solid was suspended in DCM, treated with an excess of amine and left for 10–30 minutes before the solvent was removed. The product was purified using standard procedures.

Thioether Oxidations

Method E

The preparation of 3-chloro-2-methyl-N-{3-[(phenylsulfonyl)methyl]-1,2,4-thiadiazol-5-yl}benzenesulfonamide (Example 60) is representative of this procedure.

3-Chloro-2-methyl-N-{3-[(phenylthio)methyl]-1,2,4-thiadiazol-5-yl}benzenesulfonamide was dissolved in diethyl ether and acetonitrile. m-Chloroperbenzoic acid (2 eq) was added and the reaction mixture was stirred at room temperature for 3 hours. The reaction mixture was washed with water. Standard purification techniques were employed to yield the desired sulfone.

Preparation of Starting Amines

Aminothiadiazole which were not available commercially were prepared using one of the following procedures.

The preparation of thiadiazolyl (lower) alkanoic acid derivatives is described in Teraji, Tsutomu; Sakane, Kazuo; Goto, Jiro. (Fujisawa Pharmaceutical Co., Ltd., Japan). Brit. UK Pat. Appl. (1981), 13 pp. CODEN: BAXXDU GB 2068361 A 19810812 Application: GB 79-44603 19791231. CAN 96:142862 AN 1982:142862.

Furthermore, N-protected methyl(5-amino-1,2,4-thiadiazol-3-yl)acetate was prepared as described in Tet. Lett. 1993, 34(40), 6423–6426. This document describes the preparation of a compound of formula (IV):

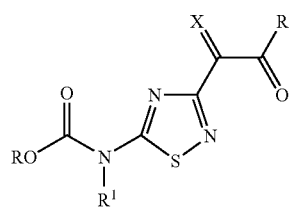

wherein:
either R'=H, X=$H_2$, and R=Me; or
R'=OMe, X=O, NOH or NOMe, and R=Me, Et, Bn or Ph.

After removal of the protecting group on the exocyclic amino group, the resulting products may be reacted e.g., as described in the sulfonamide couplings mentioned above. Furthermore, when R'=H, X=$H_2$, and R=Me reductive amination of the aldehyde can be carried out prior to deprotection so as to yield thiadiazoles of formula (V):

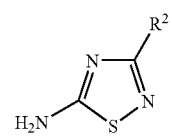

wherein:
$R^2$ is a secondary or tertiary 2-aminoethyl substituent.

Methyl 5-amino-1,2,4-thiadiazole-3-carboxylate was prepared from 5-amino-3-methyl-1,2,4-thiadiazole which is commercially available from Fluorochem according to the following procedure. Protection of the amino group of 5-amino-3-methyl-1,2,4-thiadiazole with a tert-butoxycarbonyl group using standard procedures gave the corresponding carbamate which was dissolved in 15% NaOH (aq) and heated to 70° C. 4 eq of $KMnO_4$ were slowly added and the reaction was heated to reflux (105° C.) for 2 hours. The reaction was cooled to room temperature and filtered through CELITE. 12M HCl was then added until pH~2 was obtained. The reaction was worked up and purified using standard procedures. The carbamate was then dissolved in MeOH and HCl (g) was added for 3 minutes at 0° C. The bottle was stoppered and the reaction was left for 1 hour at room temperature. The solvent was removed by evaporation to give the desired amino ester which was subsequently used in sulfonamide coupling reactions using method C to afford the relevant 5-(arylsulfonylamino)-1,2,4-thiadiazole-3-carboxylic acid.

A number of 5-amino-1,2,4-thiadiazoles of formula (V) were prepared from the corresponding amidines.

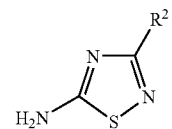

wherein:
$R^2$=tButyl, cyclopropyl, 3-thienyl, morpholin-4-yl, or 3-furyl.

The salt of the amidine was suspended in 20 ml DCM and 1 eq perchloromethyl mercaptan in DCM was added at 0° C. 5M NaOH (aq) was then slowly added and the reaction was left at 0° C. for 2 hours. DCM and H₂O were added and the reaction was extracted. The organic layer was washed with H₂O, dried (MgSO₄) and evaporated. This product was then dissolved in EtOH and of conc. NH₃ (aq) was added. The reaction was put in the microwave oven for 25 min at 150° C. H₂O was added and the product extracted with EtOAc, dried MgSO₄, and evaporated. The product was dissolved in Et₂O (alt. THF/Et₂O, 1/10) and HCl in Et₂O was added. The salt of the aminothiadiazole was collected by filtration.

A number of 5-amino-1,2,4-thiadiazoles were prepared through the elaboration of commercially available 3-alkyl-5-amino-1,2,4-thiadiazoles. In this respect two alternative strategies were employed. In both cases the amine was protected with a tert-butoxycarbonyl group using standard procedures prior to further elaboration.

Firstly, bromination of the alkyl substituent α to the thiadiazole ring gave a species which could be reacted with a range of nucleophiles including cyanide, alcohols and thiols. The preparation of 3-{1-[(3-fluorophenyl)thio]ethyl}-1,2,4-thiadiazol-5-amine trifluoroacetate illustrates this procedure.

3-Ethyl-5-amino-1,2,4-thiadiazole, 1.1 eq NBS and a small amount of AIBN were dissolved in CCl₄ and refluxed at 80° C. over-night. Standard work up followed by purification on silica gel with DCM as mobile phase gave the 3-(1-bromoethyl)-5-amino-1,2,4-thiadiazole. Subsequently, 0.9 eq of NaI were dissolved in dry acetone and 3-(1-bromoethyl)-5-amino-1,2,4-thiadiazole. 1 eq of Na₂CO₃ and 1 eq of 3-fluorothiophenol were then added and the reaction was stirred at room temperature over-night. The reaction was quenched with water and worked up and purified using standard procedures.

Secondly, lithiation and subsequent trapping with an electrophile gave extended functional groups at the 3-position. The preparation of 5-amino-3-(2-hydroxypropyl)-1,2,4-thiadiazole is representative of this procedure.

Di-tert-butyl dicarbonate (1.1 eq) and DMAP (0.1 eq) were added to a 0.3M solution of 5-amino-3-methyl-1,2,4-thiadiazole in tert-butanol and the mixture heated at 40° C. for 30 minutes. The reaction mixture was allowed to stir further at room temperature overnight. Standard work-up protocols yielded the desired Boc protected aminothiadiazole. 1.1 eq of n-BuLi were carefully added via a syringe to a precooled solution (−78° C.) of diisopropylamine (4 eq) in dry THF. A solution of tert-Butyl(3-methyl-1,2,4-thiadiazol-5-yl)carbamate (1 eq) in dry THF (3 mL) was added slowly and the clear solution turned yellow. After 15 min a solution of acetaldehyde (4 eq) in dry THF was added and the yellow mixture became colourless. The reaction mixture was allowed to stir at room temperature overnight. Standard work up and purification gave tert-butyl(3-methyl-1,2,4-thiadiazol-5-yl)carbamate.

3-Arylthiomethyl-5-amino-1,2,4-thiadiazoles were prepared from the corresponding dichlorothiadiazole which is commercially available from Maybridge.

1.05 eq of NaI were dissolved in dry acetone. 1 eq of 5-chloro-3-(chloromethyl)-1,2,4-thiadiazole, 1.03 eq of the thiophenol and 1 eq of Na₂CO₃ were added and the reaction mixture was stirred at ambient temperature for 2 hours. The reaction mixture was diluted with EtOAc and water. The organic phase was washed with an aqueous solution of Na₂SO₃ (sat), dried over MgSO₄ and evaporated in vacuo. Preparative HPLC purification gave the 5-chloro-3-[(phenylthio)methyl]-1,2,4-thiadiazole. This was subsequently dissolved in 95% ethanol and conc. NH₃ (aq) was added. In some cases acetonitrile was added in order to completely dissolve the starting material. The mixture was transferred to a microwave tube and run in the microwave at 150° C. for 5 min. the reaction was quenched with water and the desired 3-arylthiomethyl-5-amino-1,2,4-thiadiazole worked up and purified using standard procedures.

Compounds encompassed by formula (VI):

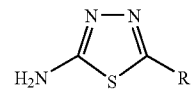

VI were prepared through the reaction of thiosemicarbazide with the relevant acid chloride (RCOCl).

The preparation of ethyl 2-amino-1,3,4-thiadiazole-5-acetate is representative of this procedure and is described in *J. Am. Chem. Soc.* 1946, 68, 96–99, as well as a number of other publications.

The following compounds were prepared except for the following Examples:

Example 230 and 241 (commercially available from Asinex)

Example 191, 200, 207, 210, 224 and 278 (commercially available from Bionet)

Examples 190, 192, 198, 204, 212, 216, 219, 220, 226, 234–237, 239, 242, 245, 251, 256, 261–263, 266, 281 and 284 (commercially available from Chembridge)

Examples 189, 206, 231 and 274 (commercially available from Maybridge)

Examples 202, 214, 238, 275, 276 and 280 (commercially available from Vitas)

Example 283 (commercially available from Sigma)

Example 193 (commercially available)

Sulfonyl Chlorides

Arylsulfonyl chlorides that were not commercially available were prepared from the aniline derivatives according to literature procedures (see for instance: Hoffman, R. V. (1981) *Org. Synth.* 60: 121).

EXAMPLES

Example 1

N-(3-isopropyl-1,2,4-thiadiazol-5-yl)quinoline-8-sulfonamide

Prepared using method A.

1H NMR (400 MHz, METHANOL-D4) δ ppm 1.26 (d, J=6.84 Hz, 6H) 2.95 (m, 1H) 7.73 (dd, J=8.18, 4.52 Hz, 1H) 7.78 (t, J=7.81 Hz, 1H) 8.27 (d, J=8.06 Hz, 1H) 8.52 (dd, J=7.32, 0.98 Hz, 1H) 8.63 (d, J=7.32 Hz, 1H) 8.96 (d, J=3.42 Hz, 1H); MS (ES+) m/z 335 (M+H⁺)

Example 2

3-cyano-N-(3-ethyl-1,2,4-thiadiazol-5-yl)benzenesulfonamide

Prepared using method C.

1H NMR (400 MHz, CHLOROFORM-D) δ ppm 1.34 (t, J=7.45 Hz, 2H) 2.82 (q, J=7.57 Hz, 2H) 7.63 (t, J=7.81 Hz, 1H) 7.84 (d, J=7.81 Hz, 1H) 8.12 (m, J=11.23 Hz, 2H); MS (ES+) m/z 295 (M+H⁺)

Example 3

N-(3-isopropyl-1,2,4-thiadiazol-5-yl)-3-(2-methylpyrimidin-4-yl)benzenesulfonamide Prepared using method A.
1H NMR (400 MHz, METHANOL-D4) δ ppm 1.27 (d, J=6.84 Hz, 6H) 2.79 (s, 3H) 2.95 (m, 1H) 7.71 (t, J=7.93 Hz, 1H) 7.91 (d, J=5.62 Hz, 1H) 8.05 (d, J=8.30 Hz, 1H) 8.39 (d, J=7.81 Hz, 1H) 8.70 (s, 1H) 8.77 (d, J=5.62 Hz, 1H); MS (ES+) m/z 376 (M+H$^+$)

Example 4

N-(3-isopropyl-1,2,4-thiadiazol-5-yl)-1,3,5-trimethyl-1H-pyrazole-4-sulfonamide

Prepared using method A.
1H NMR (400 MHz, CHLOROFORM-D) δ ppm 1.33 (d, J=7.08 Hz, 6H) 2.39 (m, 3H) 2.51 (m, 3H) 3.07 (m, 1H) 3.76 (m, 3H) MS m/z 316 (M+H)$^+$

Example 5

4-nitro-N-(3-phenyl-1,2,4-thiadiazol-5-yl)benzenesulfonamide

Prepared using method C.
1H NMR (270 MHz, DMSO-D6) δ ppm 7.42 (m, 3H) 8.02 (m, 4H) 8.30 (d, J=8.97 Hz, 2H). MS (ESI+) m/z 363 (M+H)$^+$.

Example 6

N-(3-isopropyl-1,2,4-thiadiazol-5-yl)-3,5-dimethyl-isoxazole-4-sulfonamide

Prepared using method A.
1H NMR (400 MHz, METHANOL-D4) δ ppm 1.28 (d, J=6.84 Hz, 6H) 2.35 (s, 3H) 2.63 (s, 3H) 2.96 (m, 1H); MS (ES+) m/z 303 (M+H$^+$)

Example 7

Ethyl 1-[(5-{[(3-chloro-2-methylphenyl)sulfonyl]amino}-1,2,4-thiadiazol-3-yl)carbonyl]piperidine-4-carboxylate Prepared using method D.
1H NMR (400 MHz, CHLOROFORM-D) δ ppm 1.20 (t, J=7.08 Hz, 3H) 1.71 (m, 2H) 1.96 (m, 2H) 2.57 (m, 1H) 2.66 (s, 3H) 3.01 (m, 1H) 3.35 (m, 1H) 4.10 (q, J=7.08 Hz, 2H) 4.29 (m, 1H) 4.60 (m, J=12.70 Hz, 1H) 7.19 (t, J=7.93 Hz, 1H) 7.50 (d, J=8.06 Hz, 1H) 7.89 (d, J=7.93 Hz, 1H). MS (ESI+) m/z 473 (M+H)$^+$

Example 8

5-{[(3-chloro-2-methylphenyl)sulfonyl]amino}-N-methyl-1,2,4-thiadiazole-3-carboxamide Prepared using method D.
1H NMR (400 MHz, DMSO-D6) δ ppm 2.60 (s, 3H) 2.72 (d, J=4.64 Hz, 3H) 7.39 (t, J=7.93 Hz, 1H) 7.70 (d, J=8.06 Hz, 1H) 7.88 (d, J=8.06 Hz, 1H) 8.82 (s br, 1H). MS (ESI+) m/z 347 (M+H)$^+$

Example 9

N-(3-tert-butyl-1,2,4-thiadiazol-5-yl)-3-cyanobenzenesulfonamide

Prepared using method C.
1H NMR (400 MHz, DMSO-D6) δ ppm 1.25 (s, 9H) 7.78 (t, J=7.81 Hz, 1H) 8.12 (m, J=8.06 Hz, 2H) 8.22 (s, 1H). MS (ESI+) m/z 323 (H+1)

Example 10

N-(3-ethyl-1,2,4-thiadiazol-5-yl)-5-fluoro-2-methylbenzenesulfonamide

Prepared using method C.
1H NMR (400 MHz, CHLOROFORM-D) δ ppm 1.31 (t, J=7.45 Hz, 3H) 2.49 (s, 3H) 2.81 (q, J=7.41 Hz, 2H) 7.14 (td, J=8.06, 2.69 Hz, 1H) 7.22 (d, J=5.13 Hz, 1H) 7.72 (dd, J=8.42, 2.56 Hz, 1H); MS (ES+) m/z 302 (M+H$^+$)

Example 11

N-(3-isopropyl-1,2,4-thiadiazol-5-yl)-1-methyl-1H-imidazole-4-sulfonamide

Prepared using method A.
1H NMR (400 MHz, METHANOL-D4) δ ppm 1.28 (d, J=7.08 Hz, 6H) 2.97 (m, 1H) 3.81 (s, 3H) 7.82 (s, 1H) 8.09 (s, 1H); MS (ES+) m/z 288 (M+H$^+$)

Example 12

N-(3-isopropyl-1,2,4-thiadiazol-5-yl)-1-phenyl-methanesulfonamide

Prepared using method A.
1H NMR (400 MHz, CHLOROFORM-D) δ ppm 1.22 (d, J=7.08 Hz, 6H) 2.90 (m, 1H) 4.32 (m, 2H) 7.27 (m, 3H) 7.36 (m, 2H) MS m/z 298 (M+H)$^+$

Example 13

3-chloro-4-methyl-N-(3-phenyl-1,2,4-thiadiazol-5-yl)benzenesulfonamide

Prepared using method C.
1H NMR (270 MHz, DMSO-D6) δ ppm 2.31 (s, 3H) 7.39 (m, 4H) 7.59 (dd, J=7.92, 1.58 Hz, 1H) 7.69 (d, J=1.58 Hz, 1H) 8.01 (dd, J=7.52, 2.24 Hz, 2H). MS (ESI+) m/z 366 (M+H)$^+$.

Example 14

N-(3-methoxy-1,2,4-thiadiazol-5-yl)-4-methylbenzenesulfonamide

Prepared using method C.
1H NMR (400 MHz, METHANOL-D4) δ ppm 2.40 (s, 3H) 3.98 (s, 3H) 7.34 (d, J=8.06 Hz, 2H) 7.74 (d, J=8.30 Hz, 2H); MS [M+H]$^+$ m/z=286.

Example 15

5-{[(3-chloro-2-methylphenyl)sulfonyl]amino}-1,2,4-thiadiazole-3-carboxamide

Prepared using method D with ammonia as the amine.
1H NMR (400 MHz, CHLOROFORM-D) δ ppm 3.21 (s, 3H) 7.76 (t, J=7.93 Hz, 1H) 8.07 (d, J=7.81 Hz, 1H) 8.45 (d, J=8.06 Hz, 1H). MS (ESI+) m/z 333 (M+H)$^+$

Example 16

5-{[(3-chloro-2-methylphenyl)sulfonyl]amino}-1,2,4-thiadiazole-3-carboxylic acid Prepared using method C.
1H NMR (400 MHz, DMSO-D6) δ ppm 2.62 (s, 3H) 7.40 (t, J=7.93 Hz, 1H) 7.71 (d, J=8.06 Hz, 1H) 7.88 (d, J=7.81 Hz, 1H). MS (ESI+) m/z 334 (M+H)$^+$

Example 17

(R)-N-(4-{[1-(5-{[(4-phenoxyphenyl)sulfonyl]amino}-1,2,4-thiadiazol-3-yl)ethyl]thio}phenyl)acetamide Prepared using method A.
1H NMR (400 MHz, CHLOROFORM-D) δ ppm 1.57 (d, J=6.84 Hz, 3H) 2.16 (m, 3H) 4.27 (dt, J=7.32, 6.84 Hz, 1H) 7.00 (m, 4H) 7.19 (m, 3H) 7.39 (m, 4H) 7.82 (m, 2H) 7.94 (m, 1H) 10.30 (m, 1H) MS m/z 527 (M+H)$^+$

Example 18

Ethyl 5-{[(4-bromo-2-methylphenyl)sulfonyl]amino}-1,2,4-thiadiazole-3-carboxylate Prepared using method B.
1H NMR (270 MHz, METHANOL-D4) δ ppm 1.37 (t, J=7.13 Hz, 3H) 2.62 (s, 3H) 4.39 (q, J=6.86 Hz, 2H) 7.51 (m, 1H) 7.56 (m, 1H) 7.85 (d, J=8.44 Hz, 1H). MS (ESI+) m/z 406 (M+H)$^+$.

Example 19

N-(5-{[(3-isopropyl-1,2,4-thiadiazol-5-yl)amino]sulfonyl}-4-methyl-1,3-thiazol-2-yl)acetamide Prepared using method A.
1H NMR (400 MHz, CHLOROFORM-D) δ ppm 1.33 (d, J=7.08 Hz, 6H) 2.33 (m, 3H) 2.52 (m, 3H) 3.12 (m, 1H) MS m/z 362 (M+H)$^+$

Example 20

3-chloro-2-methyl-N-{3-[(4-methylpiperazin-1-yl)carbonyl]-1,2,4-thiadiazol-5-yl}benzenesulfonamide Prepared using method D.
1H NMR (400 MHz, DMSO-D6) δ ppm 2.62 (s, 3H) 2.82 (s, 3H) 3.07 (s br, 3H) 3.40 (s br, 3H) 4.19 (s br, 1H) 4.48 (s br, 1H) 7.34 (t, J=7.93 Hz, 1H) 7.62 (d, J=7.81 Hz, 1H) 7.86 (d, J=7.81 Hz, 1H). MS (ESI+) m/z 416 (M+H)$^+$

Example 21

N-(3-isopropyl-1,2,4-thiadiazol-5-yl)-3-(5-methyl-1,3,4-oxadiazol-2-yl)benzenesulfonamide Prepared using method A.
1H NMR (400 MHz, METHANOL-D4) δ ppm 1.26 (d, J=7.08 Hz, 6H) 2.63 (s, 3H) 2.95 (m, 1H) 7.73 (t, J=7.81 Hz, 1H) 8.06 (d, J=7.81 Hz, 1H) 8.21 (d, J=7.81 Hz, 1H) 8.46 (s, 1H); MS (ES+) m/z 366 (M+H$^+$)

Example 22

3-cyano-N-(3-isopropyl-1,2,4-thiadiazol-5-yl)benzenesulfonamide

Prepared using method A.
1H NMR (400 MHz, METHANOL-D4) δ ppm 1.27 (d, J=6.84 Hz, 6H) 2.95 (m, 1H) 7.72 (t, J=7.93 Hz, 1H) 7.95 (d, J=7.81 Hz, 1H) 8.14 (d, J=7.81 Hz, 1H) 8.18 (s, 1H); MS (ES+) m/z 309 (M+H$^+$)

Example 23

2-cyano-N-(3-isopropyl-1,2,4-thiadiazol-5-yl)benzenesulfonamide

Prepared using method A.
1H NMR (400 MHz, METHANOL-D4) δ ppm 1.25 (d, J=6.84 Hz, 6H) 2.94 (m, 1H) 7.72 (td, J=7.57, 1.22 Hz, 1H) 7.79 (td, J=7.81, 1.22 Hz, 1H) 7.91 (dd, J=7.57, 0.98 Hz, 1H) 8.11 (d, J=7.81 Hz, 1H); MS (ES+) m/z 309 (M+H$^+$)

Example 24

5-bromo-N-(3-isopropyl-1,2,4-thiadiazol-5-yl)-2-methoxybenzenesulfonamide

Prepared using method A.
1H NMR (400 MHz, METHANOL-D4) δ ppm 1.30 (d, J=7.08 Hz, 6H) 2.98 (m, 1H) 3.78 (s, 3H) 7.09 (d, J=8.79 Hz, 1H) 7.67 (dd, J=8.79, 2.44 Hz, 1H) 7.96 (d, J=2.44 Hz, 1H); MS (ES+) m/z 392 (M+H$^+$)

Example 25

N-(3-isopropyl-1,2,4-thiadiazol-5-yl)-6-morpholin-4-ylpyridine-3-sulfonamide

Prepared using method A.
1H NMR (400 MHz, CHLOROFORM-D) δ ppm 1.31 (m, 6H) 3.05 (m, 1H) 3.81 (m, 8H) 6.93 (m, 1H) 7.99 (dd, J=9.52, 2.20 Hz, 1H) 8.50 (d, J=2.20 Hz, 1H) 11.29 (m, 1H) MS m/z 370 (M+H)$^+$

Example 26

4-chloro-N-(3-phenyl-1,2,4-thiadiazol-5-yl)benzenesulfonamide

Prepared using method C.
1H NMR (270 MHz, DMSO-D6) δ ppm 7.37 (m, 3H) 7.49 (m, 2H) 7.75 (m, 2H) 8.01 (m, 2H). MS (ESI+) m/z 352 (M+H)$^+$.

Example 27

3-chloro-N-[3-(3-furyl)-1,2,4-thiadiazol-5-yl]-2-methylbenzenesulfonamide

Prepared using method C.
1H NMR (400 MHz, DMSO-D6) δ ppm 2.65 (s, 3H) 6.93 (d, J=1.22 Hz, 1H) 7.40 (t, J=7.93 Hz, 1H) 7.70 (d, J=7.81 Hz, 1H) 7.83 (s, 1H) 7.90 (d, J=7.32 Hz, 1H) 8.33 (s, 1H); MS [M+H]$^+$ m/z=356.

Example 28

N-(3-isopropyl-1,2,4-thiadiazol-5-yl)-3-(trifluoromethoxy)benzenesulfonamide

Prepared using method A.
1H NMR (400 MHz, METHANOL-D4) δ ppm 1.28 (d, J=6.84 Hz, 6H) 2.97 (m, 1H) 7.47 (t, J=7.32 Hz, 2H) 7.69 (t, J=7.93 Hz, 1H) 8.07 (d, J=8.30 Hz, 1H); MS (ES+) m/z 368 (M+H$^+$)

Example 29

N-(3-isopropyl-1,2,4-thiadiazol-5-yl)thiophene-2-sulfonamide

Prepared using method A.
1H NMR (400 MHz, CHLOROFORM-D) δ ppm 1.33 (d, J=6.84 Hz, 6H) 3.27 (m, 1H) 7.05 (m, 1H) 7.54 (m, 1H) 7.65 (m, 1H) MS m/z 290 (M+H)$^+$

Example 30

5-chloro-N-(3-isopropyl-1,2,4-thiadiazol-5-yl)-1,3-dimethyl-1H-pyrazole-4-sulfonamide Prepared using method A.
1H NMR (400 MHz, CHLOROFORM-D) δ ppm 1.32 (m, 6H) 2.41 (m, 3H) 3.17 (m, 1H) 3.79 (m, 3H) MS m/z 336 (M+H)$^+$

Example 31

N-(3-morpholin-4-yl-1,2,4-thiadiazol-5-yl)-4-phenoxybenzenesulfonamide

Prepared using method C.
1H NMR (400 MHz, CHLOROFORM-D) δ ppm 3.47 (m, 4H) 3.73 (m, 4H) 6.97 (d, J=8.79 Hz, 2H) 7.04 (d, J=8.55 Hz, 2H) 7.21 (t, J=7.45 Hz, 1H) 7.39 (t, J=7.45 Hz, 2H) 7.84 (d, J=8.79 Hz, 2H). MS (ESI+) m/z 419 (H+1)

Example 32

3-chloro-N-(3-{[3-(hydroxymethyl)piperidin-1-yl]carbonyl}-1,2,4-thiadiazol-5-yl)-2-methylbenzenesulfonamide Prepared using method D.
1H NMR (400 MHz, CHLOROFORM-D) δ ppm 1.63 (m, 5H) 2.66 (s, 3H) 3.02 (m, 1H) 3.32 (m, 1H) 3.55 (m, 2H) 4.41 (m, 1H) 4.71 (m, 1H) 7.24 (m, 1H) 7.56 (m, 1) 7.96 (m, 1H). MS (ESI+) m/z 431 (M+H)$^+$

Example 33

N-(3-isopropyl-1,2,4-thiadiazol-5-yl)-4-methyl-3,4-dihydro-2H-1,4-benzoxazine-7-sulfonamide Prepared using method A.
1H NMR (400 MHz, METHANOL-D4) δ ppm 1.27 (d, J=6.84 Hz, 6H) 2.90 (s, 3H) 2.94 (m, 1H) 3.28 (m, J=4.64 Hz, 2H) 4.30 (m, 2H) 6.76 (d, J=8.79 Hz, 1H) 710 (d, J=7.08 Hz, 1H) 7.11 (s, 1H); MS (ES+) m/z 355 (M+H$^+$)

Example 34

3-chloro-2-methyl-N-[3-(morpholin-4-ylmethyl)-1,2,4-thiadiazol-5-yl]benzenesulfonamide trifluoroacetate Prepared using method C.
1H NMR (400 MHz, METHANOL-D4) δ ppm 2.70 (s, 3H), 3.30–3.40 (m, disturbed by solvent peak, 4H), 3.89 (m, 4H), 4.28 (s, 2H), 7.31 (t, J=8.06 Hz, 1H), 7.61 (d, J=8.06 Hz, 1H), 7.96 (d, J=8.06 Hz, 1H); MS [M+H]$^+$ m/z=389.

Example 35

5-chloro-N-(3-phenyl-1,2,4-thiadiazol-5-yl)thiophene-2-sulfonamide

Prepared using method C.
1H NMR (270 MHz, DMSO-D6) δ ppm 7.04 (d, J=3.96 Hz, 1H) 7.26 (d, J=3.96 Hz, 1H) 7.40 (m, 3H) 8.04 (dd, J=7.52, 1.98 Hz, 2H). MS (ESI+) m/z 358 (M+H)$^+$.

Example 36

4-chloro-3-nitro-N-[3-(2-thienyl)-1,2,4-thiadiazol-5-yl]benzenesulfonamide

Prepared using method C.
1H NMR (400 MHz, DMSO-D6) δ ppm 7.20 (dd, J=5.01, 3.78 Hz, 1H) 7.80 (dd, J=3.78, 1.10 Hz, 1H) 7.82 (dd, J=5.07, 1.16 Hz, 1H) 7.96 (d, J=8.42 Hz, 1H) 8.11 (dd, J=8.54, 2.20 Hz, 1H) 8.47 (d, J=2.08 Hz, 1H). MS (ESI+) m/z 403 (H+1)

Example 37

3-chloro-2-methyl-N-(3-methyl-1,2,4-thiadiazol-5-yl)benzenesulfonamide

Prepared using method C.
1H NMR (270 MHz, CHLOROFORM-D) δ ppm 2.50 (s, 3H) 2.60 (s, 3H) 7.25 (m, 1H) 7.57 (d, J=7.92 Hz, 1H) 7.95 (d, J=7.92 Hz, 1H). 13C NMR (67.5 MHz, CHLOROFORM-D) δ ppm 16.45, 17.11, 126.48, 127.20, 133.91, 135.05, 137.12, 140.12, 154.97, 180.48. MS (ESI+) m/z 304 (M+H)$^+$.

Example 38

4-cyano-N-(3-isopropyl-1,2,4-thiadiazol-5-yl)benzenesulfonamide

Prepared using method A.
1H NMR (400 MHz, METHANOL-D4) δ ppm 1.27 (d, J=6.84 Hz, 6H) 2.95 (m, 1H) 7.90 (d, J=8.30 Hz, 2H) 8.02 (d, J=8.30 Hz, 2H); MS (ES+) m/z 309 (M+H$^+$)

Example 39

(R)-2-(5-{[(3-chloro-2-methylphenyl)sulfonyl]amino}-1,2,4-thiadiazol-3-yl)propanamide DMF was added to tert-butyl [3-(1-bromoethyl)-1,2,4-thiadiazol-5-yl]carbamate (1.9 mmol), NaCN (1.1 eq) and NaI (1 eq). The reaction mixture was stirred for 30 min at 140° C. The reaction mixture was cooled to room temperature and the solvent was removed under reduced pressure. Standard work-up and recrystallization from EtOH afforded tert-butyl [3-(1-cyanoethyl)-1,2,4-thiadiazol-5-yl]carbamate.

This was then dissolved in DCM (0.4M) and TFA (0.4M) was added. The reaction mixture was stirred for 1 h in room temperature. The solvent was removed under reduced pressure and the salt was recrystallized from MeOH. The salt was dissolved in EtOAc and was washed with 2M NaOH and brine. Drying (MgSO$_4$) and removal of the solvent afforded 2-(5-amino-1,2,4-thiadiazol-3-yl)propanenitrile.

2-(5-amino-1,2,4-thiadiazol-3-yl)propanenitrile (0.13 mmol) was dissolved in DCM and conc. H$_2$SO$_4$ (1 mL) was added at 0° C. The ice bath was removed and the reaction mixture stirred at room temperature for 1.5 h. The reaction mixture was poured onto ice and basified by addition of NaOH (s). Extraction with DCM and drying with MgSO$_4$ gave the desired amino amide. This product was used without any further purifications and converted to the sulfonamide using procedure C.

1H NMR (400 MHz, METHANOL-D4) δ ppm 1.42 (d, J=7.08 Hz, 3H) 2.59 (s, 3H) 3.68 (q, J=7.24 Hz, 1H) 7.21 (t, J=8.06 Hz, 1H) 7.51 (d, J=8.06 Hz, 1H) 7.83 (d, J=8.00 Hz, 1H). MS m/z: (M+H) 361.

Example 40

4-fluoro-N-(3-isopropyl-1,2,4-thiadiazol-5-yl)benzenesulfonamide

Prepared using method A.

1H NMR (400 MHz, CHLOROFORM-D) δ ppm 1.31 (d, J=6.84 Hz, 6H) 3.16 (m, 1H) 7.13 (m, 2H) 7.89 (m, 2H) MS m/z 302 (M+H)$^+$

Example 41

N-(3-isopropyl-1,2,4-thiadiazol-5-yl)-2,3-dihydro-1-benzofuran-5-sulfonamide

Prepared using method A.

1H NMR (400 MHz, CHLOROFORM-D) δ ppm 1.30 (s, 3H) 1.31 (s, 3H) 3.16 (m, 1H) 3.23 (t, J=8.79 Hz, 2H) 4.65 (t, J=8.79 Hz, 2H) 6.78 (t, J=8.30 Hz, 1H) 7.67 (d, J=8.55 Hz, 1H) 7.69 (s, 1H); MS [M+H]$^+$ m/z=326.

Example 42

N-(3-isopropyl-1,2,4-thiadiazol-5-yl)-3,4-dimethoxybenzenesulfonamide

Prepared using method A.

1H NMR (400 MHz, METHANOL-D4) δ ppm 1.25 (s, 3H) 1.27 (s, 3H) 2.93 (m, 1H) 3.85 (s, 3H) 3.87 (s, 3H) 7.04 (m, J=8.54 Hz, 1H) 7.35 (d, J=1.95 Hz, 1H) 7.47 (dd, J=8.55, 1.95 Hz, 1H); MS [M+H]$^+$ m/z=344.

Example 43

N-(3-isopropyl-1,2,4-thiadiazol-5-yl)-2,3-dihydro-1,4-benzodioxine-6-sulfonamide Prepared using method A.

1H NMR (400 MHz, CHLOROFORM-D) δ ppm 1.29 (s, 3H) 1.31 (s, 3H) 3.19 (m, 1H) 4.28 (m, J=3.91 Hz, 4H) 6.90 (d, J=8.30 Hz, 1H) 7.36 (dd, J=8.55, 2.20 Hz, 1H) 7.39 (m, 1H); MS [M+H]$^+$ m/z=342.

Example 44

N-(4-{[(5-{[(3-chloro-2-methylphenyl)sulfonyl]amino}-1,2,4-thiadiazol-3-yl)methyl]thio}phenyl)acetamide Prepared using method A.

1H NMR (400 MHz, METHANOL-D4) δ ppm 2.11 (s, 3H) 2.66 (s, 3H) 3.96 (s, 2H) 7.30 (m, 3H) 7.47 (d, J=8.55 Hz, 2H) 7.62 (d, J=8.06 Hz, 1H) 7.91 (d, J=8.06 Hz, 1H); MS (ES+) m/z 469 (M+H$^+$)

Example 45

4-methyl-N-[3-(morpholin-4-ylcarbonyl)-1,2,4-thiadiazol-5-yl]benzenesulfonamide

Prepared using method D.

1H NMR (400 MHz, CHLOROFORM-D) δ ppm 2.42 (s, 3H) 3.76 (m, 6H) 4.29 (m, 2H) 7.29 (d, J=8.06 Hz, 2H) 7.80 (d, J=8.30 Hz, 2H); MS [M+H]$^+$ m/z=369.

Example 46

3-chloro-2-methyl-N-(3-phenyl-1,2,4-thiadiazol-5-yl)benzenesulfonamide

Prepared using method C.

1H NMR (270 MHz, CHLOROFORM-D) δ ppm 2.66 (s, 1H) 7.13 (m, 1H) 7.34 (m, 3H) 7.42 (d, J=8.18 Hz, 1H) 7.93 (m, 3H). MS (ESI+) m/z 366 (M+H)$^+$.

Example 47

N-[3-(3-furyl)-1,2,4-thiadiazol-5-yl]naphthalene-2-sulfonamide

Prepared using method C.

1H NMR (400 MHz, DMSO-D6) δ ppm 6.93 (d, J=1.22 Hz, 1H) 7.67 (m, 2H) 7.84 (m, 2H) 8.02 (d, J=7.81 Hz, 1H) 8.09 (d, J=8.55 Hz, 1H) 8.18 (d, J=7.57 Hz, 1H) 8.31 (s, 1H) 8.50 (s, 1H); MS [M+H]$^+$ m/z=358.

Example 48

3-chloro-2-methyl-N-(3-morpholin-4-yl-1,2,4-thiadiazol-5-yl)benzenesulfonamide

Prepared using method C.

1H NMR (400 MHz, DMSO-D6) δ ppm 2.62 (s, 3H) 3.37 (m, 4H) 3.62 (m, 4H) 7.39 (t, J=8.06 Hz, 1H) 7.70 (d, J=8.06 Hz, 1H) 7.86 (d, J=7.81 Hz, 1H). MS (ESI+) m/z 375 (H+1)

Example 49

(R)—N-(4-{[1-(5-{[(3-chloro-2-methylphenyl)sulfonyl]amino}-1,2,4-thiadiazol-3-yl)ethyl]thio}phenyl)acetamide Prepared using method A.
1H NMR (400 MHz, CHLOROFORM-D) δ ppm 1.59 (d, J=6.84 Hz, 3H) 2.16 (m, 3H) 2.66 (m, 3H) 4.25 (q, J=7.08 Hz, 1H) 6.79 (m, 1H) 7.08 (m, 1H) 7.20 (m, 1H), 7.24 (m, 1H) 7.45 (m, 1H) 7.53 (m, 1H) 7.76 (m, 1H) 7.93 (m, 1H) 8.06 (m, 1H) MS m/z 483 (M+H)+

Example 50

N-(3-isopropyl-1,2,4-thiadiazol-5-yl)-6-phenoxypyridine-3-sulfonamide

Prepared using method A.
1H NMR (400 MHz, METHANOL-D4) δ ppm 1.26 (d, J=7.08 Hz, 6H) 2.94 (m, 1H) 7.04 (d, J=8.79 Hz, 1H) 7.13 (d, J=7.81 Hz, 2H) 7.24 (t, J=7.45 Hz, 1H) 7.42 (t, J=7.93 Hz, 2H) 8.18 (dd, J=8.79, 2.44 Hz, 1H) 8.54 (d, J=2.44 Hz, 1H); MS (ES+) m/z 377 (M+H+)

Example 51

3-fluoro-N-(3-isopropyl-1,2,4-thiadiazol-5-yl)benzenesulfonamide

Prepared using method A.
1H NMR (400 MHz, METHANOL-D4) δ ppm 1.28 (d, J=6.84 Hz, 6H) 2.35 (s, 3H) 2.63 (s, 3H) 2.96 (m, 1H); MS (ES+) m/z 303 (M+H+)

Example 52

(R)-N-{4-[(1-{5-[(biphenyl-4-ylsulfonyl)amino]-1,2,4-thiadiazol-3-yl}ethyl)thio]phenyl}acetamide Prepared using method A.
1H NMR (400 MHz, CHLOROFORM-D) δ ppm 1.58 (m, 3H) 2.16 (m, 3H) 4.28 (q, J=6.84 Hz, 1H) 7.19 (m, 2H) 7.41 (m, 5H) 7.53 (m, 2H) 7.65 (m, 2H) 7.94 (m, 2H) MS m/z 511 (M+H)+

Example 53

N-[3-(3-furyl)-1,2,4-thiadiazol-5-yl]-4-phenoxybenzenesulfonamide

Prepared using method C.
1H NMR (400 MHz, DMSO-D6) δ ppm 6.94 (d, J=1.22 Hz, 1H) 7.09 (m, 4H) 7.23 (t, J=7.32 Hz, 1H) 7.44 (t, J=7.93 Hz, 2H) 7.82 (s, 1H) 7.84 (s, 2H) 8.33 (s, 1H); MS [M+H]+ m/z=400.

Example 54

5-{[(3-chloro-2-methylphenyl)sulfonyl]amino}-N-(3-ethoxypropyl)-1,2,4-thiadiazole-3-carboxamide Prepared using method D.
1H NMR (400 MHz, CHLOROFORM-D) δ ppm 0.95 (t, J=6.96 Hz, 3H) 1.59 (m, 2H) 2.45 (s, 3H) 3.24 (m, 6H) 7.00 (t, J=7.93 Hz, 1H) 7.30 (d, J=8.10 Hz, 1H) 7.68 (d, J=8.06 Hz, 1H). MS (ESI+) m/z 419 (M+H)+

Example 55

N-(3-isopropyl-1,2,4-thiadiazol-5-yl)-3-nitrobenzenesulfonamide

Prepared using method A.
1H NMR (400 MHz, CHLOROFORM-D) δ ppm 1.34 (s, 3H) 1.36 (s, 3H) 3.13 (m, 1H) 7.71 (t, J=8.06 Hz, 1H) 8.25 (d, J=7.81 Hz, 1H) 8.41 (dd, J=8.30, 1.22 Hz, 1H) 8.70 (s, 1H); MS [M+H]+ m/z=329.

Example 56

4-phenoxy-N-[3-(3-thienyl)-1,2,4-thiadiazol-5-yl]benzenesulfonamide

Prepared using method C.
1H NMR (400 MHz, DMSO-D6) δ ppm 7.10 (m, 4H) 7.23 (t, J=7.32 Hz, 1H) 7.44 (t, J=7.93 Hz, 2H) 7.60 (dd, J=5.13, 0.98 Hz, 1H) 7.70 (m, 1H) 7.83 (d, J=8.79 Hz, 2H) 8.24 (d, J=1.71 Hz, 1H); MS [M+H]+ m/z=416.

Example 57

N-(3-isopropyl-1,2,4-thiadiazol-5-yl)-2-nitrobenzenesulfonamide

Prepared using method A.
1H NMR (400 MHz, METHANOL-D4) δ ppm 1.29 (d, J=7.08 Hz, 6H) 2.98 (m, 1H) 7.76 (m, 3H) 8.13 (m, 1H); MS (ES+) m/z 329 (M+H+)

Example 58

N-(3-isopropyl-1,2,4-thiadiazol-5-yl)-3,5-bis(trifluoromethyl)benzenesulfonamide Prepared using method A.
1H NMR (400 MHz, METHANOL-D4) δ ppm 1.27 (d, J=6.84 Hz, 6H) 2.96 (m, 1H) 8.25 (s, 1H) 8.36 (s, 2H); MS (ES+) m/z 420 (M+H+)

Example 59

5-(dimethylamino)-N-(3-isopropyl-1,2,4-thiadiazol-5-yl)naphthalene-1-sulfonamide Prepared using method A.
1H NMR (400 MHz, METHANOL-D4) δ ppm 1.22 (d, J=6.84 Hz, 6H) 2.89 (m, 1H) 3.08 (s, 6H) 7.54 (d, J=7.57 Hz, 1H) 7.65 (m, 2H) 8.28 (d, J=7.32 Hz, 1H) 8.48 (d, J=8.79 Hz, 1H) 8.61 (d, J=8.54 Hz, 1H); MS (ES+) m/z 377 (M+H+)

Example 60

3-chloro-2-methyl-N-{3-[(phenylsulfonyl)methyl]-1,2,4-thiadiazol-5-yl}benzenesulfonamide Prepared using method E.
1H NMR (400 MHz, METHANOL-D4) δ ppm 2.58 (s, 3H) 4.49 (s, 2H) 7.24 (t, J=7.93 Hz, 1H) 7.44 (t, J=7.81 Hz, 2H) 7.55 (d, J=8.06 Hz, 1H) 7.60 (t, J=7.45 Hz, 1H) 7.65 (d, J=8.30 Hz, 2H) 7.83 (d, J=8.06 Hz, 1H); MS (ES+) m/z 444 (M+H+)

Example 61

2,4,6-trichloro-N-(3-morpholin-4-yl-1,2,4-thiadiazol-5-yl)benzenesulfonamide

Prepared using method C.
1H NMR (400 MHz, DMSO-D6) δ ppm 3.40 (m, 4H) 3.63 (m, 4H) 7.83 (s, 2H). MS (ESI+) m/z 429 (H+1)

Example 62

3-chloro-2-methyl-N-[3-(3-thienyl)-1,2,4-thiadiazol-5-yl]benzenesulfonamide

Prepared using method C.
1H NMR (400 MHz, DMSO-D6) δ ppm 2.65 (s, 3H) 7.40 (t, J=8.06 Hz, 1H) 7.60 (dd, J=5.13, 0.98 Hz, 1H) 7.69 (m, 1H) 7.70 (d, J=6.84 Hz, 1H) 7.91 (d, J=7.81 Hz, 1H) 8.26 (d, J=1.71 Hz, 1H); MS [M+H]$^+$ m/z=372.

Example 63

N,N-diethyl-2-(5-{[(4-phenoxyphenyl)sulfonyl]amino}-1,2,4-thiadiazol-3-yl)acetamide Prepared using method D.
1H NMR (400 MHz, CHLOROFORM-D) δ ppm 1.14 (t, J=7.20 Hz, 3H) 1.24 (m, 3H) 3.39 (m, 4H) 3.78 (s, 2H) 7.01 (d, J=8.79 Hz, 2H) 7.05 (m, 2H) 7.19 (t, J=6.59 Hz, 1H) 7.39 (m, 2H) 7.88 (d, J=9.03 Hz, 2H); MS [M+H]$^+$ m/z=447.

Example 64

4-acetyl-N-(3-isopropyl-1,2,4-thiadiazol-5-yl)benzenesulfonamide

Prepared using method A.
1H NMR (400 MHz, CHLOROFORM-D) δ ppm 1.30 (s, 3H) 1.32 (s, 3H) 2.63 (s, 3H) 3.13 (m, 1H) 7.94 (d, J=8.54 Hz, 2H) 8.00 (m, 2H); MS [M+H]$^+$ m/z=326.

Example 65

4-phenoxy-N-[3-(2-thienyl)-1,2,4-thiadiazol-5-yl]benzenesulfonamide

Prepared using method C.
1H NMR (400 MHz, DMSO-D6) δ ppm 7.10 (m, 2H) 7.12 (m, 2H) 7.21 (dd, J=5.00, 3.78 Hz, 1H) 7.25 (m, J=7.45, 7.45 Hz, 1H) 7.45 (m, 2H) 7.80 (dd, J=3.78, 0.98 Hz, 1H) 7.83 (dd, J=5.07, 0.79 Hz, 1H) 7.86 (m, 2H). MS (ESI+) m/z 416 (H+1)

Example 66

(R)-N-[2-(5-{[(3-chloro-2-methylphenyl)sulfonyl]amino}-1,2,4-thiadiazol-3-yl)propyl]butanamide This was prepared from 2-(5-amino-1,2,4-thiadiazol-3-yl)propanenitrile the preparation of which is described in Example 39.
tert-Butyl [3-(1-cyanoethyl)-1,2,4-thiadiazol-5-yl]carbamate (0.65 mmol) was dissolved in MeOH (15 mL) and a catalytic amount of Raney-Ni (50% in H$_2$O) was added. The reaction mixture was stirred at room temperature for 3 h under H$_2$ (50 psi). The reaction mixture was filtered through a pad of CELITE and the solvent was removed under reduced pressure. Purification using preparative LCMS afforded the tert-butyl [3-(2-amino-1-methylethyl)-1,2,4-thiadiazol-5-yl]carbamate.
tert-Butyl [3-(2-amino-1-methylethyl)-1,2,4-thiadiazol-5-yl]carbamate (0.27 mmol) was dissolved in DCM (5 mL) and triethylamine (1.4 eq) was added followed by n-butyric acid chloride (1.1 eq). The reaction mixture was stirred at room temperature overnight. The solvent was removed under reduced pressure. Purification, using preparative LCMS (30–70% MeCN over 10 min followed by 100% MeCN for 5 min), afforded tert-butyl [3-(2-butyrylamino-1-methyl-ethyl)-[1,2,4]thiadiazol-5-yl]-carbamate. Deprotection was carried out in DCM (1 mL) and TFA (1 mL) was added. The reaction mixture was stirred for 1.5 h at room temperature. The solvent was removed under reduced pressure affording the crude product which was converted to the sulfonamide using method C without any further purifications.
$^1$H NMR (400 MHz, CHLOROFORM-D) δ ppm 0.83 (t, J=7.40 Hz, 3H) 1.29 (d, J=6.59 Hz, 3H) 1.48–1.60 (m, 2H) 2.16 (t, J=7.32 Hz, 2H) 2.65 (s, 3H) 3.16–3.28 (m, 1H) 3.55–3.63 (m, 2H) 6.32–6.42 (m, 1H) 7.22 (t, J=7.93 Hz, 1H) 7.50 (d, J=7.81 Hz, 1H) 7.92 (d, J=8.06 Hz, 1H). MS m/z: (M+H) 418.

Example 67

N-(3-isopropyl-1,2,4-thiadiazol-5-yl)naphthalene-1-sulfonamide

Prepared using method A.
1H NMR (400 MHz, CHLOROFORM-D) δ ppm 1.28 (d, J=6.84 Hz, 6H) 3.10 (m, 1H) 7.22 (m, 1H) 7.46 (m, 2H) 7.87 (m, 1H) 8.03 (m, 1H) 8.26 (dd, J=7.32, 1.22 Hz, 1H) 8.56 (m, 1H) MS m/z 334 (M+H)$^+$

Example 68

2,6-difluoro-N-(3-isopropyl-1,2,4-thiadiazol-5-yl)benzenesulfonamide

Prepared using method A.
1H NMR (400 MHz, CHLOROFORM-D) δ ppm 1.30 (d, J=6.84 Hz, 6H) 3.30 (m, 1H) 6.94 (m, 2H) 7.46 (m, 1H) MS m/z 320 (M+H)$^+$

Example 69

3-chloro-2-methyl-N-[3-(morpholin-4-ylcarbonyl)-1,2,4-thiadiazol-5-yl]benzenesulfonamide Prepared using method D.
1H NMR (400 MHz, METHANOL-D4) δ ppm 2.70 (s, 3H) 3.70 (m, 6H) 4.00 (m, 2H) 7.29 (t, J=7.93 Hz, 1H) 7.59 (d, J=7.81 Hz, 1H) 7.93 (d, J=7.81 Hz, 1H); MS [M+H]$^+$ m/z=403.

Example 70

Ethyl 1-[(5-{[(3-chloro-2-methylphenyl)sulfonyl]amino}-1,2,4-thiadiazol-3-yl)carbonyl]piperidine-3-carboxylate Prepared using method D.
%). 1H NMR (400 MHz, DMSO-D6) δ ppm 1.07 (t, J=7.08 Hz, 1.5H) 1.19 (t, J=7.08 Hz, 1.5H) 1.49 (m, 1H) 1.68 (m, 2H) 1.93 (m, 1H) 2.59 (m, J=8.30, 4.15 Hz, 1H)

2.61 (s, 3H) 3.20 (m, 1H) 3.70 (m, 1H) 4.01 (m, 3H) 4.28 (m, 1H) 7.40 (m, 1H) 7.70 (m, 1H) 7.89 (m, 1H). MS (ESI+) m/z 473 (M+H)+

Example 71

N-(3-isopropyl-1,2,4-thiadiazol-5-yl)-4-methylbenzenesulfonamide

Prepared using method A.
1H NMR (400 MHz, CHLOROFORM-D) δ ppm 1.31 (m, 6H) 2.40 (s, 3H) 3.15 (m, 1H) 7.25 (m, 2H) 7.76 (d, J=8.30 Hz, 2H). 13CNMR (400 MHz, CHLOROFORM-D) δ ppm 20.46, 21.66, 30.22, 76.68, 126.42, 129.49, 155.95. MS [M+H]+ m/z=398.

Example 72

3-chloro-N-{3-[(3-hydroxypiperidin-1-yl)carbonyl]-1,2,4-thiadiazol-5-yl}-2-methylbenzenesulfonamide Prepared using method D.
1H NMR (400 MHz, CHLOROFORM-D) δ ppm 1.73 (m, 4H) 2.69 (s, 3H) 3.35 (m, 1H) 3.64 (m, 1H) 3.95 (m, 1H) 4.14 (m, 1H) 4.29 (m, 1H) 7.26 (m, 1H) 7.57 (m, 1H) 7.98 (m, 1H). MS (ESI+) m/z 417 (M+H)+

Example 73

3-chloro-2-methyl-N-[3-(trichloromethyl)-1,2,4-thiadiazol-5-yl]benzenesulfonamide Prepared using method C.
1H NMR (270 MHz, CHLOROFORM-D) δ ppm 2.41 (s, 3H) 6.99 (t, J=8.05 Hz, 1H) 7.45 (d, J=7.13 Hz, 1H) 7.71 (d, J=7.13 Hz, 1H). MS (ESI+) m/z 406 (M+H)+.

Example 74

N-(3-isopropyl-1,2,4-thiadiazol-5-yl)-4-nitrobenzenesulfonamide

Prepared using method A.
1H NMR (400 MHz, CHLOROFORM-D) δ ppm 1.33 (d, J=6.84 Hz, 6H) 3.10 (m, 1H) 8.08 (m, 2H) 8.30 (m, 2H) MS m/z 329 (M+H)+

Example 75

N-(3-isopropyl-1,2,4-thiadiazol-5-yl)-2-(trifluoromethyl)benzenesulfonamide

Prepared using method A.
1H NMR (400 MHz, METHANOL-D4) δ ppm 1.26 (d, J=7.08 Hz, 6H) 2.95 (m, 1H) 7.77 (m, 2H) 7.90 (m, 1H) 8.26 (m, 1H); MS (ES+) m/z 352 (M+H+)

Example 76

3,5-dichloro-2-hydroxy-N-(3-isopropyl-1,2,4-thiadiazol-5-yl)benzenesulfonamide

Prepared using method A.
1H NMR (400 MHz, CHLOROFORM-D) δ ppm 1.34 (d, J=7.08 Hz, 6H) 3.00 (m, 1H) 7.51 (m, 1H) 7.62 (m, 1H) MS m/z 368 (M+H)+

Example 77

N-[3-(3-thienyl)-1,2,4-thiadiazol-5-yl]biphenyl-4-sulfonamide

Prepared using method C.
1H NMR (400 MHz, DMSO-D6) δ ppm 7.42 (t, J=7.32 Hz, 1H) 7.49 (t, J=7.45 Hz, 2H) 7.61 (dd, J=5.13, 0.98 Hz, 1H) 7.70 (m, 3H) 7.85 (d, J=8.30 Hz, 2H) 7.91 (d, J=8.55 Hz, 2H) 8.26 (m, 1H); MS [M+H]+ m/z=400.

Example 78

5-fluoro-N-(3-isopropyl-1,2,4-thiadiazol-5-yl)-2-methylbenzenesulfonamide

Prepared using method A.
1H NMR (400 MHz, CHLOROFORM-D) δ ppm 1.30 (s, 3H) 1.32 (s, 3H) 2.51 (s, 3H) 3.13 (m, 1H) 7.14 (m, 1H) 7.22 (m, 1H) 7.72 (m, J=8.55, 2.44 Hz, 1H); MS [M+H]+ m/z=316.

Example 79

3-chloro-2-methyl-N-[3-(2-morpholin-4-ylethyl)-1,2,4-thiadiazol-5-yl]benzenesulfonamide Prepared using method C.
MS (ESI+) m/z 403 (M+H).

Example 80

N-(3-isopropyl-1,2,4-thiadiazol-5-yl)-2-methyl-5-nitrobenzenesulfonamide

Prepared using method A.
1H NMR (400 MHz, CHLOROFORM-D) δ ppm 1.33 (d, J=6.84 Hz, 6H) 2.73 (m, 3H) 3.11 (m, 1H) 7.48 (m, 1H) 8.27 (m, 1H) 8.80 (m, 1H) MS m/z 343 (M+H)+

Example 81

2,4-difluoro-N-(3-isopropyl-1,2,4-thiadiazol-5-yl)benzenesulfonamide

Prepared using method A.
1H NMR (400 MHz, CHLOROFORM-D) δ ppm 1.31 (d, J=6.84 Hz, 6H) 3.27 (m, 1H) 6.84 (m, 1H) 6.98 (m, 1H) 7.97 (m, 1H) MS m/z 320 (M+H)+

Example 82

3-chloro-2-methyl-N-[3-(2-thienyl)-1,2,4-thiadiazol-5-yl]benzenesulfonamide

Prepared using method C.
1H NMR (400 MHz, DMSO-D6) δ ppm 2.65 (s, 3H) 7.20 (m, 1H) 7.41 (t, J=7.93 Hz, 1H) 7.71 (d, J=8.79 Hz, 1H) 7.81 (m, 2H) 7.91 (d, J=8.06 Hz, 1H). MS (ESI+) m/z 372 (H+1)

Example 83

3-chloro-N-(3-methoxy-1,2,4-thiadiazol-5-yl)-2-methylbenzenesulfonamide

Prepared using method C.
1H NMR (400 MHz, METHANOL-D4) δ ppm 2.68 (s, 3H) 3.99 (s, 3H) 7.31 (t, J=7.93 Hz, 1H) 7.61 (d, J=8.06 Hz, 1H) 7.92 (d, J=8.06 Hz, 1H); MS [M+H]+ m/z 319.

Example 84

(R)-3-chloro-N-(3-{1-[(3,4-dimethoxyphenyl)thio]ethyl}-1,2,4-thiadiazol-5-yl)-2-methylbenzenesulfonamide Prepared using method A.
1H NMR (400 MHz, CHLOROFORM-D) δ ppm 1.56 (d, J=7.08 Hz, 3H) 2.61 (m, 3H) 3.72 (m, 3H) 3.81 (m, 3H) 4.30 (q, J=7.08 Hz, 1H) 6.71 (m, 1H) 6.77 (m, 1H) 6.88 (dd, J=8.30, 1.95 Hz, 1H) 7.23 (m, 1H) 7.56 (dd, J=7.81, 1.47 Hz, 1H) 7.95 (dd, J=7.81, 1.22 Hz, 1H) MS m/z 486 (M+H)$^+$

Example 85

N-[3-(3-furyl)-1,2,4-thiadiazol-5-yl]biphenyl-4-sulfonamide

Prepared using method C.
1H NMR (400 MHz, DMSO-D6) δ ppm 6.95 (d, J=1.22 Hz, 1H) 7.42 (t, J=7.32 Hz, 2H) 7.49 (t, J=7.45 Hz, 2H) 7.70 (d, J=7.32 Hz, 2H) 7.85 (m, 3H) 7.91 (m, 2H) 8.33 (s, 1H); MS [M+H]$^+$ m/z=384.

Example 86

3-chloro-N-(3-ethyl-1,2,4-thiadiazol-5-yl)-2-methylbenzenesulfonamide

Prepared using method C.
1H NMR (400 MHz, CHLOROFORM-D) δ ppm 1.3 (t, J=7.4 Hz, 3H) 2.6 (s, 3H) 2.8 (q, J=7.6 Hz, 2H) 7.2 (m, 1H) 7.5 (dd, J=7.9, 1.3 Hz, 1H) 7.9 (dd, J=8.1, 1.2 Hz, 1H). MS (ESI+) m/z 318 (M+H).

Comparison Example 87

N-(3-isopropyl-1,2,4-thiadiazol-5-yl)-3-(trifluoromethyl)benzenesulfonamide

Prepared using method A.
1H NMR (400 MHz, CHLOROFORM-D) δ ppm 1.33 (d, J=6.84 Hz, 6H) 3.11 (m, 1H) 7.62 (s, 1H) 7.81 (s, 1H) 8.11 (d, J=26.61 Hz, 1H). MS [M+H]$^+$ m/z=352.

Example 88

N-(3-{[(5-{[(3-chloro-2-methylphenyl)sulfonyl]amino}-1,2,4-thiadiazol-3-yl)methyl]thio}phenyl)acetamide Prepared using method A.
1H NMR (400 MHz, METHANOL-D4) δ ppm 2.10 (s, 3H) 2.66 (s, 3H) 4.04 (s, 2H) 7.05 (d, J=7.81 Hz, 1H) 7.18 (t, J=7.93 Hz, 1H) 7.31 (t, J=8.06 Hz, 1H) 7.37 (d, J=7.81 Hz, 1H) 7.61 (d, J=7.81 Hz, 1H) 7.68 (s, 1H) 7.91 (d, J=7.81 Hz, 1H); MS (ES+) m (M+H$^+$)

Example 89

N-[3-(morpholin-4-ylcarbonyl)-1,2,4-thiadiazol-5-yl]-4-phenoxybenzenesulfonamide Prepared using method D.
1H NMR (400 MHz, CHLOROFORM-D) δ ppm 3.76 (m, 6H) 4.24 (m, 2H) 7.01 (d, J=9.03 Hz, 2H) 7.05 (d, J=7.81 Hz, 2H) 7.21 (m, J=7.45, 7.45 Hz, 1H) 7.40 (t, J=7.93 Hz, 2H) 7.86 (d, J=8.79 Hz, 2H); MS [M+H]$^+$ m/z=447.

Example 90

3-chloro-2-methyl-N-(3-{[(4-methylpyrimidin-2-yl)thio]methyl}-1,2,4-thiadiazol-5-yl)benzenesulfonamide Prepared using method A.
1H NMR (400 MHz, CHLOROFORM-D) δ ppm 2.56 (s, 3H) 2.68 (s, 3H) 4.17 (s, 2H) 7.04 (d, J=5.13 Hz, 1H) 7.22 (m, 1H) 7.53 (d, J=8.06 Hz, 1H) 7.95 (d, J=7.81 Hz, 1H) 8.51 (d, J=5.13 Hz, 1H); MS (ES+) m/z 428 (M+H$^+$)

Example 91

N-(3-isopropyl-1,2,4-thiadiazol-5-yl)-5-methyl-2-(trifluoromethyl)furan-3-sulfonamide Prepared using method A.
1H NMR (400 MHz, CHLOROFORM-D) δ ppm 1.33 (m, 6H) 2.62 (m, 3H) 3.09 (m, 1H) 6.94 (m, 1H) MS m/z 356 (M+H)$^+$

Example 92

N-(3-methyl-1,2,4-thiadiazol-5-yl)-4-phenoxybenzenesulfonamide

Prepared using method C.
1H NMR (400 MHz, DMSO-D6) δ ppm 2.27 (s, 3H) 7.09 (m, 4H) 7.24 (t, J=7.45 Hz, 1H) 7.45 (t, J=7.93 Hz, 2H) 7.79 (d, J=9.03 Hz, 2H); MS [M+H]$^+$ m/z 348.

Example 93

(R)-3-chloro-2-methyl-N-(3-{1-[(4-methylpyrimidin-2-yl)thio]ethyl}-1,2,4-thiadiazol-5-yl)benzenesulfonamide Prepared using method A.
1H NMR (400 MHz, CHLOROFORM-D) δ ppm 1.80 (d, J=7.57 Hz, 3H) 2.56 (m, 3H) 2.68 (m, 3H) 4.62 (q, J=7.32 Hz, 1H) 7.03 (d, J=5.13 Hz, 1H) 7.21 (m, 1H) 7.95 (m, 1H) 8.50 (d, J=5.13 Hz, 1H) MS m/z 442 (M+H)$^+$

Example 94

N-(3-isopropyl-1,2,4-thiadiazol-5-yl)-4-(phenylsulfonyl)thiophene-2-sulfonamide

Prepared using method A.
1H NMR (400 MHz, CHLOROFORM-D) δ ppm 1.31 (m, 6H) 3.11 (m, 1H) 7.55 (m, 2H) 7.64 (m, 1H) 7.78 (m, 1H) 7.96 (m, 2H) 8.27 (m, 1H) MS m/z 430 (M+H)$^+$

Example 95

3-chloro-4-fluoro-N-(3-isopropyl-1,2,4-thiadiazol-5-yl)benzenesulfonamide

Prepared using method A.
1H NMR (400 MHz, CHLOROFORM-D) δ ppm 1.32 (d, J=6.84 Hz, 6H) 3.15 (m, 1H) 7.22 (m, 1H) 7.79 (m, 1H) 7.93 (m, 1H) MS m/z 336 (M+H)$^+$

Example 96

N-(3-ethyl-1,2,4-thiadiazol-5-yl)-5-[2-(methylthio)pyrimidin-4-yl]thiophene-2-sulfonamide Prepared using method C.
1H NMR (400 MHz, DMSO-D6) δ ppm 1.17 (t, J=7.57 Hz, 3H) 2.54 (s, 3H) 2.63 (q, J=7.49 Hz, 2H) 7.68 (d, J=4.15 Hz, 1H) 7.76 (d, J=5.13 Hz, 1H) 8.03 (d, J=3.91 Hz, 1H) 8.68 (d, J=5.13 Hz, 1H); MS (ES+) m/z 400 (M+H$^+$)

Example 97

4-methyl-N-[3-(trichloromethyl)-1,2,4-thiadiazol-5-yl]benzenesulfonamide

Prepared using method C.
1H NMR (270 MHz, CHLOROFORM-D) δ ppm 2.34 (s, 3H) 5.51 (br. s, 1H) 7.14 (d, J=7.92 Hz, 2H) 7.73 (d, J=8.18 Hz, 2H). MS (ESI+) m/z 372 (M+H)$^+$.

Example 98

(R)-2-(5-{[(3-chloro-2-methylphenyl)sulfonyl]amino}-1,2,4-thiadiazol-3-yl)-1-methylethyl 3-chloro-2-methylbenzenesulfonate This was prepared from 5-amino-3-(2-hydroxypropyl)-1,2,4-thiadiazol using method C and 2 eq of the sulfonyl chloride.
1H NMR (400 MHz, CHLOROFORM-D) δ ppm 1.3 (d, J=6.3 Hz, 3H) 2.5 (s, 3H) 2.6 (d, J=5.6 Hz, 3H) 3.1 (m, 2H) 5.0 (m, 1H) 7.2 (m, 2H) 7.5 (dd, J=16.0, 7.9 Hz, 2H) 7.8 (d, J=7.8 Hz, 1H) 7.9 (dd, J=7.9, 1.1 Hz, 1H); MS (ESI+) m/z 537 (M+H).

Example 99

3-chloro-2-methyl-N-{3-[(3-oxopiperazin-1-yl)carbonyl]-1,2,4-thiadiazol-5-yl}benzenesulfonamide Prepared using method D.
1H NMR (400 MHz, DMSO-D6) δ ppm 2.63 (s, 3H) 3.23 (m, 2H) 3.75 (t, J=5.25 Hz, 1H) 3.85 (t, J=5.25 Hz, 1H) 4.07 (s, 1H) 4.31 (s, 1H) 7.40 (m, 1H) 7.69 (m, 1H) 7.89 (dd, J=7.87, 1.28 Hz, 1H) 8.14 (d, J=9.64 Hz, 1H). MS (ESI+) m/z 416 (M+H)$^+$

Example 100

3-chloro-N-(3-{[(3,4-dimethoxyphenyl)thio]methyl}-1,2,4-thiadiazol-5-yl)-2-methylbenzenesulfonamide Prepared using method A.
1H NMR (400 MHz, METHANOL-D4) δ ppm 2.68 (s, 3H) 3.68 (s, 3H) 3.79 (s, 3H) 3.91 (s, 2H) 6.82 (d, J=8.30 Hz, 1H) 6.86 (d, J=1.95 Hz, 1H) 6.93 (dd, J=8.30, 1.95 Hz, 1H) 7.32 (t, J=7.93 Hz, 1H) 7.63 (d, J=7.81 Hz, 1H) 7.91 (d, J=7.81 Hz, 1H); MS (ES+) m/z 472 (M+H$^+$)

Example 101

N-(3-isopropyl-1,2,4-thiadiazol-5-yl)-2,4,6-trimethylbenzenesulfonamide

Prepared using method A.
1H NMR (400 MHz, CHLOROFORM-D) δ ppm 1.30 (d, J=6.84 Hz, 6H) 2.29 (m, 3H) 2.64 (m, 6H) 3.11 (m, 1H) 6.93 (m, 2H) MS m/z 326 (M+H)$^+$

Example 102

5-bromo-6-chloro-N-(3-isopropyl-1,2,4-thiadiazol-5-yl)pyridine-3-sulfonamide

Prepared using method A.
1H NMR (400 MHz, ACETONE-D6) δ ppm 1.31 (m, 6H) 3.09 (m, 1H) 8.43 (m, 1H) 8.76 (m, 1H). MS m/z 397 (M+H)$^+$

Example 103

(R)-3-chloro-2-methyl-N-{3-[1-(phenylsulfonyl)ethyl]-1,2,4-thiadiazol-5-yl}benzenesulfonamide Prepared using method E.
1H NMR (400 MHz, CHLOROFORM-D) δ ppm 1.65 (d, J=7.08 Hz, 3H) 2.66 (m, 3H) 4.60 (q, J=7.08 Hz, 1H) 7.26 (m, 1H) 7.54 (m, 2H) 7.58 (m, 1H) 7.67 (m, 1H) 7.77 (m, 2H) 7.98 (m, 1H) MS m/z 458 (M+H)$^+$

Example 104

3-chloro-N-(3-{[(2-methoxyphenyl)thio]methyl}-1,2,4-thiadiazol-5-yl)-2-methylbenzenesulfonamide Prepared using method A.
1H NMR (400 MHz, METHANOL-D4) δ ppm 2.69 (s, 3H) 3.68 (s, 3H) 3.91 (s, 2H) 6.79 (t, J=7.57 Hz, 1H) 6.88 (d, J=8.30 Hz, 1H) 7.26 (t, J=7.81 Hz, 1H) 7.31 (m, 2H) 7.62 (d, J=7.81 Hz, 1H) 7.90 (d, J=8.06 Hz, 1H); MS (ES+) m/z 442 (M+H$^+$)

Example 105

N-(3-methoxy-1,2,4-thiadiazol-5-yl)-4-phenoxybenzenesulfonamide

Prepared using method C.
1H NMR (400 MHz, DMSO-D6) δ ppm 3.87 (s, 3H) 7.05 (d, J=8.79 Hz, 2H) 7.10 (d, J=7.81 Hz, 2H) 7.23 (t, J=7.32 Hz, 1H) 7.44 (t, J=7.93 Hz, 2H) 7.77 (d, J=8.79 Hz, 2 H); MS [M+H]$^+$ m/z 364.

Example 106

(R)-3-chloro-2-methyl-N-{3-[1-(pyridin-3-yloxy)ethyl]-1,2,4-thiadiazol-5-yl}benzenesulfonamide Prepared using method A.
1H NMR (400 MHz, METHANOL-D4) δ ppm 1.73 (d, J=6.59 Hz, 3H) 2.68 (s, 3H) 5.65 (q, J=6.35 Hz, 1H) 7.30 (t, J=7.93 Hz, 1H) 7.61 (d, J=8.06 Hz, 1H) 7.75 (dd, J=8.06, 5.13 Hz, 1H) 7.92 (d, J=7.81 Hz, 1H) 7.96 (dd, J=8.67, 2.08 Hz, 1H) 8.37 (s, 1 H); MS (ES+) m/z 411 (M+H$^+$)

Example 107

(R)-3-chloro-2-methyl-N-{3-[1-(pyridin-4-ylthio)ethyl]-1,2,4-thiadiazol-5-yl}benzenesulfonamide Prepared using method A.
1H NMR (400 MHz, CHLOROFORM-D) δ ppm 1.84 (d, J=7.08 Hz, 3H) 2.58 (m, 3H) 4.96 (q, J=7.32 Hz, 1H) 7.21 (m, 1H) 7.54 (dd, J=7.08, 0.98 Hz, 1H) 7.78 (d, J=7.08 Hz, 2H) 7.89 (dd, J=6.84, 0.98 Hz, 1H) 8.56 (d, J=6.84 Hz, 2H) MS m/z 427 (M+H)$^+$

Example 108

N-(3-tert-butyl-1,2,4-thiadiazol-5-yl)-4-phenoxybenzenesulfonamide

Prepared using method C.
1H NMR (400 MHz, DMSO-D6) δ ppm 1.25 (s, 9H) 7.09 (d, J=8.79 Hz, 2H) 7.12 (d, J=7.81 Hz, 2H) 7.24 (t, J=7.32 Hz, 1H) 7.45 (t, J=7.93 Hz, 2H) 7.81 (d, J=8.79 Hz, 2H). MS (ESI+) m/z 390 (H+1)

Example 109

4-bromo-N-(3-cyclopropyl-1,2,4-thiadiazol-5-yl)benzenesulfonamide

Prepared using method C.
1H NMR (400 MHz, DMSO-D6) δ ppm 0.97 (m, 4H) 1.97 (m, 1H) 7.75 (m, 4H). MS (ESI+) m/z 360 (H+1)

Example 110

N-(3-ethyl-1,2,4-thiadiazol-5-yl)-4-phenoxybenzenesulfonamide

Prepared using method C.
1H NMR (400 MHz, DMSO-D6) δ ppm 1.17 (t, J=7.57 Hz, 3H) 2.60 (q, J=7.41 Hz, 2H) 7.09 (m, 4H) 7.24 (t, J=7.45 Hz, 1H) 7.45 (t, J=7.93 Hz, 2H) 7.79 (d, J=8.79 Hz, 2H); MS [M+H]$^+$ m/z 362.

Example 111

3-chloro-2-methyl-N-(3-{[(1-methyl-1H-imidazol-2-yl)thio]methyl}-1,2,4-thiadiazol-5-yl)benzenesulfonamide Prepared using method A.
1H NMR (400 MHz, METHANOL-D4) δ ppm 2.43 (s, 3H) 3.61 (s, 3H) 3.98 (s, 2H) 7.06 (t, J=8.06 Hz, 1H) 7.36 (m, 2H) 7.44 (d, J=1.95 Hz, 1H) 7.66 (d, J=7.57 Hz, 1H); MS (ES+) m/z 416 (M+H)$^+$

Example 112

3-chloro-2-methyl-N-[3-(trichloromethyl)-1,2,4-thiadiazol-5-yl]benzenesulfonamide Prepared using method A.
1H NMR (400 MHz, CHLOROFORM-D) δ ppm 2.59 (s, 3H) 4.45 (s, 2H) 7.24 (m, J=5.13 Hz, 1H) 7.57 (d, J=7.57 Hz, 1H) 7.86 (d, J=6.35 Hz, 1H) 7.89 (d, J=8.06 Hz, 1H) 8.63 (d, J=6.10 Hz, 2H); MS (ES+) m/z 413 (M+H)$^+$

Example 113

3-chloro-2-methyl-N-{3-[(pyridin-4-ylthio)methyl]-1,2,4-thiadiazol-5-yl}benzenesulfonamide Prepared using method A.
1H NMR (400 MHz, CHLOROFORM-D) δ ppm 1.60 (d, J=7.32 Hz, 3H) 2.68 (m, 3H) 3.80 (m, 3H) 4.16 (q, J=7.08 Hz, 1H) 6.86 (dd, J=8.30, 1.22 Hz, 1H) 6.90 (m, 1H) 1.22 Hz, 1 (t, J=7.81 Hz, 1H) 7.34 (m, 1H) 7.44 (dd, J=7.57, 1.71 Hz, 1H) 7.54 (dd, J=8.06, 1.22 Hz, 1H) 7.96 (dd, J=8.06, 1.22 Hz, 1H) MS m/z 456 (M+H)$^+$

Example 114

(R)-3-chloro-N-(3-{1-[(2-methoxyphenyl)thio]ethyl}-1,2,4-thiadiazol-5-yl)-2-methylbenzenesulfonamide Prepared using method A.
1H NMR (400 MHz, DMSO-D6) δ ppm 2.35 (s, 3H) 4.12 (s, 2H) 7.22 (t, J=7.08 Hz, 1H) 7.29 (t, J=7.57 Hz, 2H) 7.34 (d, J=7.81 Hz, 4H) 7.66 (d, J=8.30 Hz, 2 H); MS (ES+) m/z 378 (M+H$^+$)

Example 115

4-methyl-N-{3-[(phenylthio)methyl]-1,2,4-thiadiazol-5-yl}benzenesulfonamide

Prepared using method A.
1H NMR (400 MHz, CHLOROFORM-D) δ ppm 1.31 (d, J=6.84 Hz, 6H) 2.41 (m, 3H) 3.19 (m, 1H) 7.30 (m, 1H) 7.65 (m, 1H) 7.82 (m, 1H) MS m/z 332 (M+H)$^+$

Example 116

3-chloro-N-(3-isopropyl-1,2,4-thiadiazol-5-yl)-4-methylbenzenesulfonamide

Prepared using method A.
1H NMR (400 MHz, CHLOROFORM-D) δ ppm 1.31 (d, J=6.84 Hz, 6H) 2.41 (m, 3H) 3.19 (m, 1H) 7.30 (m, 1H) 7.65 (m, 1H) 7.82 (m, 1H) MS m/z 332 (M+H)$^+$

Example 117

N-(2-{[(5-{[(3-chloro-2-methylphenyl)sulfonyl]amino}-1,2,4-thiadiazol-3-yl)methyl]thio}phenyl)acetamide Prepared using method A.
1H NMR (400 MHz, METHANOL-D4) δ ppm 2.09 (s, 3H) 2.67 (s, 3H) 3.94 (s, 2H) 7.05 (t, J=7.32 Hz, 1H) 7.27 (m, 1H) 7.32 (t, J=8.06 Hz, 1H) 7.42 (d, J=7.81 Hz, 1H) 7.62 (d, J=7.81 Hz, 1H) 7.71 (d, J=8.06 Hz, 1H) 7.90 (d, J=7.81 Hz, 1H); MS (ES+) m/z 469 (M+H$^+$)

Example 118

3-chloro-2-methyl-N-{3-[(pyridin-2-ylthio)methyl]-1,2,4-thiadiazol-5-yl}benzenesulfonamide Prepared using method A.
1H NMR (400 MHz, METHANOL-D4) δ ppm 2.67 (s, 3H) 4.35 (s, 2H) 7.13 (td, J=6.23, 0.73 Hz, 1H) 7.30 (m, 1H) 7.34 (d, J=9.28 Hz, 1H) 7.61 (d, J=7.81 Hz, 1H) 7.64 (m, 1H) 7.92 (d, J=7.81 Hz, 1H) 8.40 (d, J=4.15 Hz, 1H); MS (ES+) m/z 413 (M+H$^+$)

Example 119

N-(3-isopropyl-1,2,4-thiadiazol-5-yl)-4-(1H-pyrazol-1-yl)benzenesulfonamide

Prepared using method A.

1H NMR (400 MHz, METHANOL-D4) δ ppm 1.27 (d, J=7.08 Hz, 6H) 2.95 (m, 1H) 6.56 (m, 1H) 7.76 (d, J=1.22 Hz, 1H) 7.95 (m, 4H) 8.33 (d, J=2.44 Hz, 1H); m/z 350 (M+H$^+$)

Example 120

Prepared using method C.

4-bromo-N-(3-tert-butyl-1,2,4-thiadiazol-5-yl)benzenesulfonamide

1H NMR (400 MHz, DMSO-D6) δ ppm 1.25 (s, 9H) 7.76 (m, 4H). MS (ESI+) m/z 376 (H+1)

Example 121

(R)-3-chloro-N-(3-{2-[(3-fluorophenyl)thio]propyl}-1,2,4-thiadiazol-5-yl)-2-methylbenzenesulfonamide (R)-2-(5-{[(3-chloro-2-methylphenyl)sulfonyl]amino}-1,2,4-thiadiazol-3-yl)-1-methylethyl 3-chloro-2-methylbenzenesulfonate (example 98), 3-fluorothiophenol (1 eq) and sodium carbonate (1 eq) in CH$_3$CN were heated overnight. Standard work-up and purification yielded the desired product.

1H NMR (400 MHz, CHLOROFORM-D) δ ppm 1.3 (m, 3H) 2.6 (m, 3H) 2.9 (m, 2H) 3.8 (m, 1H) 6.8 (m, 1H) 7.1 (m, 5H) 7.5 (m, 1H) 7.9 (m, 1H); MS (ESI+) m/z 458 (M+H).

Example 122

N-(3-isopropyl-1,2,4-thiadiazol-5-yl)-2,2,4,6,7-pentamethyl-2,3-dihydro-1-benzofuran-5-sulfonamide Prepared using method A.

1H NMR (400 MHz, CHLOROFORM-D) δ ppm 1.29 (d, J=7.08 Hz, 6H) 1.46 (m, 6H) 2.07 (m, 3H) 2.53 (m, 6H) 2.96 (m, 2H) 3.12 (m, 1H) MS m/z 396 (M+H)$^+$

Example 123

N-(3-isopropyl-1,2,4-thiadiazol-5-yl)-4-methoxy-2,3,6-trimethylbenzenesulfonamide Prepared using method A.

1H NMR (400 MHz, CHLOROFORM-D) δ ppm 1.30 (d, J=6.84 Hz, 6H) 2.11 (m, 3H) 2.55 (m, 3H) 2.72 (m, 3H) 3.12 (m, 1H) 3.85 (m, 3H) 6.56 (m, 1H) MS m/z 356 (M+H)$^+$

Example 124

N-(3-tert-butyl-1,2,4-thiadiazol-5-yl)-3-chloro-2-methylbenzenesulfonamide

Prepared using method C.

1H NMR (400 MHz, DMSO-D6) δ ppm 1.26 (s, 9H) 2.64 (s, 3H) 7.41 (t, J=7.93 Hz, 1H) 7.72 (d, J=8.06 Hz, 1H) 7.89 (d, J=8.06 Hz, 1H). MS (ESI+) m/z 346 (H+1)

Example 125

(R)-3-chloro-N-{3-[1-(2,3-difluorophenoxy)ethyl]-1,2,4-thiadiazol-5-yl}-2-methylbenzenesulfonamide Prepared using method A.

1H NMR (400 MHz, METHANOL-D4) δ ppm 1.69 (d, J=6.35 Hz, 3H) 2.68 (s, 3H) 5.40 (q, J=6.51 Hz, 1H) 6.90 (q, J=7.81 Hz, 2H) 7.02 (m, 1H) 7.31 (t, J=8.06 Hz, 1H) 7.61 (d, J=7.81 Hz, 1H) 7.93 (d, J=7.81 Hz, 1H); MS (ES+) m/z 446 (M+H$^+$)

Example 126

N-(3-isopropyl-1,2,4-thiadiazol-5-yl)-5-pyridin-2-ylthiophene-2-sulfonamide

Prepared using method A.

1H NMR (400 MHz, CHLOROFORM-D) δ ppm 1.34 (m, 6H) 3.14 (m, 1H) 7.48 (m, 1H) 7.64 (m, 2H) 7.77 (m, 1H) 7.97 (m, 1H) 8.74 (m, 1H) MS m/z 367 (M+H)$^+$

Example 127

N-(3-cyclopropyl-1,2,4-thiadiazol-5-yl)naphthalene-2-sulfonamide

Prepared using method C.

1H NMR (400 MHz, DMSO-D6) δ ppm 0.97 (m, 4H) 1.96 (m, 1H) 7.67 (m, 2H) 7.79 (d, J=10.50 Hz, 1H) 8.02 (d, J=8.06 Hz, 1H) 8.09 (d, J=8.79 Hz, 1H) 8.17 (d, J=7.81 Hz, 1H) 8.47 (s, 1H). MS (ESI+) m/z 332 (H+1)

Example 128

Prepared using method C.

N-(3-isopropyl-1,2,4-thiadiazol-5-yl)-4-phenoxybenzenesulfonamide

1H NMR (400 MHz, CHLOROFORM-D) δ ppm 1.31 (d, J=6.84 Hz, 6H) 3.05 (m, 1H) 7.00 (d, J=8.79 Hz, 2H) 7.04 (m, 2H) 7.20 (m, 1H) 7.39 (m, 2H) 7.84 (d, J=8.79 Hz, 2H). MS [M+H]$^+$ m/z 376.

Example 129

N-(3-isopropyl-1,2,4-thiadiazol-5-yl)-4-(1,3-oxazol-5-yl)benzenesulfonamide

Prepared using method A.

1H NMR (400 MHz, ACETONE-D6) δ ppm 1.29 (m, 6H) 3.05 (m, 1H) 7.73 (m, 1H) 7.92 (m, 4H) 8.27 (m, 1H). MS m/z 351 (M+H)$^+$

Example 130

4-bromo-N-{3-[(phenylthio)methyl]-1,2,4-thiadiazol-5-yl}benzenesulfonamide

Prepared using method A.

1H NMR (400 MHz, METHANOL-D4) δ ppm 4.01 (s, 2H) 7.19 (m, 3H) 7.30 (d, J=7.32 Hz, 2H) 7.62 (d, J=8.55 Hz, 2H) 7.76 (d, J=8.55 Hz, 2H); MS (ES+) m/z 442 (M+H$^+$)

Example 131

2,6-dichloro-N-(3-isopropyl-1,2,4-thiadiazol-5-yl) benzenesulfonamide

Prepared using method A.

1H NMR (400 MHz, CHLOROFORM-D) δ ppm 1.31 (m, 6H) 3.29 (m, 1H) 7.29 (m, 1H) 7.39 (m, 1H) 7.41 (m, 1H). MS m/z 352 (M+H)+

Example 132

5-{[(3-chloro-2-methylphenyl)sulfonyl]amino}-N,N-diethyl-1,2,4-thiadiazole-3-carboxamide Prepared using method D.

1H NMR (400 MHz, METHANOL-D4) δ ppm 1.19 (t, J=7.08 Hz, 3H) 1.25 (t, J=7.08 Hz, 3H) 2.70 (s, 3H) 3.48 (q, J=7.08 Hz, 2H) 3.69 (m, J=7.08, 7.08, 7.08 Hz, 2H) 7.30 (t, J=8.06 Hz, 1H) 7.59 (d, J=7.57 Hz, 1H) 7.94 (d, J=8.06 Hz, 1H); MS [M+H]+ m/z 389.

Example 133

3-chloro-N-(3-{[(3-methoxyphenyl)thio]methyl}-1,2,4-thiadiazol-5-yl)-2-methylbenzenesulfonamide Prepared using method A.

1H NMR (400 MHz, METHANOL-D4) δ ppm 2.66 (s, 3H) 3.70 (s, 3H) 4.03 (s, 2H) 6.78 (dd, J=8.30, 2.44 Hz, 1H) 6.89 (m, 2H) 7.13 (t, J=8.06 Hz, 1H) 7.30 (t, J=8.06 Hz, 1H) 7.60 (d, J=7.81 Hz, 1H) 7.90 (d, J=8.06 Hz, 1H). MS (ES+) m/z 442 (M+H+)

Example 134

N-(3-isopropyl-1,2,4-thiadiazol-5-yl)naphthalene-2-sulfonamide

Prepared using method A.

1H NMR (400 MHz, CHLOROFORM-D) δ ppm 1.31 (d, J=6.84 Hz, 6H) 3.15 (m, 1H) 7.59 (m, 2H) 7.80 (m, 1H) 7.85 (m, 2H) 7.91 (d, J=8.06 Hz, 1H) 8.45 (m, 1H). MS [M+H]+ m/z 334.

Example 135

4-(3-chloro-2-cyanophenoxy)-N-(3-isopropyl-1,2,4-thiadiazol-5-yl)benzenesulfonamide Prepared using method A.

1H NMR (400 MHz, METHANOL-D4) δ ppm 1.27 (d, J=6.84 Hz, 6H) 2.95 (m, 1H) 7.03 (d, J=8.55 Hz, 1H) 7.24 (d, J=8.79 Hz, 2H) 7.43 (d, J=8.30 Hz, 1H) 7.61 (t, J=8.42 Hz, 1H) 7.95 (d, J=8.79 Hz, 2H); MS (ES+) m/z 435 (M+H+)

Example 136

N,N-diethyl-5-{[(4-phenoxyphenyl)sulfonyl]amino}-1,2,4-thiadiazole-3-carboxamide Prepared using method D.

1H NMR (400 MHz, CHLOROFORM-D) δ ppm 1.19 (t, J=7.08 Hz, 3H) 1.29 (t, J=6.96 Hz, 3H) 3.52 (q, J=7.08 Hz, 2H) 3.93 (d, J=6.92 Hz, 2H) 7.01 (d, J=8.79 Hz, 2H) 7.05 (d, J=7.81 Hz, 2H) 7.20 (t, J=7.45 Hz, 1H) 7.39 (t, J=7.81 Hz, 2H) 7.86 (d, J=8.79 Hz, 2H). MS [M+H]+ m/z 433.

Example 137

4-bromo-N-[3-(trichloromethyl)-1,2,4-thiadiazol-5-yl]benzenesulfonamide

Prepared using method C.

1H NMR (270 MHz, METHANOL-D4) δ ppm 7.67 (d, J=8.71 Hz, 2H) 7.82 (m, 2H). MS (ESI+) m/z 436 (M+H)+.

Example 138

(R)-3-chloro-N-(3-{1-[(3-methoxyphenyl)thio]ethyl}-1,2,4-thiadiazol-5-yl)-2-methylbenzenesulfonamide Prepared using method A.

1H NMR (400 MHz, CHLOROFORM-D) δ ppm 1.62 (d, J=7.08 Hz, 3H) 2.59 (m, 3H) 3.70 (m, 3H) 4.42 (q, J=7.08 Hz, 1H) 6.79 (m, 1H) 6.85 (m, 2H) 7.13 (m, 1H) 7.23 (m, 1H) 7.56 (m, 1H) 7.95 (m, 1H). MS m/z 456 (M+H)+

Example 139

3-chloro-N-(3-isopropyl-1,2,4-thiadiazol-5-yl)-2-methylbenzenesulfonamide

Prepared using method A.

1H NMR (400 MHz, CHLOROFORM-D) δ ppm 1.31 (d, J=6.84 Hz, 6H) 2.65 (s, 3H) 3.10 (m, 1H) 7.24 (m, 1H) 7.56 (dd, J=8.06, 1.22 Hz, 1H) 7.97 (dd, J=7.81, 1.22 Hz, 1H). MS [M+H]+ m/z 333.

Example 140

5-chloro-N-(3-isopropyl-1,2,4-thiadiazol-5-yl)-4-nitrothiophene-2-sulfonamide

Prepared using method A.

1H NMR (400 MHz, METHANOL-D4) δ ppm 1.29 (d, J=6.84 Hz, 6H) 2.98 (m, 1H) 7.99 (s, 1H); MS (ES+) m/z 369 (M+H+)

Example 141

4-phenoxy-N-{3-[(phenylthio)methyl]-1,2,4-thiadiazol-5-yl}benzenesulfonamide

Prepared using method A.

1H NMR (400 MHz, METHANOL-D4) δ ppm 4.02 (s, 2H) 6.99 (d, J=8.79 Hz, 2H) 7.04 (d, J=7.81 Hz, 2H) 7.20 (m, 4H) 7.31 (d, J=7.08 Hz, 2H) 7.39 (t, J=7.93 Hz, 2H) 7.82 (d, J=8.79 Hz, 2H); MS (ES+) m/z 456 (M+H+)

Example 142

3-chloro-2-methyl-N-{3-[(phenylthio)methyl]-1,2,4-thiadiazol-5-yl}benzenesulfonamide Prepared using method A.

1H NMR (400 MHz, DMSO-D6) δ ppm 2.60 (s, 3H) 4.12 (s, 2H) 7.20 (m, 1H) 7.28 (t, J=7.32 Hz, 2H) 7.36 (m, 3H) 7.67 (d, J=7.81 Hz, 1H) 7.84 (d, J=7.57 Hz, 1H); MS (ES+) m/z 412 (M+H+)

Example 143

N-(3-tert-butyl-1,2,4-thiadiazol-5-yl)naphthalene-2-sulfonamide

Prepared using method C.
1H NMR (400 MHz, DMSO-D6) δ ppm 1.24 (s, 9H) 7.67 (m, 2H) 7.81 (d, J=10.25 Hz, 1H) 8.02 (d, J=7.81 Hz, 1H) 8.10 (d, J=8.79 Hz, 1H) 8.18 (d, J=7.57 Hz, 1H) 8.49 (s, 1H). MS (ESI+) m/z 348 (H+1)

Example 144

(R)-3-chloro-2-methyl-N-[3-(1-phenoxyethyl)-1,2,4-thiadiazol-5-yl]benzenesulfonamide Prepared using method A.
1H NMR (400 MHz, CHLOROFORM-D) δ ppm 1.68 (d, J=6.59 Hz, 3H) 2.69 (m, 3H) 5.31 (q, J=6.59 Hz, 1H) 6.89 (m, 2H) 7.04 (m, 1H) 7.22 (m, 1H) 7.30 (m, 2H) 7.54 (m, 1H) 7.96 (m, 1H)
MS m/z 410 (M+H)$^+$

Example 145

3-chloro-2-methyl-N-[3-(trichloromethyl)-1,2,4-thiadiazol-5-yl]benzenesulfonamide Prepared using method A.
1H NMR (270 MHz, CHLOROFORM-D) δ ppm 2.41 (s, 3H) 6.99 (t, J=8.05 Hz, 1H) 7.45 (d, J=7.13 Hz, 1H) 7.71 (d, J=7.13 Hz, 1H). MS (ESI+) m/z 406 (M+H)$^+$.

Example 146

3-chloro-5-fluoro-N-(3-isopropyl-1,2,4-thiadiazol-5-yl)-2-methylbenzenesulfonamide Prepared using method A.
1H NMR (400 MHz, DMSO-D6) δ ppm 1.19 (s, 3H) 1.21 (s, 3H) 2.35 (s, 3H) 2.93 (m, 1H) 7.65 (d, J=9.77 Hz, 1H) 7.82 (d, J=7.57 Hz, 1H); MS [M+H]$^+$ m/z 350.

Example 147

(R)-3-chloro-2-methyl-N-(3-{1-[(1-methyl-1H-imidazol-2-yl)thio]ethyl}-1,2,4-thiadiazol-5-yl)benzenesulfonamide Prepared using method C.
1H NMR (400 MHz, CHLOROFORM-D) δ ppm 1.74 (m, 3H) 2.63 (m, 3H) 3.85 (m, 3H) 4.82 (m, 1H) 7.20 (t, J=7.57 Hz, 1H) 7.31 (m, 1H) 7.43 (m, 1H) 7.53 (d, J=7.57 Hz, 1H) 7.87 (d, J=7.08 Hz, 1H) MS m/z 430 (M+H)$^+$

Example 148

N-(3-cyclopropyl-1,2,4-thiadiazol-5-yl)-4-phenoxybenzenesulfonamide

Prepared using method A.
1H NMR (400 MHz, DMSO-D6) δ ppm 0.99 (m, 4H) 1.96 (m, 1H) 7.07 (d, J=9.03 Hz, 2H) 7.12 (d, J=9.01, 2 H) 7.24 (t, J=7.45 Hz, 1H) 7.45 (t, J=7.45, 2 H) 7.79 (d, J=8.79 Hz, 2H). MS (ESI+) m/z 374 (H+1)

Example 149

4-butoxy-N-(3-isopropyl-1,2,4-thiadiazol-5-yl)benzenesulfonamide

Prepared using method A.
1H NMR (400 MHz, METHANOL-D4) δ ppm 0.98 (m, 3H) 1.31 (m, 6H) 1.50 (m, 2H) 1.78 (m, 2H) 3.19 (m, 1H) 4.02 (m, 2H) 6.95 (m, 2H) 7.81 (m, 2H); MS [M+H]$^+$ m/z 356.

Example 150

(R)-3-chloro-2-methyl-N-[3-(1-{[3-(trifluoromethyl)phenyl]thio}ethyl)-1,2,4-thiadiazol-5-yl]benzenesulfonamide Prepared using method A.
1H NMR (400 MHz, CHLOROFORM-D) δ ppm 1.64 (d, J=7.08 Hz, 3H) 2.67 (m, 3H) 4.38 (q, J=7.08 Hz, 1H) 7.25 (m, 1H) 7.43 (m, 2H) 7.55 (m, 3H) 7.96 (m, 1H) MS m/z 494 (M+H)$^+$

Example 151

(R)-3-chloro-N-{3-[1-(3-fluorophenoxy)ethyl]-1,2,4-thiadiazol-5-yl}-2-methylbenzenesulfonamide Prepared using method A.
1H NMR (400 MHz, CHLOROFORM-D) δ ppm 1.68 (d, J=6.59 Hz, 3H) 2.69 (m, 3H) 5.30 (q, J=6.59 Hz, 1H) 6.66 (m, 2H) 6.75 (m, 1H) 7.25 (m, 2H) 7.55 (m, 1H) 7.96 (m, 1H). MS m/z 428 (M+H)$^+$

Example 152

(R)-N-(3-{1-[(3-fluorophenyl)thio]ethyl}-1,2,4-thiadiazol-5-yl)biphenyl-4-sulfonamide Prepared using method A.
1H NMR (400 MHz, CHLOROFORM-D) δ ppm 1.62 (d, J=7.08 Hz, 3H) 4.41 (td, J=7.32, 6.59 Hz, 1H) 6.98 (m, 3H) 7.20 (m, 1H) 7.41 (m, 3H) 7.53 (m, 2H) 7.65 (m, 2H) 7.96 (m, 2H) MS m/z 472 (M+H)$^+$

Example 153

4,5-dichloro-N-(3-isopropyl-1,2,4-thiadiazol-5-yl)thiophene-2-sulfonamide

Prepared using method A.
1H NMR (400 MHz, ACETONE-D6) δ ppm 1.32 (m, 6H) 3.10 (m, 1H) 7.52 (m, 1H). MS m/z 358 (M+H)$^+$

Example 154

N-(3-tert-butyl-1,2,4-thiadiazol-5-yl)biphenyl-4-sulfonamide

Prepared using method C.
1H NMR (400 MHz, DMSO-D6) δ ppm 1.25 (s, 9H) 7.43 (t, J=7.32 Hz, 1H) 7.50 (t, J=7.45 Hz, 2H) 7.71 (d, J=7.32 Hz, 2H) 7.87 (m, 4H). MS (ESI+) m/z 374 (H+1)

Example 155

(R)-3-chloro-N-{3-[1-(3,5-difluorophenoxy)ethyl]-1,2,4-thiadiazol-5-yl}-2-methylbenzenesulfonamide Prepared using method A.
1H NMR (400 MHz, METHANOL-D4) δ ppm 1.64 (d, J=6.59 Hz, 3H) 2.67 (s, 3H) 5.44 (q, J=6.43 Hz, 1H) 6.55 (tt, J=9.16, 2.08 Hz, 1H) 6.61 (dd, J=8.79, 1.95 Hz, 2H) 7.30 (t, J=7.93 Hz, 1H) 7.59 (d, J=7.81 Hz, 1H) 7.92 (d, J=8.06 Hz, 1H); MS (ES+) m/z 446 (M+H$^+$)

Example 156

3-chloro-N-(3-{[(3-fluorophenyl)thio]methyl}-1,2,4-thiadiazol-5-yl)-2-methylbenzenesulfonamide Prepared using method A.
1H NMR (400 MHz, DMSO-D6) δ ppm 2.60 (s, 3H) 4.20 (s, 2H) 7.02 (td, J=8.55, 2.20 Hz, 1H) 7.16 (d, J=8.06 Hz, 1H) 7.25 (dd, J=9.77, 1.95 Hz, 1H) 7.31 (dd, J=7.93, 6.47 Hz, 1H) 7.37 (t, J=8.18 Hz, 1H) 7.67 (d, J=8.06 Hz, 1H) 7.84 (d, J=8.06 Hz, 1H); MS (ES+) m/z 430 (M+H$^+$)

Example 157

3-chloro-N-(3-isobutyl-1,2,4-thiadiazol-5-yl)-2-methylbenzenesulfonamide

Prepared using method C.
1H NMR (400 MHz, METHANOL-D4) δ ppm 0.92 (m, 6H) 2.08 (m, 1H) 2.50 (d, J=7.32 Hz, 2H) 2.69 (s, 3H) 7.31 (t, J=8.06 Hz, 1H) 7.61 (d, J=8.06 Hz, 1H) 7.93 (d, J=7.81 Hz, 1H); MS [M+H]$^+$ m/z=346.

Example 158

3-chloro-N-(3-{[(2,4-difluorophenyl)thio]methyl}-1,2,4-thiadiazol-5-yl)-2-methylbenzenesulfonamide Prepared using method A.
1H NMR (400 MHz, METHANOL-D4) δ ppm 2.69 (s, 3H) 3.93 (s, 2H) 6.87 (td, J=8.42, 1.71 Hz, 1H) 6.95 (td, J=9.16, 2.69 Hz, 1H) 7.33 (t, J=7.93 Hz, 1H) 7.44 (m, 1H) 7.63 (d, J=7.57 Hz, 1H) 7.92 (d, J=7.81 Hz, 1H); MS (ES+) m/z 448 (M+H$^+$)

Example 159

2,4-dichloro-N-(3-isopropyl-1,2,4-thiadiazol-5-yl)-6-methylbenzenesulfonamide

Prepared using method A.
1H NMR (400 MHz, METHANOL-D4) δ ppm 1.28 (d, J=6.84 Hz, 6H) 2.73 (s, 3H) 2.97 (m, 1H) 7.36 (s, 1H) 7.48 (s, 1H); MS (ES+) m/z 366 (M+H$^+$)

Example 160

2,4,6-trichloro-N-(3-isopropyl-1,2,4-thiadiazol-5-yl)benzenesulfonamide

Prepared using method A.
1H NMR (400 MHz, METHANOL-D4) δ ppm 1.29 (d, J=6.84 Hz, 6H) 2.98 (m, 1H) 7.63 (s, 2H); MS (ES+) m/z 386 (M+H$^+$)

Example 161

(R)-3-chloro-N-(3-{1-[(3-fluorophenyl)thio]ethyl}-1,2,4-thiadiazol-5-yl)-2-methylbenzenesulfonamide Prepared using method A.
1H NMR (400 MHz, CHLOROFORM-D) δ ppm 1.63 (d, J=7.08 Hz, 3H) 2.62 (m, 3H) 4.44 (q, J=7.08 Hz, 1H) 6.97 (m, 1H) 7.04 (m, 2H) 7.21 (m, 1H) 7.25 (m, 1H) 7.57 ) dd, J=8.06, 1.22 Hz, 1H) 7.95 (dd, J=8.06, 1.22 Hz, 1H) MS m/z 444 (M+H)$^+$

Example 162

(R)-3-chloro-2-methyl-N-{3-[1-(phenylthio)ethyl]-1,2,4-thiadiazol-5-yl}benzenesulfonamide Prepared using method A.
1H NMR (400 MHz, CHLOROFORM-D) δ ppm 1.62 (d, J=7.08 Hz, 3H) 2.63 (m, 3H) 4.34 (q, J=7.08 Hz, 1H) 7.26 (m, 6H) 7.56 (m, 1H) 7.96 (m, 1H) MS m/z 426 (M+H)$^+$

Example 163

3-chloro-N-(3-{[(3,4-difluorophenyl)thio]methyl}-1,2,4-thiadiazol-5-yl)-2-methylbenzenesulfonamide Prepared using method A.
1H NMR (400 MHz, METHANOL-D4) δppm 2.67 (s, 3H) 4.05 (s, 2H) 7.16 (m, 2H) 7.33 (m, 2H) 7.62 (d, J=7.81 Hz, 1H) 7.91 (d, J=7.81 Hz, 1H); MS (ES+) m/z 448 (M+H$^+$)

Example 164

5-fluoro-2-methyl-N-[3-(2-thienyl)-1,2,4-thiadiazol-5-yl]benzenesulfonamide

Prepared using method A.
1H NMR (400 MHz, DMSO-D6) δ ppm 2.51 (s, 3H) 7.16 (dd, J=5.01, 3.78 Hz, 1H) 7.35 (td, J=8.36, 2.81 Hz, 1H) 7.41 (dd, J=8.55, 5.62 Hz, 1H) 7.60 (dd, J=8.85, 2.75 Hz, 1H) 7.77 (d, J=3.78 Hz, 1H) 7.78 (m, 1H). MS (ESI+) m/z 356 (H+1)

Example 165

N-{3-[(diethylamino)methyl]-1,2,4-thiadiazol-5-yl}-4-phenoxybenzenesulfonamide trifluoroacetate Prepared using method C.
1H NMR (400 MHz, METHANOL-D4) δ ppm 1.33 (t, J=7.32 Hz, 6H) 3.30 (m, 4H) 4.31 (s, 2H) 7.04 (m, 4H) 7.21 (t, J=7.45 Hz, 1H) 7.41 (m, 2H) 7.87 (m, 2H); MS [M+H]$^+$ m/z=419.

Example 166

4-tert-butyl-N-(3-phenyl-1,2,4-thiadiazol-5-yl)benzenesulfonamide

Prepared using method C.
1H NMR (270 MHz, DMSO-D6) δ ppm 1.24 (s, 9H) 7.36 (m, 3H) 7.44 (d, J=8.44 Hz, 2H) 7.67 (d, J=8.44 Hz, 2H) 8.01 (dd, J=7.78, 1.72 Hz, 2H). MS (ESI+) m/z 374 (M+H)$^+$.

Example 167

4-chloro-N-(3-morpholin-4-yl-1,2,4-thiadiazol-5-yl)-3-nitrobenzenesulfonamide

Prepared using method C.
1H NMR (400 MHz, DMSO-D6) δ ppm 3.39 (m, 4H) 3.62 (m, 4H) 7.95 (d, J=8.54 Hz, 1H) 8.05 (m, 1H) 8.41 (m, 1H). MS (ESI+) m/z 406 (H+1)

Example 168

N-[3-(3-furyl)-1,2,4-thiadiazol-5-yl]-4-methylbenzenesulfonamide

Prepared using method C.
1H NMR (400 MHz, DMSO-D6) δ ppm 2.36 (s, 3H) 6.93 (d, J=1.46 Hz, 1H) 7.37 (d, J=8.06 Hz, 2H) 7.72 (d, J=8.30 Hz, 2H) 7.83 (s, 1H) 8.31 (s, 1H); MS [M +H]$^+$ m/z 322.

Example 169

4-methyl-N-[3-(3-thienyl)-1,2,4-thiadiazol-5-yl]benzenesulfonamide

Prepared using method C.
1H NMR (400 MHz, DMSO-D6) δ ppm 2.35 (s, 3H) 7.37 (d, J=8.06 Hz, 2H) 7.60 (dd, J=5.13, 0.98 Hz, 1H) 7.69 (m, 1H) 7.72 (d, J=8.30 Hz, 2H) 8.24 (d, J=1.71 Hz, 1H); MS [M+H]$^+$ m/z=338.

Example 170

3-chloro-2-methyl-N-{3-[2-(4-methylpiperazin-1-yl)ethyl]-1,2,4-thiadiazol-5-yl}benzenesulfonamide Prepared using method C.
1H NMR (400 MHz, METHANOL-D4) δ ppm 2.7 (m, 3H) 2.9 (s, 3H) 3.0 (t, J=6.8 Hz, 2H) 3.2 (m, 6H) 3.4 (m, 4H) 7.3 (m, 1H) 7.6 (d, J=8.1 Hz, 1H) 7.9 (d, J=7.9 Hz, 1H); MS (ESI+) m/z 416 (M+H).

Example 171

N-[3-(2-ethoxyethyl)-1,2,4-thiadiazol-5-yl]-4-phenoxybenzenesulfonamide

Prepared using method C.
1H NMR (400 MHz, CHLOROFORM-D) δ ppm 1.31 (t, J=7.32 Hz, 3H) 3.06 (t, J=6.96 Hz, 2H) 3.26 (m, 2H) 4.45 (t, J=6.96 Hz, 2H) 7.03 (m, 2H) 7.08 (m, 2H) 7.24 (m, 1H) 7.42 (m, 2H). MS [M+H]$^+$ m/z=406.

Example 172

3-chloro-N-[3-(2-ethoxyethyl)-1,2,4-thiadiazol-5-yl]-2-methylbenzenesulfonamide

Prepared using method C.
1H NMR (400 MHz, CHLOROFORM-D) δ ppm 1.31 (t, J=7.20 Hz, 3H) 2.55 (s, 3H) 3.04 (t, J=6.47 Hz, 2H) 3.25 (m, 2H) 4.47 (t, J=6.47 Hz, 2H) 7.28 (m, 1H) 7.61 dd (J=7.93, 1.10 Hz, 1H) 7.94 (dd, J=7.94, 1.10 Hz, 1H).

Example 173

3-chloro-4-fluoro-N-(3-phenyl-1,2,4-thiadiazol-5-yl)benzenesulfonamide

Prepared using method C.
1H NMR (270 MHz, DMSO-D6) δ ppm 7.45 (m, 3H) 7.56 (d, J=8.97 Hz, 1H) 7.81 (m, 1H) 7.92 (dd, J=6.99, 2.24 Hz, 1H) 8.02 (dd, J=6.60, 3.17 Hz, 2H). MS (ESI+) m/z 370 (M+H)$^+$.

Example 174

4-fluoro-N-(3-phenyl-1,2,4-thiadiazol-5-yl)benzenesulfonamide

Prepared using method C.
1H NMR (270 MHz, DMSO-D6) δ ppm 7.32 (m, 2H) 7.44 (m, 3H) 7.85 (m, 2H). MS (ESI+) m/z 336 (M+H)$^+$.

Example 175

N-(3-isopropyl-1,2,4-thiadiazol-5-yl)-2,5-bis(2,2,2-trifluoroethoxy)benzenesulfonamide Prepared using method A.
1H NMR (400 MHz, METHANOL-D4) δ ppm 1.27 (d, J=7.08 Hz, 6H) 2.95 (m, 1H) 6.56 (m, 1H) 7.76 (d, J=1.22 Hz, 1H) 7.95 (m, 4H) 8.33 (d, J=2.44 Hz, 1H); MS (ES+) m/z 350 (M+H$^+$)

Example 176

N-[3-(morpholin-4-ylmethyl)-1,2,4-thiadiazol-5-yl]-4-phenoxybenzenesulfonamide trifluoroacetate Prepared using method C.
1H NMR (400 MHz, METHANOL-D4) δ ppm 3.21 (m, 4H) 3.86 (m, 4H) 4.16 (s, 2H) 7.04 (m, 4H) 7.21 (t, J=7.45 Hz, 1H) 7.41 (t, J=7.93 Hz, 2H) 7.86 (d, J=8.79 Hz, 2H); MS [M+H]$^+$ m/z=433.

Comparison Example 177

4-methoxy-N-(3-phenyl-1,2,4-thiadiazol-5-yl)benzenesulfonamide

Prepared using method C.
1H NMR (270 MHz, METHANOL-D4) δ ppm 3.78 (s, 3H) 6.96 (m, 2H) 7.39 (m, 3H) 7.84 (d, J=8.97 Hz, 2H) 7.99 (m, 2H). MS (ESI+) m/z 348 (M+H)$^+$.

Example 178

4-methyl-N-(3-methyl-1,2,4-thiadiazol-5-yl)benzenesulfonamide

Prepared using method C.
1H NMR (270 MHz, METHANOL-D4) δ ppm 2.27 (s, 3H) 2.36 (s, 3H) 7.26 (d, J=7.92 Hz, 2H) 7.73 (d, J=8.44 Hz, 2H). MS (ESI+) m/z 270 (M+H)$^+$.

Example 179

N-(3-isopropyl-1,2,4-thiadiazol-5-yl)-1,2-dimethyl-1H-imidazole-4-sulfonamide

Prepared using method A.
1H NMR (400 MHz, CHLOROFORM-D) δ ppm 1.29 (d, J=6.84 Hz, 6H) 2.59 (m, 3H) 3.07 (m, 1H) 3.73 (m, 3H) 7.51 (m, 1H) MS m/z 302 (M+H)$^+$

Example 180

N-(4-{[(5-{[(3-chloro-2-methylphenyl)sulfonyl]amino}-1,2,4-thiadiazol-3-yl)methyl]sulfonyl}phenyl)acetamide Prepared using method A.

1H NMR (400 MHz, methanol-D4) δ ppm 2.16 (s, 3H) 2.67 (s, 3H) 4.57 (s, 2H) 7.33 (t, J=8.06 Hz, 1H) 7.63 (d, J=8.06 Hz, 1H) 7.68 (d, J=8.79 Hz, 2H) 7.77 (m, 2H) 7.92 (d, J=8.06 Hz, 1H); MS (ES+) m/z 501 (M+H$^+$)

Example 181

N-(3-phenyl-1,2,4-thiadiazol-5-yl)naphthalene-1-sulfonamide

Prepared using method C.

1H NMR (270 MHz, DMSO-D6) δ ppm 7.35 (m, 3H) 7.55 (d, J=7.65 Hz, 1H) 7.60 (dd, J=5.28, 1.58 Hz, 1H) 7.65 (m, 1H) 7.99 (m, 4H) 8.10 (dd, J=7.26, 1.19 Hz, 1H) 8.85 (m, 1H). MS (ESI+) m/z 368 (M+H)$^+$.

Example 182

N-(3-phenyl-1,2,4-thiadiazol-5-yl)thiophene-2-sulfonamide

Prepared using method C.

1H NMR (270 MHz, DMSO-D6) δ ppm 6.98 (dd, J=5.01, 3.69 Hz, 1H) 7.39 (m, 4H) 7.61 (dd, J=5.01, 1.32 Hz, 1H) 8.03 (m, 2H). MS (ESI+) m/z 324 (M+H)$^+$.

Example 183

2-nitro-N-(3-phenyl-1,2,4-thiadiazol-5-yl)benzenesulfonamide

Prepared using method C.

1H NMR (270 MHz, DMSO-D6) δ ppm 7.39 (m, 3H) 7.65 (m, 2H) 7.73 (m, 1H) 7.96 (m, 1H) 8.03 (m, 2H). MS (ESI+) m/z 363 (M+H)$^+$.

Example 184

3-chloro-N-{3-[(diethylamino)methyl]-1,2,4-thiadiazol-5-yl}-2-methylbenzenesulfonamide trifluoroacetate Prepared using method C.

1H NMR (400 MHz, METHANOL-D4) δ ppm 1.32 (t, J=7.32 Hz, 6H) 2.70 (s, 3H) 3.30–3.40 (m, disturbed by solvent peak, 4H) 7.29 (t, J=7.93 Hz, 1H) 7.58 (d, J=7.81 Hz, 1H) 7.96 (d, J=7.81 Hz, 1H); MS [M+H]$^+$ m/z=375.

Example 185

5-fluoro-2-methyl-N-(3-morpholin-4-yl-1,2,4-thiadiazol-5-yl)benzenesulfonamide

Prepared using method C.

1H NMR (400 MHz, DMSO-D6) δ ppm 2.52 (s, 3H) 3.38 (m, 4H) 3.62 (m, 4H) 7.41 (m, 2H) 7.59 (m, 1H). MS (ESI+) m/z 359 (H+1)

Comparison Example 186

4-methoxy-N-(3-methyl-1,2,4-thiadiazol-5-yl)benzenesulfonamide

Prepared using method C.

1H NMR (270 MHz, METHANOL-D4) δ ppm 2.27 (s, 3H) 3.80 (s, 3H) 6.95 (d, J=8.97 Hz, 2H) 7.78 (d, J=8.97 Hz, 2H). MS (ESI+) m/z 286 (M+H)$^+$.

Example 187

4-tert-butyl-N-(3-methyl-1,2,4-thiadiazol-5-yl)benzenesulfonamide

Prepared using method C.

1H NMR (270 MHz, METHANOL-D4) δ ppm 1.30 (s, 9H) 2.28 (s, 3H) 4.91 (s, 1H) 7.51 (d, J=8.97 Hz, 2H) 7.78 (d, J=8.71 Hz, 2H).

Example 188

4-cyano-N-(3-methyl-1,2,4-thiadiazol-5-yl)benzenesulfonamide

Prepared using method C.

1H NMR (270 MHz, METHANOL-D4) δ ppm 2.28 (s, 3H) 7.83 (d, J=8.71 Hz, 2H) 8.01 (d, J=8.44 Hz, 2H)

Example 189

N-(5-ethyl-1,3,4-thiadiazol-2-yl)-4-(trifluoromethoxy)benzenesulfonamide

Example 190

4-chloro-N-(5-isopropyl-1,3,4-thiadiazol-2-yl)benzenesulfonamide

Example 191

4-fluoro-N-[5-(trifluoromethyl)-1,3,4-thiadiazol-2-yl]benzenesulfonamide

Comparison Example 192

4-chloro-N-(4-{[(5-ethyl-1,3,4-thiadiazol-2-yl)amino]sulfonyl}phenyl)-3-nitrobenzamide

Comparison Example 193

N-[4-({[5-(butylthio)-1,3,4-thiadiazol-2-yl]amino}sulfonyl)phenyl]acetamide

Example 194

5-{[(3-chloro-2-methylphenyl)sulfonyl]amino}-1,3,4-thiadiazole-2-carboxylic acid Prepared using method C.

1H NMR (270 MHz, METHANOL-D4) δ ppm 3.34 (s, 3H) 7.19 (t, J=7.65 Hz, 1H) 7.45 (dd, J=8.18, 1.06 Hz, 1H) 7.89 (dd, J=7.92, 1.06 Hz, 1H)

Example 195

N-(4-{[(5-ethyl-1,3,4-thiadiazol-2-yl)amino]sulfonyl}phenyl)-4-fluorobenzamide

Prepared using method C.
$^1$H NMR (270 MHz, DMSO-D6) δ ppm 1.18–1.23 (m, 3H) 2.82 (q, J=7.59 Hz, 2H) 7.34–7.41 (m, 2H) 7.76–7.79 (m, 2H) 7.92–7.95 (m, 2H) 8.01–8.06 (m, 2H) 10.58 (s, 1H). MS (ESI+) m/z 407 (M+H)$^+$.

Example 196

N-(5-isopropyl-1,3,4-thiadiazol-2-yl)-4-nitrobenzenesulfonamide

Prepared using method A.
$^1$H NMR (270 MHz, MeOH-D) δ ppm 8.36 (d, J=8.66 Hz, 2H), 8.08 (d, J=8.66 Hz, 2H), 3.20–3.11 (m, 1H), 1.34 (d, J=6.93 Hz, 6H). MS (ESI+) m/z 329 (M+H)$^+$

Comparison Example 197

N-[4-({[5-(2,2-dimethylpropyl)-1,3,4-thiadiazol-2-yl]amino}sulfonyl)phenyl]acetamide Prepared using method C.
$^1$H NMR (270 MHz, DMSO-D6) δ ppm 0.95 (s, 9H) 2.06 (s, 3H) 2.70 (s, 2H) 7.71–7.69 (m, 4H) 10.29 (s, 2H). MS (ESI+) m/z 369 (M+H)$^+$.

Example 198

4-bromo-N-[5-(methoxymethyl)-1,3,4-thiadiazol-2-yl]benzenesulfonamide

Example 199

N-(5-isopropyl-1,3,4-thiadiazol-2-yl)-N-methylbiphenyl-4-sulfonamide

Prepared using method A.
$^1$H NMR (270 MHz, CHCl3-D) δ ppm 8.00–7.96 (m, 2H), 7.69–7.65 (m, 2H), 7.59–7.56 (m, 2H), 7.48–7.38 (m, 3H), 3.12–3.05 (m, 1H), 1.32 (d, J=6.93 Hz, 6H).

MS (ESI+) m/z 374 (M+H)$^+$

Comparison Example 200

3-(trifluoromethyl)-N-[5-(trifluoromethyl)-1,3,4-thiadiazol-2-yl]benzenesulfonamide

Example 201

N-[5-(4-tert-butylphenyl)-1,3,4-thiadiazol-2-yl]-3-chloro-2-methylbenzenesulfonamide Prepared using method C.
$^1$H NMR (270 MHz, METHANOL-D4) δ ppm 1.33 (s, 9H) 2.72 (s, 3H) 7.31 (t, J=8.04 Hz, 1H) 7.52 (d, J=8.66 Hz, 2H) 7.59 (d, J=8.16 Hz, 1H) 7.70 (d, J=8.66, 2 H) 7.98 (d, J=7.92 Hz, 1H). MS (M+1) 422

Comparison Example 202

4-({[(4-chlorophenyl)amino]carbonyl}amino)-N-(5-ethyl-1,3,4-thiadiazol-2-yl)benzenesulfonamide

Example 203

3-chloro-2-methyl-N-(5-phenyl-1,3,4-thiadiazol-2-yl)benzenesulfonamide

Prepared using method C.
1H NMR (270 MHz, METHANOL-D4) δ ppm 2.72 (s, 3H) 7.32 (t, J=7.92 Hz, 1H) 7.47–7.54 (m, 3H) 7.61 (d, J=7.42 Hz, 1H) 7.77–7.84 (m, 2H) 7.99 (d, J=6.93 Hz, 1H). MS (ESI+) m/z 366 (M+H)$^+$

Example 204

2-(1,3-benzothiazol-2-ylthio)-N-(4-{[(5-ethyl-1,3,4-thiadiazol-2-yl)amino]sulfonyl}phenyl)acetamide

Example 205

5-fluoro-N-(5-isopropyl-1,3,4-thiadiazol-2-yl)-2-methylbenzenesulfonamide

Prepared using method A.
$^1$H NMR (270 MHz, Chloroform-D) δ ppm 7.73 (dd, J=8.1, 2.7 Hz, 1H), 7.26–7.23 (m, 1H), 7.21–7.07 (m, 1H), 3.13–3.04 (m, 1H), 2.59 (s, 3H), 1.33 (d, J=5.4 Hz, 6H). MS (ESI+) m/z 316 (M+H)$^+$

Example 206

N-(5-methyl-1,3,4-thiadiazol-2-yl)-4-(trifluoromethoxy)benzenesulfonamide

Example 207

4-methyl-N-[5-(trifluoromethyl)-1,3,4-thiadiazol-2-yl]benzenesulfonamide

Example 208

3-chloro-2-methyl-N-[5-(2-methylpyridin-3-yl)-1,3,4-thiadiazol-2-yl]benzenesulfonamide Prepared using method C.
$^1$H NMR (270 MHz, METHANOL-D4) δ ppm 2.73 (d, J=4.95 Hz, 6H) 7.32 (t, J=8.04 Hz, 1H) 7.36–7.45 (m, 1H) 7.61 (d, J=7.92 Hz, 1H) 8.00 (t, J=7.92 Hz, 2H) 8.53 (d, J=3.71 Hz, 1H). MS (M+1) 381

Example 209

3-chloro-2-methyl-N-[5-(pyridin-3-ylmethyl)-1,3,4-thiadiazol-2-yl]benzenesulfonamide Prepared using method C.
$^1$H NMR (270 MHz, METHANOL-D4) δ ppm 2.68 (s, 3H) 4.37 (s, 2H) 7.29 (t, J=8.04 Hz, 1H) 7.60 (dd, J=8.04, 1.11 Hz, 1H) 7.78 (dd, J=7.42, 5.69 Hz, 1H) 7.91 (dd, J=7.92, 1.24 Hz, 1H) 8.25 (d, J=7.92 Hz, 1H) 8.69 (d, J=19.30 Hz, 2H). MS (M+1) 3.81

Example 210

4-chloro-N-[5-(trifluoromethyl)-1,3,4-thiadiazol-2-yl]benzenesulfonamide

Example 211

3-chloro-2-methyl-N-{5-[(4-nitrophenoxy)methyl]-1,3,4-thiadiazol-2-yl}benzenesulfonamide Prepared using method C.
$^1$H NMR (270 MHz, METHANOL-D4) δ ppm 2.60 (s, 3H) 5.28 (s, 2H) 7.11 (d, J=9.40 Hz, 2H) 7.21 (t, J=8.04 Hz, 1H) 7.51 (d, J=6.93 Hz, 1H) 7.84 (d, J=7.92 Hz, 1H) 8.15 (d, J=9.15 Hz, 2H). MS (M+1) 441

Comparison Example 212

N-(5-isobutyl-1,3,4-thiadiazol-2-yl)-4-methoxybenzenesulfonamide

Comparison Example 213

N-(5-phenyl-1,3,4-thiadiazol-2-yl)-3-(trifluoromethyl)benzenesulfonamide

Prepared using method C.
$^1$H NMR (270 MHz, METHANOL-D4) δ ppm 7.35–7.49 (m, 3H) 7.57–7.91 (m, 4H) 8.02–8.14 (m, 2H). MS (ESI+) m/z 386 (M+H)$^+$

Comparison Example 214

4-(1,3-dioxo-1,3-dihydro-2H-isoindol-2-yl)-N-(5-ethyl-1,3,4-thiadiazol-2-yl)benzenesulfonamide

Example 215

3-chloro-2-methyl-N-[5-(trifluoromethyl)-1,3,4-thiadiazol-2-yl]benzenesulfonamide Prepared using method C.
1H NMR (270 MHz, METHANOL-D4) δ ppm 2.69 (s, 3H) 7.32 (t, J=8.05 Hz, 1H) 7.61 (d, J=8.18 Hz, 1H) 7.94 (dd, J=8.05, 1.19 Hz, 1H). $^{13}$C NMR (67.5 MHz, METHANOL-D4) δ ppm 17.57, 127.73, 127.95, 134.75, 136.39, 137.90, 142.57. MS (ESI+) m/z 358 (M+H)$^+$. HRMS (EI) calcd for $C_{10}H_7ClF_3N_3O_2S_2$: 356.9620. found 356.962

Comparison Example 216

N-(5-cyclohexyl-1,3,4-thiadiazol-2-yl)-4-methoxybenzenesulfonamide

Example 217

4-phenoxy-N-(5-phenyl-1,3,4-thiadiazol-2-yl)benzenesulfonamide

Prepared using method C.
$^1$H NMR (270 MHz, METHANOL-D4) δ ppm 6.91–7.01 (m, 4H) 7.07–7.16 (m, 1H) 7.32 (m, 2H) 7.41 (m, 3H) 7.75 (m, 4H). MS (ESI+) m/z 410 (M+H)$^+$

Example 218

4-bromo-N-(5-phenyl-1,3,4-thiadiazol-2-yl)benzenesulfonamide

Prepared using method C.
$^1$H NMR (270 MHz, METHANOL-D4) δ ppm 7.39–7.45 (m, 3H) 7.58–7.65 (m, 2H) 7.68–7.77 (m, 4H). MS (ESI+) m/z 397 (M+H)$^+$

Example 219

4-bromo-N-(5-isopropyl-1,3,4-thiadiazol-2-yl)benzenesulfonamide

Example 220

N-[5-(4-methoxybenzyl)-1,3,4-thiadiazol-2-yl]-4-nitrobenzenesulfonamide

Comparison Example 221

N-(5-isopropyl-1,3,4-thiadiazol-2-yl)-3-(trifluoromethyl)benzenesulfonamide

Prepared using method A.
$^1$H NMR (270 MHz, Chloroform-D) δ ppm 8.13 (s, 3H), 7.58–7.54 (m, 1H), 6.82 (d, J=8.1 Hz, 1H), 3.20–3.10 (m, 1H), 1.35 (d, J=5.4 Hz, 6H). MS (ESI+) m/z 352 (M+H)$^+$

Example 222

3-chloro-N-(5-ethyl-1,3,4-thiadiazol-2-yl)-2-methylbenzenesulfonamide

Prepared using method C.
1H NMR (270 MHz, METHANOL-D4) δ ppm 1.27 (t, J=7.52 Hz, 3H) 2.69 (s, 3H) 2.82 (q, J=7.39 Hz, 2H) 7.30 (t, J=7.92 Hz, 1H) 7.59 (m, 1H) 7.93 (dd, J=7.92, 1.06 Hz, 1H). $^{13}$C NMR (67.5 MHz, METHANOL-D4) δ ppm 12.81, 17.59, 25.12, 127.69, 127.78, 134.27, 136.24, 137.81, 143.26, 162.08. MS (ESI+) m/z 318 (M+H)$^+$

Example 223

Ethyl [(5-{[(3-chloro-2-methylphenyl)sulfonyl]amino}-1,3,4-thiadiazol-2-yl)thio]acetate Prepared using method B.
1H NMR (500 MHz, DMSO-D6) δ ppm 1.20 (t, J=7.01 Hz, 3H) 2.63 (m, 4H) 4.16 (m, 3H) 7.45 (t, J=7.92 Hz, 1H) 7.75 (d, J=7.92 Hz, 1H) 7.91 (d, J=7.92 Hz, 1H).

Example 224

3,4-dichloro-N-[5-(trifluoromethyl)-1,3,4-thiadiazol-2-yl]benzenesulfonamide

Example 225

3-chloro-N-(5-isopropyl-1,3,4-thiadiazol-2-yl)-2-methylbenzenesulfonamide

Prepared using method A.
$^1$H NMR (270 MHz, Chloroform-D) δ ppm 7.95 (d, J=8.1 Hz, 1H), 7.52–7.49 (m, 1H), 7.25–7.17 (m, 1H), 3.13–3.03 (m, 1H), 2.65 (s, 3H), 1.30 (d, J=5.4 Hz, 6H). MS (ESI+) m/z 332 (M+H)$^+$

Example 226

4-fluoro-N-(5-isobutyl-1,3,4-thiadiazol-2-yl)benzenesulfonamide

Example 227

3-chloro-N-[5-(2-ethoxyethyl)-1,3,4-thiadiazol-2-yl]-2-methylbenzenesulfonamide

Example 228

2,4,6-trichloro-N-(5-phenyl-1,3,4-thiadiazol-2-yl)benzenesulfonamide

Prepared using method C.
$^1$H NMR (270 MHz, METHANOL-D4) δ ppm 7.42 (m, 4H) 7.55 (s, 2H) 7.74 (d, J=7.92 Hz, 1H). MS (ESI+) m/z 420 (M+H)$^+$

Example 229

N-(5-phenyl-1,3,4-thiadiazol-2-yl)naphthalene-2-sulfonamide

Prepared using method C.
$^1$H NMR (270 MHz, METHANOL-D4) δ ppm 7.38–7.45 (m, 4H) 7.59–7.65 (m, 3H) 7.69–7.76 (m, 5H). MS (ESI+) m/z 368 (M+H)$^+$

Comparison Example 230

2-(2,4-dichlorophenoxy)-N-(4-{[(5-ethyl-1,3,4-thiadiazol-2-yl)amino]sulfonyl}phenyl)acetamide

Example 231

3,4-dichloro-N-(5-cyclopropyl-1,3,4-thiadiazol-2-yl)benzenesulfonamide

Example 232

4-bromo-N-[5-(4-methoxybenzyl)-1,3,4-thiadiazol-2-yl]benzenesulfonamide

Comparison Example 233

N-(5-cyclohexyl-1,3,4-thiadiazol-2-yl)benzenesulfonamide

Prepared using method A.
$^1$H NMR (270 MHz, DMSO-D) δ ppm 7.78–7.76 (m, 2H), 7.56–7.53 (m, 3H), 3.45–3.25 (m, 2H), 2.90–3.75 (m, 1H), 2.01–2.90 (m, 2H), 1.80–1.50 (m, 2H), 1.45–1.10 (m, 4H). MS (ESI+) m/z 324 (M+H)$^+$

Example 234

4-bromo-N-[5-(trifluoromethyl)-1,3,4-thiadiazol-2-yl]benzenesulfonamide

Example 235

N-(5-cyclohexyl-1,3,4-thiadiazol-2-yl)-4-nitrobenzenesulfonamide

Example 236

N-(5-isobutyl-1,3,4-thiadiazol-2-yl)-4-methylbenzenesulfonamide

Example 237

N-(5-isobutyl-1,3,4-thiadiazol-2-yl)-4-nitrobenzenesulfonamide

Example 238

4-[(5-chloro-2-hydroxybenzyl)amino]-N-(5-ethyl-1,3,4-thiadiazol-2-yl)benzenesulfonamide

Example 239

4-chloro-N-[5-(4-chlorobenzyl)-1,3,4-thiadiazol-2-yl]benzenesulfonamide

Comparison Example 240

N-(5-tert-butyl-1,3,4-thiadiazol-2-yl)benzenesulfonamide

Prepared using method C.
1H NMR (270 MHz, METHANOL-D4) δ ppm 1.36 (s, 9H) 7.54 (m, 3H) 7.86 (m, 2H). $^{13}$C NMR (67.5 MHz, METHANOL-D4) δ ppm 30.05, 37.50, 127.20, 130.02, 133.55, 143.31, 169.51. MS (ESI+) m/z 298 (M+H)$^+$.

Example 241

N-(5-cyclohexyl-1,3,4-thiadiazol-2-yl)-4-methylbenzenesulfonamide

Example 242

N-[5-(4-chlorobenzyl)-1,3,4-thiadiazol-2-yl]-4-nitrobenzenesulfonamide

Example 243

N-[5-(ethylthio)-1,3,4-thiadiazol-2-yl]-4-methylbenzenesulfonamide

Prepared using method C.
1H NMR (270 MHz, CHLOROFORM-D) δ ppm 1.41 (t, J=7.39 Hz, 3H) 2.39 (s, 3 H) 3.15 (q, J=7.39 Hz, 2H) 7.24–7.27 (m, 2H) 7.76–7.79 (m, 2H). MS (ESI+) m/z 316, 318, 653 (M+H)$^+$.

Example 244

N-(5-isopropyl-1,3,4-thiadiazol-2-yl)-4-phenoxybenzenesulfonamide

Prepared using method A.
$^1$H NMR (270 MHz, Chloroform-D) δ ppm 7.89–7.83 (m, 2H), 7.40–7.33 (m, 2H), 7.20–7.15 (m, 1H), 7.05–6.94 (m, 4H), 3.17–3.06 (m, 1H), 1.32 (d, J=5.4 Hz, 6H). MS (ESI+) m/z 376 (M+H)$^+$

Example 245

4-bromo-N-[5-(ethylthio)-1,3,4-thiadiazol-2-yl]benzenesulfonamide

Example 246

3-chloro-N-{5-[(4-fluorophenoxy)methyl]-1,3,4-thiadiazol-2-yl}-2-methylbenzenesulfonamide Prepared using method C.
$^1$H NMR (270 MHz, METHANOL-D4) δ ppm 2.60 (s, 3H) 5.11 (s, 2H) 5.42 (s, 1H) 6.94 (m, 4H) 7.22 (t, J=8.04 Hz, 1H) 7.51 (d, J=7.92 Hz, 1H) 7.84 (d, J=7.92 Hz, 1H). Ms (M+1) 414

Example 247

N-(5-isopropyl-1,3,4-thiadiazol-2-yl)naphthalene-2-sulfonamide

Prepared using method A.
$^1$H NMR (270 MHz, Chloroform-D) δ ppm 8.49 (s, 1H), 7.94–7.82 (m, 4H), 7.61–7.54 (m, 2H), 3.12–3.04 (m, 1H), 1.31 (d, J=5.4 Hz, 6H). MS (ESI+) m/z 334 (M+H)$^+$

Example 248

3-chloro-N-{5-[(4-chlorophenoxy)methyl]-1,3,4-thiadiazol-2-yl}-2-methylbenzenesulfonamide Prepared using method C.
$^1$H NMR (270 MHz, METHANOL-D4) δ ppm 2.69 (s, 3H) 5.22 (s, 2H) 6.97–7.05 (m, 2H) 7.25–7.35 (m, 3H) 7.60 (dd, J=8.04, 1.11 Hz, 1H) 7.93 (dd, J=7.92, 1.24 Hz, 1H). MS (M+1) 430

Example 249

4-bromo-N-(5-tert-butyl-1,3,4-thiadiazol-2-yl)benzenesulfonamide

Prepared using method C.
1H NMR (270 MHz, METHANOL-D4) δ ppm 1.36 (s, 9H) 7.69 (m, 2H) 7.76 (m, 2H). 13C NMR (67.5 MHz, METHANOL-D4) δ ppm 30.05, 37.52, 127.95, 129.02, 133.26, 142.61, 162.77, 169.64. MS (ESI+) m/z 376 (M+H)$^+$. HRMS (ESI) calcd for $C_{12}H_{14}BrN_3O_2S_2$: 374.9711. Found 374.9712.

Example 250

N-(5-tert-butyl-1,3,4-thiadiazol-2-yl)-3-chloro-2-methylbenzenesulfonamide

Prepared using method C.
1H NMR (270 MHz, METHANOL-D4) δ ppm 1.35 (s, 9H) 7.31 (t, J=7.92 Hz, 1H) 7.60 (m, 1H) 7.94 (d, J=7.65 Hz, 1H). 13C NMR (67.5 MHz, METHANOL-D4) δ ppm 16.23, 28.73, 36.40, 125.76, 126.00, 130.92, 134.27, 135.68, 145.31, 168.69, 170.59. MS (ESI+) m/z 346 (M+H)$^+$. HRMS (ESI) calcd for $C_{13}H_{16}ClN_3O_2S_2$: 346.0372. Found 346.0369.

Example 251

N-(5-cyclohexyl-1,3,4-thiadiazol-2-yl)-4-fluorobenzenesulfonamide

Example 252

N-{5-[(2-allylphenoxy)methyl]-1,3,4-thiadiazol-2-yl}-3-chloro-2-methylbenzenesulfonamide Prepared using method C.
$^1$H NMR (270 MHz, METHANOL-D4) δ ppm 2.69 (s, 3H) 3.38 (d, J=6.43 Hz, 2H) 4.93–5.06 (m, 2H) 5.22 (s, 2H) 5.85–6.03 (m, 1H) 6.97 (dd, J=14.35, 7.92 Hz, 2H) 7.12–7.24 (m, 2H) 7.30 (t, J=8.04 Hz, 1H) 7.60 (dd, J=8.04, 0.87 Hz, 1H) 7.93 (dd, J=7.92, 0.99 Hz, 1H). MS (M+1) 436

Example 253

4-bromo-N-[5-(4-chlorobenzyl)-1,3,4-thiadiazol-2-yl]benzenesulfonamide

Prepared using method A.
$^1$H NMR (270 MHz, DMSO-D) δ ppm 7.75 (d, J=8.66 Hz, 2H), 7.67 (d, J=8.66 Hz, 2H), 7.41 (d, J=8.41 Hz, 2H), 7.35 (d, J=8.41 Hz, 2H), 4.21 (s, 2H). MS (ESI+) m/z 444 (M+H)$^+$

Example 254

(R)-3-chloro-2-methyl-N-[5-(1-phenoxypropyl)-1,3,4-thiadiazol-2-yl]benzenesulfonamide Prepared using method C.
$^1$H NMR (270 MHz, METHANOL-D4) δ ppm 1.04 (t, J=7.42 Hz, 3H) 1.89–2.17 (m, 2H) 2.65 (s, 3H) 5.38 (t, J=6.43 Hz, 1H) 6.93–7.02 (m, 3H) 7.21–7.33 (m, 3H) 7.58 (d, J=7.92 Hz, 1H) 7.89 (d, J=7.92 Hz, 1H). MS (M+1) 424

Example 255

3-chloro-2-methyl-N-[5-({[2-(4-methylphenoxy)ethyl]thio}methyl)-1,3,4-thiadiazol-2-yl]benzenesulfonamide Prepared using method C.
$^1$H NMR (270 MHz, CHLOROFORM-D) δ ppm 2.21 (s, 3H) 2.62 (s, 3H) 2.83 (t, J=5.94 Hz, 2H) 3.84 (s, 2H) 4.08 (t, J=5.94 Hz, 2H) 6.63–6.72 (m, 2H) 6.99 (d, J=8.66 Hz, 2H) 7.09–7.18 (m, 1H) 7.47 (d, J=8.16 Hz, 1H) 7.91 (d, J=7.92 Hz, 1H). MS (M+1) 470

Example 256

4-chloro-N-(5-isobutyl-1,3,4-thiadiazol-2-yl)benzenesulfonamide

Example 257

4-chloro-N-[5-(ethylthio)-1,3,4-thiadiazol-2-yl]-3-nitrobenzenesulfonamide

Prepared using method C.
1H NMR 270 MHz, CHLOROFORM-D) δ ppm 1.43 (t, J=7.26 Hz, 3H) 3.18 (q, J=7.30 Hz, 2H) 7.66–7.69 (m, 1H) 8.01–8.04 (m, 1H) 8.36–8.37 (m, 1H). MS (ESI+) m/z 381, 383 (M+H)$^+$.

Example 258

(R)-3-chloro-2-methyl-N-[5-(1-phenylethyl)-1,3,4-thiadiazol-2-yl]benzenesulfonamide
Prepared using method C.
1H NMR (270 MHz, METHANOL-D4) δ ppm 1.65 (d, J=6.93 Hz, 3H) 2.66 (s, 3H) 4.30 (q, J=7.09 Hz, 1H) 7.22–7.40 (m, 6H) 7.57 (dd, J=8.16, 0.99 Hz, 1H) 7.85 (dd, J=7.92, 0.99 Hz, 1H). MS (M+1) 394

Example 259

3-chloro-N-[5-(ethylthio)-1,3,4-thiadiazol-2-yl]-2-methylbenzenesulfonamide

Prepared using method C.
1H NMR (270 MHz, CHLOROFORM-D) δ ppm 1.40 (t, J=7.39 Hz, 3H) 2.68 (s, 3H) 3.14 (q, J=7.21 Hz, 2H) 7.19–7.25 (m, 1H) 7.52–7.55 (m, 1H) 7.94–7.97 (m, 1H). MS (ESI+) m/z 350, 352 (M+H)+.

Example 260

N-(5-tert-butyl-1,3,4-thiadiazol-2-yl)naphthalene-2-sulfonamide

Prepared using method C.
1H NMR (270 MHz, METHANOL-D4) δ ppm 1.36 (s, 9H) 7.61 (m, 2H) 7.83 (dd, J=8.71, 1.85 Hz, 1H) 7.96 (m, 3H) 8.43 (d, J=1.85 Hz, 1H). MS (ESI+) m/z 348 (M+H)+. HRMS (ESI) calcd for $C_{16}H_{17}N_3O_2S_2$: 347.0762. Found 347.0753.

Example 261

N-(5-cyclohexyl-1,3,4-thiadiazol-2-yl)-2,4,6-trimethylbenzenesulfonamide

Comparison Example 262

N-[5-(2,2-dimethylpropyl)-1,3,4-thiadiazol-2-yl]benzenesulfonamide

Example 263

4-chloro-N-(5-cyclohexyl-1,3,4-thiadiazol-2-yl)benzenesulfonamide

Example 264

3-chloro-N-{5-[(2-fluorophenoxy)methyl]-1,3,4-thiadiazol-2-yl}-2-methylbenzenesulfonamide Prepared using method C.
$^1$H NMR (270 MHz, METHANOL-D4) δ ppm 2.69 (s, 3H) 5.27 (s, 2H) 6.95–7.22 (m, 4H) 7.31 (t, J=8.04 Hz, 1H) 7.61 (d, J=7.92 Hz, 1H) 7.95 (d, J=8.16 Hz, 1H). MS (M+1) 414

Example 265

(R)-3-chloro-2-methyl-N-[5-(1-phenylpropyl)-1,3,4-thiadiazol-2-yl]benzenesulfonamide Prepared using method C.
$^1$H NMR (270 MHz, METHANOL-D4) δ ppm 0.89 (t, J=7.30 Hz, 3H) 1.90–2.10 (m, 1H) 2.11–2.32 (m, 1H) 2.66 (s, 3H) 4.03 (dd, J=8.54, 6.80 Hz, 1H) 7.17–7.41 (m, 6H) 7.57 (dd, J=7.92, 1.24 Hz, 1H) 7.85 (dd, J=7.92, 1.24 Hz, 1H). MS (M+1) 408

Example 266

N-[5-(2,2-dimethylpropyl)-1,3,4-thiadiazol-2-yl]-4-nitrobenzenesulfonamide

Example 267

N-[5-(2,2-dimethylpropyl)-1,3,4-thiadiazol-2-yl]-4-fluorobenzenesulfonamide

Prepared using method A.
$^1$H NMR (270 MHz, DMOS-D) δppm 7.87–7.82 (m, 2H), 7.41–7.35 (m, 2H), 2.71 (s, 2H), 0.95 (s, 9H). MS (ESI+) m/z 330 (M+H)+

Example 268

N-(5-isopropyl-1,3,4-thiadiazol-2-yl)biphenyl-4-sulfonamide

Prepared using method A.
$^1$H NMR (270 MHz, Chloroform-D) δ ppm 7.98 (d, J=8.4 Hz, 2H), 7.65 (d, J=8.4 Hz, 2H), 7.57–7.54 (m, 2H), 7.47–7.35 (m, 3H), 3.18–3.08 (m, 1H), 1.34 (d, J=5.4 Hz, 6H). MS (ESI+) m/z 360 (M+H)+

Example 269

3-chloro-2-methyl-N-{5-[(phenylthio)methyl]-1,3,4-thiadiazol-2-yl}benzenesulfonamide Prepared using method C.
1H NMR (270 MHz, METHANOL-D4) δ ppm 2.64 (s, 3H) 4.26 (s, 2H) 7.30 (m, 6H) 7.61 (d, J=7.92 Hz, 1H) 7.90 (d, J=7.92 Hz, 1H). MS (ESI+) m/z 412 (M+H)+.

Example 270

3-chloro-N-(5-{[(4-fluorobenzyl)thio]methyl}-1,3,4-thiadiazol-2-yl)-2-methylbenzenesulfonamide Prepared using method C.
$^1$H NMR (270 MHz, CHLOROFORM-D) δ ppm 2.64 (s, 3H) 3.57 (s, 2H) 3.61 (s, 2H) 6.91 (t, J=8.54 Hz, 2H) 7.12–7.22 (m, 3H) 7.49 (d, J=7.92 Hz, 1H) 7.93 (d, J=7.92 Hz, 1H). MS (M+1) 444

Example 271

N-{5-[(benzylthio)methyl]-1,3,4-thiadiazol-2-yl}-3-chloro-2-methylbenzenesulfonamide Prepared using method C.
1H NMR (270 MHz, CHLOROFORM-D) δ ppm 2.65 (s, 3H) 3.57 (s, 2H) 3.64 (s, 2H) 7.19 (m, 6H) 7.49 (d, J=7.92 Hz, 1H) 7.93 (d, J=7.92 Hz, 1H). MS (M+1) 426

Example 272

4-bromo-N-[5-(2,2-dimethylpropyl)-1,3,4-thiadiazol-2-yl]benzenesulfonamide

Prepared using method A.
$^1$H NMR (270 MHz, DMSO-D) δ ppm 7.76 (d, J=8.66 Hz, 2H), 7.70 (d, J=8.66 Hz, 2H), 2.71 (s, 2H), 0.95 (s, 9H). MS (ESI+) m/z 390 (M+H)$^+$

Example 273

N-(4-{[(5-methyl-1,3,4-thiadiazol-2-yl)amino]sulfonyl} phenyl)benzamide

Prepared using method C.
1H NMR (270 MHz, METHANOL-D4) δ ppm 2.42 (s, 3H) 7.47 (m, 3H) 7.80 (m, 4H) 7.88 (m, 2H). MS (ESI+) m/z 375 (M+H)$^+$.

Example 274

N-1,3-benzodioxol-5-yl-2-[(5-{[(4-methylphenyl)sulfonyl]amino}-1,3,4-thiadiazol-2-yl)thio]acetamide

Comparison Example 275

4-amino-N-(5-ethyl-1,3,4-thiadiazol-2-yl)benzenesulfonamide

Comparison Example 276

N-(5-ethyl-1,3,4-thiadiazol-2-yl)-4-({[(4-fluorophenyl)amino]carbonothioyl}amino)benzenesulfonamide

Example 277

N-(5-ethyl-1,3,4-thiadiazol-2-yl)-4-(1H-tetrazol-1-yl)benzenesulfonamide

Prepared using method C.
$^1$H NMR (270 MHz, DMSO-D6) δ ppm 1.21 (t, J=7.42 Hz, 3H) 2.83 (q, J=7.42 Hz, 2H) 8.02–8.12 (m, 4H) 10.18 (s, 1H). MS (ESI+) m/z 338 (M+H)$^+$.

Comparison Example 278

N-[5-(trifluoromethyl)-1,3,4-thiadiazol-2-yl]benzenesulfonamide

Comparison Example 279

N-(4-{[(5-isopropyl-1,3,4-thiadiazol-2-yl)amino]sulfonyl}phenyl)acetamide

Prepared using method C.
$^1$H NMR (270 MHz, DMSO-D6) δ ppm 1.23–1.26 (m, 6H) 2.06 (s, 3H) 3.07–3.16 (m, 1H) 7.68–7.71 (m, 4H) 10.28 (s, 1H). MS (ESI+) m/z 341 (M+H)$^+$.

Example 280

N-(5-ethyl-1,3,4-thiadiazol-2-yl)-4-[(4-methylphthalazin-1-yl)amino]benzenesulfonamide

Example 281

N-(5-isopropyl-1,3,4-thiadiazol-2-yl)-4-methylbenzenesulfonamide

Example 282

N-[5-(methoxymethyl)-1,3,4-thiadiazol-2-yl]-4-nitrobenzenesulfonamide

Prepared using method A.
$^1$H NMR (270 MHz, DMSO-D) δ ppm 8.35 (d, J=8.65 Hz, 2H), 8.04 (d, J=8.65 Hz, 2H), 4.58 (s, 2H), 3.34 (s, 3H). MS (ESI+) m/z 331 (M+H)$^+$

Comparison Example 283

4-amino-N-(5-methyl-1,3,4-thiadiazol-2-yl)benzenesulfonamide

Comparison Example 284

N-[5-(ethylthio)-1,3,4-thiadiazol-2-yl]-4-methoxybenzenesulfonamide

Example 285

4-fluoro-N-(5-isopropyl-1,3,4-thiadiazol-2-yl)benzenesulfonamide

Prepared using method A.
$^1$H NMR (270 MHz, DMSO-D) δ ppm 787–7.82 (m, 2H), 7.41–7.34 (m, 2H), 3.19–3.09 (m, 1H), 1.25 (d, J=6.93 Hz, 6H). MS (ESI+) m/z 302 (M+H)$^+$

Example 286

3-cyano-N-(5-isopropyl-1,3,4-thiadiazol-2-yl)benzenesulfonamide

Prepared using method A.
$^1$H NMR (270 MHz, Chloroform-D) δ ppm 8.18 (d, J=5.4 Hz, 1H), 7.81–7.58 (m, 3H), 3.18–3.08 (m, 1H), 1.34 (d, J=5.4 Hz, 6H). MS (ESI+) m/z 309 (M+H)$^+$

Example 287

3-cyano-N-(5-phenyl-1,3,4-thiadiazol-2-yl)benzenesulfonamide

Prepared using method C.
$^1$H NMR (270 MHz, METHANOL-D4) δ ppm 7.38–7.47 (m, 3H) 7.61–7.69 (m, 1H) 7.70–7.79 (m, 3H) 7.85 (dd, J=7.55, 1.36 Hz, 1H) 8.09 (dd, J=7.79, 1.11 Hz, 1H). MS (ESI+) m/z 343 (M+H)$^+$

Example 288

5-bromo-N-(5-isopropyl-1,3,4-thiadiazol-2-yl)-2-methoxybenzenesulfonamide

Prepared using method A.
$^1$H NMR (270 MHz, Chloroform-D) δ ppm 8.13–8.11 (m, 1H), 7.57–7.52 (m, 1H), 6.84–6.80 (m, 1H), 3.72 (s, 3H), 3.21–3.10 (m, 1H), 1.35 (d, J=5.4 Hz, 6H). MS (ESI+) m/z 392 (M+H)$^+$ Wound Healing Experiments Example 289

Diabetic KKA$^y$ mice underwent surgery during anesthesia whereby a catheter was inserted in the jugularis vein. Oral treatment twice daily (200 mg/kg/day) with the 11β-HSD1 inhibitor BVT.2733 (disclosed as Example 172A in WO 01/90090), or vehicle started 4–6 days later and continued for 3.5 days.

Advantageous effects on wound healing of the surgical wounds were observed during treatment. In BVT.2733 treated mice, less complication were observed in and around the wound area as compared to control mice. Examples of advantageous effects were less pus in the wound, as well as better wound strength. 58% of the vehicle treated animals showed complications during treatment period whereas complications were present in only 24% of the BVT.2733 treated animals.

Example 290

(a) Advantageous effects of 11β-HSD1 inhibitors (e.g. BVT.2733) on wound healing are confirmed in diabetic KKA$^y$ mice employing the excisional wound-healing model. 1 cm full-thickness wounds, including the panniculus carnosus muscle, are cut with a scalpel on the back of the mice. Mice are treated with BVT.2733 for 5 days. On day 2 and 9 of treatment wounds are harvested, embedded and sectioned. Histological staining of the sections with hematoxylin/eosin are made to determine degree of re-epithelialization and immunostaining against the von Willebrand factor to determine revascularisation.

(b) Advantageous effects of 11β-HSD1 inhibitors are confirmed in in vitro studies. Proliferation of human keratinocytes and fibroblasts, which are important cell types in the wound healing process, are studied after incubation with the 11β-HSD1 inhibitor.

(c) Effects on wound healing after treatment with 11β-HSD1 inhibitors are also studied in wounds on explants from human breast skin. The proliferative effect of the substance and the effect on re-epithelialization are determined.

Various embodiments of the present invention have been described above but a person skilled in the art realizes further minor alterations which would fall into the scope of the present invention. The breadth and scope of the present invention should not be limited by any of the above-described exemplary embodiments, but should be defined only in accordance with the following claims and their equivalents.

What is claimed is:

1. A method for promoting wound healing or for the treatment of a disease or disorder, selected from type-2 diabetes, obesity, glaucoma, hyperlipidemia, hyperglycemia, hypertension, osteoporosis, and depression, said method comprising administering to a mammal, including a human, in need of such treatment an effective amount of a compound of formula (I)

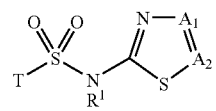

I wherein
T is selected from:
2-acetylamino-4-methylthiazol-5-yl; benzyl; 5-bromo-6-chloropyridin-3-yl; 5-chloro-1,3-dimethyl-1H-pyrazol-4-yl; 2,3-dihydro-1,4-benzodioxin-6-yl; 2,3-dihydro-1-benzofuran-5-yl; 5-(dimethylamino)-1-naphthyl; 1,2-dimethyl-1H-imidazol-4-yl; 3,5-dimethylisoxazol-4-yl; 4-methyl-3,4-dihydro-2H-1,4-benzoxazin-7-yl; 1-methyl-1H-imidazol-4-yl; 5-methyl-2-(trifluoromethyl)-3-furyl; 4-morpholin-4-ylpyridin-3-yl; 1-naphthyl; 2-naphthyl; 2,2,4,6,7-pentamethyl-2,3-dihydro-1-benzofuran-5-yl; 6-phenoxypyridin-3-yl; quinolin-8-yl; 1,3,5-trimethyl-1H-pyrazol-4-yl;
thienyl optionally substituted with one or more of acetylamino; chloro; methyl; 2-(methylthio)pyrimidin-4-yl; nitro; phenylsulfonyl; pyridinyl;
phenyl optionally substituted with one or more of acetyl; acetylamino; amino; 4-(1,3-benzothiazol-2-ylthio) acetylamino; benzoylamino; bromo; chloro; 3-chloro-2-cyanophenoxy; (5-chloro-2-hydroxybenzyl)amino; 4-chloro-3-nitrophenylcarbonylamino; [(4-chlorophenyl)amino]carbonylamino; cyano; 2,4-dichlorophenoxyacetylamino; fluoro; 4-{[(4-fluorophenyl)amino]carbonothioyl}amino; 4-fluorophenylcarbonylamino; hydroxy; methoxy; methyl; 5-methyl-1,3,4-oxadiazol-2-yl; (4-methylphthalazin-1-yl)amino; 1,3-oxazol-5-yl; 2-methyl-4-pyrimidyl; n-butoxy; nitro; N-phthalimido; phenoxy; phenyl; 1H-pyrazol-1-yl; tert-butyl; tetrazolyl; 2,2,2-trifluoroethoxy; trifluoromethoxy; trifluoromethyl;
$R^1$ is hydrogen or methyl;
$A_1$ and $A_2$ are a nitrogen atom or C—Z, provided that $A_1$ and $A_2$ have different meanings, wherein:
Z is [(1,3-benzodioxol-5-ylaminocarbonyl)methyl]thio; n-butylthio; (R)-2-[(3-chloro-2-methylbenzenesulfonyl)oxy]propyl; cyclohexyl; cyclopropyl; ethoxycarbonylmethylthio; ethylthio; (R)-2-[(3-fluorophenyl)thio] propyl; 3-furyl; methoxy; 2-methylpyridin-3-yl; morpholin-4-yl; (R)-1-phenoxy-n-propyl; phenyl; (R)-1-phenyl-n-propyl; tert-butyl; tert-butylphenyl; 2-thienyl; 3-thienyl; (trichloromethyl); (trifluoromethyl); $A_3$; or is —CH(CH$_3$)A$_3$, wherein
$A_3$ is selected from methyl; carbamoyl; N—(n-butanamidyl); phenylsulfonyl; phenyl; phenoxy optionally substituted with one or more fluoro; phenylthio optionally substituted with one or more acetylamino, methoxy, trifluoromethyl, fluoro; pyridin-3-yloxy; 4-methylpyrimidin-2-ylthio; pyridin-4-ylthio; 1-methyl-1H-imidazol-2-ylthio; or X—Y—R$^2$, wherein
X is CH$_2$ or CO;
Y is CH$_2$, CO or a single bond;
$R^2$ is selected from:
4-acetylaminophenylsulfonyl; 1-(3-chloro-2-methylphenylsulfonyloxyl)ethyl; 1-[(3-fluorophenyl)thio]ethyl; 4-chlorophenyl; 3-ethoxy-n-propyl; hydrogen; isopropyl; 4-methoxyphenyl; methyl; phenylsulfonyl; pyridin-3-yl; tert-butyl;
NR$^3$R$^4$, wherein R$^3$ and R$^4$ are each independently selected from 3-ethoxy-n-propyl; ethyl; hydrogen; methyl;
NR$^3$R$^4$ represent together 3-carbethoxypiperidin-1-yl; 4-carbethoxypiperidin-1-yl; 3-hydroxymethylpiperidin-1-yl; 3-hydroxypiperidin-1-yl; 4-methylpiperazin-1-yl; morpholin-4-yl; 3-oxopiperazin-1-yl;
R$^5$O, wherein R$^5$ is 2-allylphenyl; 4-chlorophenyl; ethyl; 2-fluorophenyl; 4-fluorophenyl; hydrogen; methyl; 4-nitrophenyl;

$R^6S$, wherein $R^6$ is 2-acetylaminophenyl; 3-acetylaminophenyl; 4-acetylaminophenyl; benzyl; 2,4-difluorophenyl; 3,4-difluorophenyl; 3,4-dimethoxyphenyl; 4-fluorobenzyl; 3-fluorophenyl; 2-methoxyphenyl; 3-methoxyphenyl; 1-methyl-1H-imidazol-2-yl; 2-(4-methylphenoxy)ethyl; 4-methylpyrimidin-2-yl; phenyl; pyridin-2-yl; pyridin-4-yl; pharmaceutically acceptable salts, solvates, hydrates, geometrical isomers, tautomers, optical isomers, N-oxides and prodrug forms thereof;

with the proviso that T is not selected from 4-acetylaminophenyl, 4-aminophenyl, 4-(4-chloro-3-nitrophenylcarbonylamino)phenyl, 4-{[(4-chlorophenyl)amino]carbonylamino}-phenyl, 4-(2,4-dichlorophenoxyacetylamino)phenyl, 4-({[(4-fluorophenyl)amino]-carbonothioyl}amino)phenyl, 4-methoxyphenyl, phenyl, 4-(N-phthalimido)phenyl, and 3-(trifluoromethyl)phenyl;

and with the proviso that when $R^1$ is hydrogen and $A_1$ is C—Z and $A_2$ is a nitrogen atom, Z is phenyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is hydrogen, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is methyl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is methyl and $R^4$ is is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is $CH_2$, Y is CO, $R^2$ is $R^5O$, $R^5$ is hydrogen, then T is not 3-chloro-2-methylphenyl;

$A_1$ is C—Z and $A_2$ is a nitrogen atom, X is $CH_2$, Y is CO, $R^2$ is $R^5O$, $R^5$ is methyl, then T is not 3-chloro-2-methylphenyl;

$A_1$ is C—Z and $A_2$ is a nitrogen atom, X is $CH_2$, Y is CO, $R^2$ is $R^5O$, $R^5$ is ethyl, then T is not 3-chloro-2-methylphenyl;

$A_1$ is C—Z and $A_2$ is a nitrogen atom, X is $CH_2$, Y is a single bond, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is CO, Y is CO, $R^2$ is $R^5O$, $R^5$ is ethyl, then T is not 3-chloro-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-phenoxyphenyl;

$A_1$ is C—Z and $A_2$ is a nitrogen atom, Z is phenyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ is ethyl and $R^4$ methyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ are both ethyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 1,1'-biphenyl-4-yl;

$A_1$ is a nitrogen atom and $A_2$ is C—Z, Z is phenyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ are both ethyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 4-bromo-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-bromo-2-methylphenyl;

$A_1$ is C—Z and $A_2$ is a nitrogen atom, Z is phenyl, then T is not 2,4-dichloro-6-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ is ethyl and $R^4$ methyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, Z is phenyl, then T is not 2,4-dichloro-6-methylphenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is C—Z and $A_2$ is a nitrogen atom, Z is phenyl, then T is not 2,4,6-trichlorophenyl;

A₁ is C—Z and A₂ is a nitrogen atom, X is CH₂, Y is CO, R² is NR³R⁴, R³ is ethyl and R⁴ is methyl, then T is not 2,4,6-trichlorophenyl;

A₁ is C—Z and A₂ is a nitrogen atom, X is CH₂, Y is CO, R² is NR³R⁴, R³ and R⁴ are both ethyl, then T is not 2,4,6-trichlorophenyl;

A₁ is C—Z and A₂ is a nitrogen atom, X is CH₂, Y is CH₂, R² is NR³R⁴, R³ and R⁴ represent together morpholin-4-yl, then T is not 2,4,6-trichlorophenyl;

A₁ is C—Z and A₂ is a nitrogen atom, X is CH₂, Y is CO, R² is NR³R⁴, R³ and R⁴ represent together morpholin-4-yl, then T is not 2,4,6-trichlorophenyl;

A₁ is a nitrogen atom and A₂ is C—Z, Z is phenyl, then T is not 2,4,6-trichlorophenyl;

A₁ is a nitrogen atom and A₂ is C—Z, X is CH₂, Y is CO, R² is NR³, R³ is ethyl and R⁴ is methyl, then T is not 2,4,6-trichlorophenyl;

A₁ is a nitrogen atom and A₂ is C—Z, X is CH₂, Y is CO, R² is NR³R⁴, R³ and R⁴ are ethyl, then T is not 2,4,6-trichlorophenyl;

A₁ is a nitrogen atom and A₂ is C—Z, X is CH₂, Y is CH₂, R² is NR³R⁴, R³ and R⁴ represent together morpholin-4-yl, then T is not 2,4,6-trichlorophenyl;

A₁ is a nitrogen atom and A₂ is C—Z, X is CH₂, Y is CO, R² is NR³R⁴, R³ and R⁴ represent together morpholin-4-yl, then T is not 2,4,6-trichlorophenyl.

2. The method according to claim 1, for promoting wound healing.

3. The method according to claim 1, wherein the method is for the treatment of a disease or disorder selected from type-2 diabetes, obesity, glaucoma, hyperlipidemia, hyperglycemia, hypertension, osteoporosis, and depression.

4. The method according to claim 1 for the treatment or prophylaxis of a medical condition involving delayed or impaired wound healing.

5. The method according to claim 4, wherein the medical condition involving delayed or impaired wound healing is diabetes.

6. The method according to claim 4, wherein the medical condition involving delayed or impaired wound healing is caused by treatment with glucocorticoids.

7. The method according to claim 1 for the promotion of wound healing in chronic wounds, such as diabetic ulcers, venous ulcers or pressure ulcers.

8. The method according to any one of claims 1 to 7, wherein T is selected from the group consisting of 2-acetylamino-4-methylthiazol-5-yl, 4-acetylphenyl, 4-benzoylaminophenyl, benzyl, 2,5-bis(2,2,2-trifluoroethoxy)phenyl, 3,5-bis(trifluoromethyl)phenyl, 5-bromo-6-chloropyridin-3-yl, 5-bromo-2-methoxyphenyl, 4-(3-chloro-2-cyanophenoxy)phenyl, 5-chloro-1,3-dimethyl-1H-pyrazol-4-yl, 3-chloro-5-fluoro-2-methylphenyl, 3-chloro-4-fluorophenyl, 3-chloro-4-methylphenyl, 4-chloro-3-nitrophenyl, 5-chloro-4-nitro-2-thienyl, 5-chlorothien-2-yl, 2-cyanophenyl, 3-cyanophenyl, 4-cyanophenyl, 3,5-dichloro-2-hydroxyphenyl, 2,6-dichlorophenyl, 4,5-dichloro-2-thienyl, 2,4-difluorophenyl, 2,6-difluorophenyl, 2,3-dihydro-1,4-benzodioxin-6-yl, 2,3-dihydro-1-benzofuran-5-yl, 3,4-dimethoxyphenyl, 5-(dimethylamino)-1-naphthyl, 1,2-dimethyl-1H-imidazol-4-yl, 3,5-dimethylisoxazol-4-yl, 5-fluoro-2-methylphenyl, 3-fluorophenyl, 4-(4-fluorophenylcarbonylamino)phenyl, 4-methoxy-2,3,6-trimethylphenyl, 4-methyl-3,4-dihydro-2H-1,4-benzoxazin-7-yl, 1-methyl-1H-imidazol-4-yl, 2-methyl-5-nitrophenyl, 3-(5-methyl-1,3,4-oxadiazol-2-yl)phenyl, 3-(2-methylpyrimidin-4-yl)phenyl, 5-[2-(methylthio)pyrimidin-4-yl]-2-thienyl, 5-methyl-2-(trifluoromethyl)-3-furyl, 4-morpholin-4-ylpyridin-3-yl, 1-naphthyl, 2-nitrophenyl, 3-nitrophenyl, 4-(1,3-oxazol-5-yl)phenyl, 2,2,4,6,7-pentamethyl-2,3-dihydro-1-benzofuran-5-yl, 6-phenoxypyridin-3-yl, 4-(phenylsulfonyl)-2-thienyl, 4-(1H-pyrazol-1-yl)phenyl, 5-pyridin-2-yl-2-thienyl, quinolin-8-yl, 4-tert-butylphenyl, 4-(1H-tetrazol-1-yl)phenyl, 2-thienyl, 3-(trifluoromethoxy)phenyl, 2-(trifluoromethyl)phenyl, and 1,3,5-trimethyl-1H-pyrazol-4-yl.

9. The method according to any one of claims 1 to 7, wherein the compound is selected from the group consisting of:

N-(3-isopropyl-1,2,4-thiadiazol-5-yl)quinoline-8-sulfonamide;

3-cyano-N-(3-ethyl-1,2,4-thiadiazol-5-yl)benzenesulfonamide;

N-(3-isopropyl-1,2,4-thiadiazol-5-yl)-3-(2-methylpyrimidin-4-yl)benzenesulfonamide;

N-(3-isopropyl-1,2,4-thiadiazol-5-yl)-1,3,5-trimethyl-1H-pyrazole-4-sulfonamide;

N-(3-isopropyl-1,2,4-thiadiazol-5-yl)-3,5-dimethylisoxazole-4-sulfonamide;

N-(3-tert-butyl-1,2,4-thiadiazol-5-yl)-3-cyanobenzenesulfonamide;

N-(3-ethyl-1,2,4-thiadiazol-5-yl)-5-fluoro-2-methylbenzenesulfonamide;

N-(3-isopropyl-1,2,4-thiadiazol-5-yl)-1-methyl-1H-imidazole-4-sulfonamide;

N-(3-isopropyl-1,2,4-thiadiazol-5-yl)-1-phenylmethanesulfonamide;

3-chloro-4-methyl-N-(3-phenyl-1,2,4-thiadiazol-5-yl)benzenesulfonamide;

N-(5-{[(3-isopropyl-1,2,4-thiadiazol-5-yl)amino]sulfonyl}-4-methyl-1,3-thiazol-2-yl)acetamide;

N-(3-isopropyl-1,2,4-thiadiazol-5-yl)-3-(5-methyl-1,3,4-oxadiazol-2-yl)benzenesulfonamide;

3-cyano-N-(3-isopropyl-1,2,4-thiadiazol-5-yl)benzenesulfonamide;

2-cyano-N-(3-isopropyl-1,2,4-thiadiazol-5-yl)benzenesulfonamide;

5-bromo-N-(3-isopropyl-1,2,4-thiadiazol-5-yl)-2-methoxybenzenesulfonamide;

N-(3-isopropyl-1,2,4-thiadiazol-5-yl)-6-morpholin-4-ylpyridine-3-sulfonamide;

N-(3-isopropyl-1,2,4-thiadiazol-5-yl)-3-(trifluoromethoxy)benzenesulfonamide;

N-(3-isopropyl-1,2,4-thiadiazol-5-yl)thiophene-2-sulfonamide;

5-chloro-N-(3-isopropyl-1,2,4-thiadiazol-5-yl)-1,3-dimethyl-1H-pyrazole-4-sulfonamide;

N-(3-isopropyl-1,2,4-thiadiazol-5-yl)-4-methyl-3,4-dihydro-2H-1,4-benzoxazine-7-sulfonamide;

5-chloro-N-(3-phenyl-1,2,4-thiadiazol-5-yl)thiophene-2-sulfonamide;

4-chloro-3-nitro-N-[3-(2-thienyl)-1,2,4-thiadiazol-5-yl]benzenesulfonamide;

4-cyano-N-(3-isopropyl-1,2,4-thiadiazol-5-yl)benzenesulfonamide;

N-(3-isopropyl-1,2,4-thiadiazol-5-yl)-2,3-dihydro-1-benzofuran-5-sulfonamide;

N-(3-isopropyl-1,2,4-thiadiazol-5-yl)-3,4-dimethoxybenzenesulfonamide;

N-(3-isopropyl-1,2,4-thiadiazol-5-yl)-2,3-dihydro-1,4-benzodioxine-6-sulfonamide;

N-(3-isopropyl-1,2,4-thiadiazol-5-yl)-6-phenoxypyridine-3-sulfonamide;

3-fluoro-N-(3-isopropyl-1,2,4-thiadiazol-5-yl)benzenesulfonamide;

N-(3-isopropyl-1,2,4-thiadiazol-5-yl)-3-nitrobenzenesulfonamide;
N-(3-isopropyl-1,2,4-thiadiazol-5-yl)-2-nitrobenzenesulfonamide;
N-(3-isopropyl-1,2,4-thiadiazol-5-yl)-3,5-bis(trifluoromethyl)benzenesulfonamide;
5-(dimethylamino)-N-(3-isopropyl-1,2,4-thiadiazol-5-yl)naphthalene-1-sulfonamide;
4-acetyl-N-(3-isopropyl-1,2,4-thiadiazol-5-yl)benzenesulfonamide;
N-(3-isopropyl-1,2,4-thiadiazol-5-yl)naphthalene-1-sulfonamide;
2,6-difluoro-N-(3-isopropyl-1,2,4-thiadiazol-5-yl)benzenesulfonamide;
N-(3-isopropyl-1,2,4-thiadiazol-5-yl)-2-(trifluoromethyl)benzenesulfonamide;
3,5-dichloro-2-hydroxy-N-(3-isopropyl-1,2,4-thiadiazol-5-yl)benzenesulfonamide;
5-fluoro-N-(3-isopropyl-1,2,4-thiadiazol-5-yl)-2-methylbenzenesulfonamide;
N-(3-isopropyl-1,2,4-thiadiazol-5-yl)-2-methyl-5-nitrobenzenesulfonamide;
2,4-difluoro-N-(3-isopropyl-1,2,4-thiadiazol-5-yl)benzenesulfonamide;
N-(3-isopropyl-1,2,4-thiadiazol-5-yl)-5-methyl-2-(trifluoromethyl)furan-3-sulfonamide;
N-(3-isopropyl-1,2,4-thiadiazol-5-yl)-4-(phenylsulfonyl)thiophene-2-sulfonamide;
3-chloro-4-fluoro-N-(3-isopropyl-1,2,4-thiadiazol-5-yl)benzenesulfonamide;
N-(3-ethyl-1,2,4-thiadiazol-5-yl)-5-[2-(methylthio)pyrimidin-4-yl]thiophene-2-sulfonamide;
5-bromo-6-chloro-N-(3-isopropyl-1,2,4-thiadiazol-5-yl)pyridine-3-sulfonamide;
3-chloro-N-(3-isopropyl-1,2,4-thiadiazol-5-yl)-4-methylbenzenesulfonamide;
N-(3-isopropyl-1,2,4-thiadiazol-5-yl)-4-(1H-pyrazol-1-yl)benzenesulfonamide;
N-(3-isopropyl-1,2,4-thiadiazol-5-yl)-2,2,4,6,7-pentamethyl-2,3-dihydro-1-benzofuran-5-sulfonamide;
N-(3-isopropyl-1,2,4-thiadiazol-5-yl)-4-methoxy-2,3,6-trimethylbenzenesulfonamide;
N-(3-isopropyl-1,2,4-thiadiazol-5-yl)-5-pyridin-2-ylthiophene-2-sulfonamide;
N-(3-isopropyl-1,2,4-thiadiazol-5-yl)-4-(1,3-oxazol-5-yl)benzenesulfonamide;
2,6-dichloro-N-(3-isopropyl-1,2,4-thiadiazol-5-yl)benzenesulfonamide;
4-(3-chloro-2-cyanophenoxy)-N-(3-isopropyl-1,2,4-thiadiazol-5-yl)benzenesulfonamide;
5-chloro-N-(3-isopropyl-1,2,4-thiadiazol-5-yl)-4-nitrothiophene-2-sulfonamide;
3-chloro-5-fluoro-N-(3-isopropyl-1,2,4-thiadiazol-5-yl)-2-methylbenzenesulfonamide;
4,5-dichloro-N-(3-isopropyl-1,2,4-thiadiazol-5-yl)thiophene-2-sulfonamide;
5-fluoro-2-methyl-N-[3-(2-thienyl)-1,2,4-thiadiazol-5-yl]benzenesulfonamide;
4-tert-butyl-N-(3-phenyl-1,2,4-thiadiazol-5-yl)benzenesulfonamide;
4-chloro-N-(3-morpholin-4-yl-1,2,4-thiadiazol-5-yl)-3-nitrobenzenesulfonamide
3-chloro-4-fluoro-N-(3-phenyl-1,2,4-thiadiazol-5-yl)benzenesulfonamide
N-(3-isopropyl-1,2,4-thiadiazol-5-yl)-2,5-bis(2,2,2-trifluoroethoxy)benzenesulfonamide
N-(3-isopropyl-1,2,4-thiadiazol-5-yl)-1,2-dimethyl-1H-imidazole-4-sulfonamide
N-(3-phenyl-1,2,4-thiadiazol-5-yl)naphthalene-1-sulfonamide
N-(3-phenyl-1,2,4-thiadiazol-5-yl)thiophene-2-sulfonamide
2-nitro-N-(3-phenyl-1,2,4-thiadiazol-5-yl)benzenesulfonamide
5-fluoro-2-methyl-N-(3-morpholin-4-yl-1,2,4-thiadiazol-5-yl)benzenesulfonamide
4-tert-butyl-N-(3-methyl-1,2,4-thiadiazol-5-yl)benzenesulfonamide
4-cyano-N-(3-methyl-1,2,4-thiadiazol-5-yl)benzenesulfonamide
N-(4-{[(5-ethyl-1,3,4-thiadiazol-2-yl)amino]sulfonyl}phenyl)-4-fluorobenzamide;
5-fluoro-N-(5-isopropyl-1,3,4-thiadiazol-2-yl)-2-methylbenzenesulfonamide;
4-chloro-N-[5-(ethylthio)-1,3,4-thiadiazol-2-yl]-3-nitrobenzenesulfonamide;
N-(4-{[(5-methyl-1,3,4-thiadiazol-2-yl)amino]sulfonyl}phenyl)benzamide;
N-(5-ethyl-1,3,4-thiadiazol-2-yl)-4-(1H-tetrazol-1-yl)benzenesulfonamide;
3-cyano-N-(5-isopropyl-1,3,4-thiadiazol-2-yl)benzenesulfonamide;
3-cyano-N-(5-phenyl-1,3,4-thiadiazol-2-yl)benzenesulfonamide; and
5-bromo-N-(5-isopropyl-1,3,4-thiadiazol-2-yl)-2-methoxybenzenesulfonamide.

10. The method according to any one of claims 1 to 7, wherein T is 3-chloro-2-methylphenyl;

with the proviso that when $R^1$ is hydrogen and $A_1$ is C—Z and $A_2$ is a nitrogen atom, Z is phenyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ are both ethyl, then T is not 3-chloro-2-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is hydrogen, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is methyl, then T is not 3-chloro-2-methylphenyl;

$A_1$ is C—Z and $A_2$ is a nitrogen atom, X is $CH_2$, Y is $CH_2$, $R^2$ is $R^5O$, $R^5$ is ethyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is methyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ and $R^4$ are both methyl, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is hydrogen, then T is not 3-chloro-2-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 3-chloro-2-methylphenyl;

A₁ is C—Z and A₂ is a nitrogen atom, X is CH₂, Y is CO, R² is NR³R⁴, R³ and R⁴ are both ethyl, then T is not 3-chloro-2-methylphenyl;

A₁ is C—Z and A₂ is a nitrogen atom, X is CH₂, Y is CO, R² is NR³R⁴, R³ and R⁴ represent together morpholin-4-yl, then T is not 3-chloro-2-methylphenyl;

A₁ is C—Z and A₂ is a nitrogen atom, X is CH₂, Y is CO, R² is R⁵O, R⁵ is hydrogen, then T is not 3-chloro-2-methylphenyl;

A₁ is C—Z and A₂ is a nitrogen atom, X is CH₂, Y is CO, R² is R⁵O, R⁵ is methyl, then T is not 3-chloro-2-methylphenyl;

A₁ is C—Z and A₂ is a nitrogen atom, X is CH₂, Y is CO, R² is R⁵O, R⁵ is ethyl, then T is not 3-chloro-2-methylphenyl;

A₁ is C—Z and A₂ is a nitrogen atom, X is CH₂, Y is a single bond, R² is NR³R⁴, R³ and R⁴ represent together morpholin-4-yl, then T is not 3-chloro-2-methylphenyl;

A₁ is C—Z and A₂ is a nitrogen atom, X is CO, Y is CO, R² is R⁵O, R⁵ is ethyl, then T is not 3-chloro-2-methylphenyl.

11. The method according to any one of claims 1 to 7 wherein the compound is selected from the group consisting of Ethyl 1-[(5-{[(3-chloro-2-methylphenyl)sulfonyl]amino}-1,2,4-thiadiazol-3-yl)carbonyl]piperidine-4-carboxylate;

5-{[(3-chloro-2-methylphenyl)sulfonyl]amino}-N-methyl-1,2,4-thiadiazole-3-carboxamide;

5-{[(3-chloro-2-methylphenyl)sulfonyl]amino}-1,2,4-thiadiazole-3-carboxamide;

5-{[(3-chloro-2-methylphenyl)sulfonyl]amino}-1,2,4-thiadiazole-3-carboxylic acid;

3-chloro-2-methyl-N-{3-[(4-methylpiperazin-1-yl)carbonyl]-1,2,4-thiadiazol-5-yl}benzenesulfonamide;

3-chloro-N-[3-(3-furyl)-1,2,4-thiadiazol-5-yl]-2-methylbenzenesulfonamide;

3-chloro-N-(3-{[3-(hydroxymethyl)piperidin-1-yl]carbonyl}-1,2,4-thiadiazol-5-yl)-2-methylbenzenesulfonamide;

3-chloro-2-methyl-N-(3-methyl-1,2,4-thiadiazol-5-yl)benzenesulfonamide;

(R)-2-(5-{[(3-chloro-2-methylphenyl)sulfonyl]amino}-1,2,4-thiadiazol-3-yl)propanamide;

N-(4-{[(5-{[(3-chloro-2-methylphenyl)sulfonyl]amino}1,2,4-thiadiazol-3-yl)methyl]thio}phenyl)acetamide;

3-chloro-2-methyl-N-(3-morpholin-4-yl-1,2,4-thiadiazol-5-yl)benzenesulfonamide;

(R)-N-(4-{[1-(5-{[(3-chloro-2-methylphenyl)sulfonyl]amino}-1,2,4-thiadiazol-3-yl)ethyl]thio}phenyl)acetamide;

5-{[(3-chloro-2-methylphenyl)sulfonyl]amino}-N-(3-ethoxypropyl)-1,2,4-thiadiazole-3-carboxamide;

3-chloro-2-methyl-N-{3-[(phenylsulfonyl)methyl]-1,2,4-thiadiazol-5-yl}benzenesulfonamide;

3-chloro-2-methyl-N-[3-(3-thienyl)-1,2,4-thiadiazol-5-yl]benzenesulfonamide;

(R)-N-[2-(5-{[(3-chloro-2-methylphenyl)sulfonyl]amino}-1,2,4-thiadiazol-3-yl)propyl]butanamide;

3-chloro-2-methyl-N-[3-(morpholin-4-ylcarbonyl)-1,2,4-thiadiazol-5-yl]benzenesulfonamide;

Ethyl 1-[(5-{[(3-chloro-2-methylphenyl)sulfonyl]amino}-1,2,4-thiadiazol-3-yl)carbonyl]piperidine-3-carboxylate;

3-chloro-N-{3-[(3-hydroxypiperidin-1-yl)carbonyl]-1,2,4-thiadiazol-5-yl}-2-methylbenzenesulfonamide;

3-chloro-2-methyl-N-[3-(trichloromethyl)-1,2,4-thiadiazol-5-yl]benzenesulfonamide;

3-chloro-2-methyl-N-[3-(2-thienyl)-1,2,4-thiadiazol-5-yl]benzenesulfonamide;

3-chloro-N-(3-methoxy-1,2,4-thiadiazol-5-yl)-2-methylbenzenesulfonamide;

(R)-3-chloro-N-(3-{1-[(3,4-dimethoxyphenyl)thio]ethyl}-1,2,4-thiadiazol-5-yl)-2-methylbenzenesulfonamide;

3-chloro-N-(3-ethyl-1,2,4-thiadiazol-5-yl)-2-methylbenzenesulfonamide;

N-(3-{[(5-{[(3-chloro-2-methylphenyl)sulfonyl]amino}-1,2,4-thiadiazol-3-yl)methyl]thio}phenyl)acetamide;

3-chloro-2-methyl-N-(3-{[(4-methylpyrimidin-2-yl)thio]methyl}-1,2,4-thiadiazol-5-yl)benzenesulfonamide;

(R)-3-chloro-2-methyl-N-(3-{1-[(4-methylpyrimidin-2-yl)thio]ethyl}-1,2,4-thiadiazol-5-yl)benzenesulfonamide;

(R)-2-(5-{[(3-chloro-2-methylphenyl)sulfonyl]amino}-1,2,4-thiadiazol-3-yl)-1-methylethyl 3-chloro-2-methylbenzenesulfonate;

3-chloro-2-methyl-N-{3-[(3-oxopiperazin-1-yl)carbonyl]-1,2,4-thiadiazol-5-yl}benzenesulfonamide;

3-chloro-N-(3-{[(3,4-dimethoxyphenyl)thio]methyl}-1,2,4-thiadiazol-5-yl)-2-methylbenzenesulfonamide;

(R)-3-chloro-2-methyl-N-{3-[1-(phenylsulfonyl)ethyl]-1,2,4-thiadiazol-5-yl}benzenesulfonamide;

3-chloro-N-(3-{[(2-methoxyphenyl)thio]methyl}-1,2,4-thiadiazol-5-yl)-2-methylbenzenesulfonamide;

(R)-3-chloro-2-methyl-N-{3-[1-(pyridin-3-yloxy)ethyl]-1,2,4-thiadiazol-5-yl}benzenesulfonamide;

(R)-3-chloro-2-methyl-N-{3-[1-(pyridin-4-ylthio)ethyl]-1,2,4-thiadiazol-5-yl}benzenesulfonamide;

3-chloro-2-methyl-N-(3-{[(1-methyl-1H-imidazol-2-yl)thio]methyl}-1,2,4-thiadiazol-5-yl)benzenesulfonamide;

3-chloro-2-methyl-N-{3-[(pyridin-4-ylthio)methyl]-1,2,4-thiadiazol-5-yl}benzenesulfonamide;

(R)-3-chloro-N-(3-{1-[(2-methoxyphenyl)thio]ethyl}-1,2,4-thiadiazol-5-yl)-2-methylbenzenesulfonamide;

N-(2-{[(5-{[(3-chloro-2-methylphenyl)sulfonyl]amino}-1,2,4-thiadiazol-3-yl)methyl]thio}phenyl)acetamide;

3-chloro-2-methyl-N-{3-[(pyridin-2-ylthio)methyl]-1,2,4-thiadiazol-5-yl}benzenesulfonamide;

(R)-3-chloro-N-(3-{2-[(3-fluorophenyl)thio]propyl}-1,2,4-thiadiazol-5-yl)-2-methylbenzenesulfonamide;

N-(3-tert-butyl-1,2,4-thiadiazol-5-yl)-3-chloro-2-methylbenzenesulfonamide;

(R)-3-chloro-N-{3-[1-(2,3-difluorophenoxy)ethyl]-1,2,4-thiadiazol-5-yl}-2-methylbenzenesulfonamide;

5-{[(3-chloro-2-methylphenyl)sulfonyl]amino}-N,N-diethyl-1,2,4-thiadiazole-3-carboxamide;

3-chloro-N-(3-{[(3-methoxyphenyl)thio]methyl}-1,2,4-thiadiazol-5-yl)-2-methylbenzenesulfonamide;

(R)-3-chloro-N-(3-{1-[(3-methoxyphenyl)thio]ethyl}-1,2,4-thiadiazol-5-yl)-2-methylbenzenesulfonamide;

3-chloro-N-(3-isopropyl-1,2,4-thiadiazol-5-yl)-2-methylbenzenesulfonamide;

3-chloro-2-methyl-N-{3-[(phenylthio)methyl]-1,2,4-thiadiazol-5-yl}benzenesulfonamide;

(R)-3-chloro-2-methyl-N-[3-(1-phenoxyethyl)-1,2,4-thiadiazol-5-yl]benzenesulfonamide;

(R)-3-chloro-2-methyl-N-(3-{1-[(1-methyl-1H-imidazol-2-yl)thio]ethyl}-1,2,4-thiadiazol-5-yl)benzenesulfonamide;

(R)-3-chloro-2-methyl-N-[3-(1-{[3-(trifluoromethyl)phenyl]thio}ethyl)-1,2,4-thiadiazol-5-yl]benzenesulfonamide;
(R)-3-chloro-N-{3-[1 -(3-fluorophenoxy)ethyl]-1,2,4-thiadiazol-5-yl}-2-methylbenzenesulfonamide;
(R)-3-chloro-N-{3-[1-(3,5-difluorophenoxy)ethyl]-1,2,4-thiadiazol-5-yl}-2-methylbenzenesulfonamide;
3-chloro-N-(3-{[(3-fluorophenyl)thio]methyl}-1,2,4-thiadiazol-5-yl)-2-methylbenzenesulfonamide;
3-chloro-N-(3-isobutyl-1,2,4-thiadiazol-5-yl)-2-methylbenzenesulfonamide;
3-chloro-N-(3-{[(2,4-difluorophenyl)thio]methyl}-1,2,4-thiadiazol-5-yl)-2-methylbenzenesulfonamide;
(R)-3-chloro-N-(3-{1-[(3-fluorophenyl)thio]ethyl}-1,2,4-thiadiazol-5-yl)-2-methylbenzenesulfonamide;
(R)-3-chloro-2-methyl-N-{3-[1-(phenylthio)ethyl]-1,2,4-thiadiazol-5-yl}benzenesulfonamide;
3-chloro-N-(3-{[(3,4-difluorophenyl)thio]methyl}-1,2,4-thiadiazol-5-yl)-2-methylbenzenesulfonamide;
3-chloro-2-methyl-N-{3-[2-(4-methylpiperazin-1-yl)ethyl]-1,2,4-thiadiazol-5-yl}benzenesulfonamide;
N-(4-{[(5-{[(3-chloro-2-methylphenyl)sulfonyl]amino}-1,2,4-thiadiazol-3-yl)methyl]sulfonyl}phenyl)acetamide;
3-chloro-N- {3-[(diethylamino)methyl]-1,2,4-thiadiazol-5-yl}-2-methylbenzenesulfonamide trifluoroacetate;
5-{[(3-chloro-2-methylphenyl)sulfonyl]amino}-1,3,4-thiadiazole-2-carboxylic acid;
N-[5-(4-tert-butylphenyl)-1,3,4-thiadiazol-2-yl]-3-chloro-2-methylbenzenesulfonamide;
3-chloro-2-methyl-N-[5-(2-methylpyridin-3-yl)-1,3,4-thiadiazol-2-yl]benzenesulfonamide;
3-chloro-2-methyl-N-[5-(pyridin-3-ylmethyl)-1,3,4-thiadiazol-2-yl]benzenesulfonamide;
3-chloro-2-methyl-N-{5-[(4-nitrophenoxy)methyl]-1,3,4-thiadiazol-2-yl}benzenesulfonamide;
3-chloro-2-methyl-N-[5-(trifluoromethyl)-1,3,4-thiadiazol-2-yl]benzenesulfonamide;
3-chloro-N-(5-ethyl-1,3,4-thiadiazol-2-yl)-2-methylbenzenesulfonamide;
Ethyl [(5-{[(3-chloro-2-methylphenyl)sulfonyl]amino}-1,3,4-thiadiazol-2-yl)thio]acetate;
3-chloro-N-(5-isopropyl-1,3,4-thiadiazol-2-yl)-2-methylbenzenesulfonamide;
3-chloro-N-{5-[(4-fluorophenoxy)methyl]-1,3,4-thiadiazol-2-yl}-2-methylbenzenesulfonamide;
3-chloro-N-{5-[(4-chlorophenoxy)methyl]-1,3,4-thiadiazol-2-yl}-2-methylbenzenesulfonamide;
N-(5-tert-butyl-1,3,4-thiadiazol-2-yl)-3-chloro-2-methylbenzenesulfonamide;
N-{5-[(2-allylphenoxy)methyl]-1,3,4-thiadiazol-2-yl}-3-chloro-2-methylbenzenesulfonamide;
(R)-3-chloro-2-methyl-N-[5-(1-phenoxypropyl)-1,3,4-thiadiazol-2-yl]benzenesulfonamide;
3-chloro-2-methyl-N-[5-({[2-(4-methylphenoxy)ethyl]thio}methyl)-1,3,4-thiadiazol-2-yl]benzenesulfonamide;
(R)-3-chloro-2-methyl-N-[5-(1-phenylethyl)-1,3,4-thiadiazol-2-yl]benzenesulfonamide;
3-chloro-N-[5-(ethylthio)-1,3,4-thiadiazol-2-yl]-2-methylbenzenesulfonamide;
3-chloro-N-{5-[(2-fluorophenoxy)methyl]-1,3,4-thiadiazol-2-yl}-2-methylbenzenesulfonamide;
(R)-3-chloro-2-methyl-N-[5-(1-phenylpropyl)-1,3,4-thiadiazol-2-yl]benzenesulfonamide;
3-chloro-2-methyl-N-{5-[(phenylthio)methyl]-1,3,4-thiadiazol-2-yl}benzenesulfonamide;
3-chloro-N-(5-{[(4-fluorobenzyl)thio]methyl}-1,3,4-thiadiazol-2-yl)-2-methylbenzenesulfonamide;
N-{5-[(benzylthio)methyl]-1,3,4-thiadiazol-2-yl}-3-chloro-2-methylbenzenesulfonamide.

12. The method according to any one of claims 1 to 7, wherein T is 4-phenoxyphenyl;
with the proviso that when $R^1$ is hydrogen and $A_1$ is a nitrogen atom and $A_2$ is C—Z, X is $CH_2$, Y is GO, $R^2$ is $NR^3R^4$, $R^3$ and $R^4$ represent together morpholin-4-yl, then T is not 4-phenoxyphenyl.

13. The method according to any one of claims 1 to 7, wherein the compound is selected from the group consisting of
(R)-N-(4-{[1-(5-{[(4-phenoxyphenyl)sulfonyl]amino}-1,2,4-thiadiazol-3-yl)ethyl]thio}phenyl)acetamide;
N-(3-morpholin-4-yl-1,2,4-thiadiazol-5-yl)-4-phenoxybenzenesulfonamide;
N-[3-(3-furyl)-1,2,4-thiadiazol-5-yl]-4-phenoxybenzenesulfonamide;
4-phenoxy-N-[3-(3-thienyl)-1,2,4-thiadiazol-5-yl]benzenesulfonamide;
N,N-diethyl-2-(5-{[(4-phenoxyphenyl)sulfonyl]amino}-1,2,4-thiadiazol-3-yl)acetamide;
4-phenoxy-N-[3-(2-thienyl)-1,2,4-thiadiazol-5-yl]benzenesulfonamide;
N-[3-(morpholin-4-ylcarbonyl)-1,2,4-thiadiazol-5-yl]-4-phenoxybenzenesulfonamide;
N-(3-methyl-1,2,4-thiadiazol-5-yl)-4-phenoxybenzenesulfonamide;
N-(3-methoxy-1,2,4-thiadiazol-5-yl)-4-phenoxybenzenesulfonamide;
N-(3-tert-butyl-1,2,4-thiadiazol-5-yl)-4-phenoxybenzenesulfonamide;
N-(3 -ethyl-1,2,4-thiadiazol-5-yl)-4-phenoxybenzenesulfonamide;
N-(3 -isopropyl-1,2,4-thiadiazol-5-yl)-4-phenoxybenzenesulfonamide;
N,N-diethyl-5-{[(4-phenoxyphenyl)sulfonyl]amino}-1,2,4-thiadiazole-3-carboxamide;
4-phenoxy-N-{3-[(phenylthio)methyl]-1,2,4-thiadiazol-5-yl}benzenesulfonamide;
N-(3-cyclopropyl-1,2,4-thiadiazol-5-yl)-4-phenoxybenzenesulfonamide;
N-{3-[(diethylamino)methyl]-1,2,4-thiadiazol-5-yl}-4-phenoxybenzenesulfonamide trifluoroacetate;
N-[3-(2-ethoxyethyl)-1,2,4-thiadiazol-5-yl]-4-phenoxybenzenesulfonamide;
N-[3-(morpholin-4-ylmethyl)-1,2,4-thiadiazol-5-yl]-4-phenoxybenzenesulfonamide trifluoroacetate;
4-phenoxy-N-(5-phenyl-1,3,4-thiadiazol-2-yl)benzenesulfonamide;
N-(5-isopropyl-1,3,4-thiadiazol-2-yl)-4-phenoxybenzenesulfonamide.

14. The method according to any one of claims 1 to 7, wherein
T is selected from the group consisting of 4-[(1,3-benzothiazol-2-ylthio)acetylamino]phenyl, 1,1'-biphenyl-4-yl, 4-bromo-2-methylphenyl, 4-bromophenyl, 4-n-butoxyphenyl, 4-[(5-chloro-2-hydroxybenzyl)amino]phenyl, 4-chlorophenyl, 3,4-dichlorophenyl, 2,4-dichloro-6-methylphenyl, 4-fluorophenyl, 4-methylphenyl, 4-[(4-methylphthalazin-1-yl)amino]phenyl, 2-naphthyl, 4-nitrophenyl, 2,4,6-trichlorophenyl, 4-(trifluoromethoxy)phenyl, and 2,4,6-trimethylphenyl;

with the proviso that when $R^1$ is hydrogen and $A_1$ is C—Z and $A_2$ is a nitrogen atom, Z is phenyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ are ethyl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 1,1'-biphenyl-4-yl;

$A_1$ is a nitrogen atom and $A_2$ is C—Z, Z is phenyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ are both ethyl, then T is not 1,1'-biphenyl-4-yl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 1,1'-biphenyl-4-yl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 4-bromo-2-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 4-bromo-2-methylphenyl;

$A_1$ is C—Z and $A_2$ is a nitrogen atom, Z is phenyl, then T is not 2,4-dichloro-6-methylphenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4-dichloro-6-methylphenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, Z is phenyl, then T is not 2,4-dichloro-6-methylphenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 2,4-dichloro-6-methylphenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4-dichloro-6-methylphenyl;

$A_1$ is C—Z and $A_2$ is a nitrogen atom, Z is phenyl, then T is not 2,4,6-trichlorophenyl;

$A_1$ is C—Z and $A_2$ is a nitrogen atom, X is $CH_2$, Y is CO, $R^2$ is $NR^3R^4$, $R^3$ is ethyl and $R^4$ is methyl, then T is not 2,4,6-trichlorophenyl;

$A_1$ is C—Z and $A_2$ is a nitrogen atom, X is $CH_2$, Y is CO, $R^2$ is $NR^3R^4$, $R^3$ and $R^4$ are both ethyl, then T is not 2,4,6-trichlorophenyl;

$A_1$ is C—Z and $A_2$ is a nitrogen atom, X is $CH_2$, Y is $CH_2$, $R^2$ is $NR^3R^4$, $R^3$ and $R^4$ represent together morpholin-4-yl, then T is not 2,4,6-trichlorophenyl;

$A_1$ is C—Z and $A_2$ is a nitrogen atom, X is $CH_2$, Y is CO, $R^2$ is $NR^3R^4$, $R^3$ and $R^4$ represent together morpholin-4-yl, then T is not 2,4,6-trichlorophenyl;

$A_1$ is a nitrogen atom and $A_2$ is C—Z, Z is phenyl, then T is not 2,4,6-trichlorophenyl;

$A_1$ is a nitrogen atom and $A_2$ is C—Z, X is $CH_2$, Y is CO, $R^2$ is $NR^3R^4$, $R^3$ is ethyl and $R^4$ is methyl, then T is not 2,4,6-trichlorophenyl;

$A_1$ is a nitrogen atom and $A_2$ is C—Z, X is $CH_2$, Y is CO, $R^2$ is $NR^3R^4$, $R^3$ and $R^4$ are both ethyl, then T is not 2,4,6-trichlorophenyl;

$A_1$ is a nitrogen atom and $A_2$ is C—Z, X is $CH_2$, Y is $CH_2$, $R^2$ is $NR^3R^4$, $R^3$ and $R^4$ represent together morpholin-4-yl, then T is not 2,4,6-trichlorophenyl;

$A_1$ is a nitrogen atom and $A_2$ is C—Z, X is $CH_2$, Y is CO, $R^2$ is $NR^3R^4$, $R^3$ and $R^4$ represent together morpholin-4-yl, then T is not 2,4,6-trichlorophenyl.

15. The method according to any one of claims 1 to 7, wherein the compound is selected from the group consisting of:

4-nitro-N-(3-phenyl-1,2,4-thiadiazol-5-yl)benzenesulfonamide;

N-(3-methoxy-1,2,4-thiadiazol-5-yl)-4-methylbenzenesulfonamide;

Ethyl 5-{[(4-bromo-2-methylphenyl)sulfonyl]amino}-1,2,4-thiadiazole-3-carboxylate;

4-chloro-N-(3-phenyl-1,2,4-thiadiazol-5-yl)benzenesulfonamide;

4-fluoro-N-(3-isopropyl-1,2,4-thiadiazol-5-yl)benzenesulfonamide;

4-methyl-N-[3-(morpholin-4-ylcarbonyl)-1,2,4-thiadiazol-5-yl]benzenesulfonamide;

N-[3-(3-furyl)-1,2,4-thiadiazol-5-yl]naphthalene-2-sulfonamide;

(R)-N-{4-[(1-{5-[(biphenyl-4-ylsulfonyl)amino]-1,2,4-thiadiazol-3-yl}ethyl)thio]phenyl}acetamide;

2,4,6-trichloro-N-(3-morpholin-4-yl-1,2,4-thiadiazol-5-yl)benzenesulfonamide;

N-(3-isopropyl-1,2,4-thiadiazol-5-yl)-4-methylbenzenesulfonamide;

N-(3-isopropyl-1,2,4-thiadiazol-5-yl)-4-nitrobenzenesulfonamide;

N-[3-(3-thienyl)-1,2,4-thiadiazol-5-yl]biphenyl-4-sulfonamide;

N-[3-(3-furyl)-1,2,4-thiadiazol-5-yl]biphenyl-4-sulfonamide;

4-methyl-N-[3-(trichloromethyl)-1,2,4-thiadiazol-5-yl]benzenesulfonamide;

N-(3-isopropyl-1,2,4-thiadiazol-5-yl)-2,4,6-trimethylbenzenesulfonamide;

4-bromo-N-(3-cyclopropyl-1,2,4-thiadiazol-5-yl)benzenesulfonamide;

4-methyl-N-{3-[(phenylthio)methyl]-1,2,4-thiadiazol-5-yl}benzenesulfonamide;

4-bromo-N-(3-tert-butyl-1,2,4-thiadiazol-5-yl)benzenesulfonamide;

N-(3-cyclopropyl-1,2,4-thiadiazol-5-yl)naphthalene-2-sulfonamide;

4-bromo-N-{3-[(phenylthio)methyl]-1,2,4-thiadiazol-5-yl}benzenesulfonamide;

N-(3-isopropyl-1,2,4-thiadiazol-5-yl)naphthalene-2-sulfonamide;

4-bromo-N-[3-(trichloromethyl)-1,2,4-thiadiazol-5-yl]benzenesulfonamide;

N-(3-tert-butyl-1,2,4-thiadiazol-5-yl)naphthalene-2-sulfonamide;
4-butoxy-N-(3-isopropyl-1,2,4-thiadiazol-5-yl)benzenesulfonamide;
(R)-N-(3-{1-[(3-fluorophenyl)thio]ethyl}-1,2,4-thiadiazol-5-yl)biphenyl-4-sulfonamide;
N-(3-tert-butyl-1,2,4-thiadiazol-5-yl)biphenyl-4-sulfonamide;
2,4-dichloro-N-(3-isopropyl-1,2,4-thiadiazol-5-yl)-6-methylbenzenesulfonamide;
2,4,6-trichloro-N-(3-isopropyl-1,2,4-thiadiazol-5-yl)benzenesulfonamide;
N-[3-(3-furyl)-1,2,4-thiadiazol-5-yl]-4-methylbenzenesulfonamide;
4-methyl-N-[3-(3-thienyl)-1,2,4-thiadiazol-5-yl]benzenesulfonamide;
4-fluoro-N-(3-phenyl-1,2,4-thiadiazol-5-yl)benzenesulfonamide;
N-(5-isopropyl-1,3,4-thiadiazol-2-yl)-4-nitrobenzenesulfonamide;
N-(5-isopropyl-1,3,4-thiadiazol-2-yl)-N-methylbiphenyl-4-sulfonamide;
N-(5-phenyl-1,3,4-thiadiazol-2-yl)naphthalene-2-sulfonamide;
4-bromo-N-[5-(4-methoxybenzyl)-1,3,4-thiadiazol-2-yl]benzenesulfonamide;
N-(5-isopropyl-1,3,4-thiadiazol-2-yl)naphthalene-2-sulfonamide;
4-bromo-N-(5-tert-butyl-1,3,4-thiadiazol-2-yl)benzenesulfonamide;
4-bromo-N-[5-(4-chlorobenzyl)-1,3,4-thiadiazol-2-yl]benzenesulfonamide;
N-(5-tert-butyl-1,3,4-thiadiazol-2-yl)naphthalene-2-sulfonamide;
N-[5-(2,2-dimethylpropyl)-1,3,4-thiadiazol-2-yl]-4-fluorobenzenesulfonamide;
N-(5-isopropyl-1,3,4-thiadiazol-2-yl)biphenyl-4-sulfonamide;
4-bromo-N-[5-(2,2-dimethylpropyl)-1,3,4-thiadiazol-2-yl]benzenesulfonamide;
N-[5-(methoxymethyl)-1,3,4-thiadiazol-2-yl]-4-nitrobenzenesulfonamide;
4-fluoro-N-(5-isopropyl-1,3,4-thiadiazol-2-yl)benzenesulfonamide;
4-methyl-N-(3-methyl-1,2,4-thiadiazol-5-yl)benzenesulfonamide;
N-(5-ethyl-1,3,4-thiadiazol-2-yl)-4-(trifluoromethoxy)benzenesulfonamide;
4-chloro-N-(5-isopropyl-1,3,4-thiadiazol-2-yl)benzenesulfonamide;
4-fluoro-N-[5-(trifluoromethyl)-1,3,4-thiadiazol-2-yl]benzenesulfonamide;
4-bromo-N-[5-(methoxymethyl)-1,3,4-thiadiazol-2-yl]benzenesulfonamide;
2-(1,3-benzothiazol-2-ylthio)-N-(4-{[(5-ethyl-1,3,4-thiadiazol-2-yl)amino]sulfonyl}phenyl)acetamide;
N-(5-methyl-1,3,4-thiadiazol-2-yl)-4-(trifluoromethoxy)benzenesulfonamide;
4-methyl-N-[5-(trifluoromethyl)-1,3,4-thiadiazol-2-yl]benzenesulfonamide;
4-chloro-N-[5-(trifluoromethyl)-1,3,4-thiadiazol-2-yl]benzenesulfonamide;
4-bromo-N-(5-phenyl-1,3,4-thiadiazol-2-yl)benzenesulfonamide;
4-bromo-N-(5-isopropyl-1,3,4-thiadiazol-2-yl)benzenesulfonamide;
N-[5-(4-methoxybenzyl)-1,3,4-thiadiazol-2-yl]-4-nitrobenzenesulfonamide;
3,4-dichloro-N-[5-(trifluoromethyl)-1,3,4-thiadiazol-2-yl]benzenesulfonamide;
4-fluoro-N-(5-isobutyl-1,3,4-thiadiazol-2-yl)benzenesulfonamide;
3,4-dichloro-N-(5-cyclopropyl-1,3,4-thiadiazol-2-yl)benzenesulfonamide;
4-bromo-N-[5-(trifluoromethyl)-1,3,4-thiadiazol-2-yl]benzenesulfonamide;
N-(5-cyclohexyl-1,3,4-thiadiazol-2-yl)-4-nitrobenzenesulfonamide;
N-(5-isobutyl-1,3,4-thiadiazol-2-yl)-4-methylbenzenesulfonamide;
N-(5-isobutyl-1,3,4-thiadiazol-2-yl)-4-nitrobenzenesulfonamide;
4-[(5-chloro-2-hydroxybenzyl)amino]-N-(5-ethyl-1,3,4-thiadiazol-2-yl)benzenesulfonamide;
4-chloro-N-[5-(4-chlorobenzyl)-1,3,4-thiadiazol-2-yl]benzenesulfonamide;
N-(5-cyclohexyl-1,3,4-thiadiazol-2-yl)-4-methylbenzenesulfonamide;
N-[5-(4-chlorobenzyl)-1,3,4-thiadiazol-2-yl]-4-nitrobenzenesulfonamide;
N-[5-(ethylthio)-1,3,4-thiadiazol-2-yl]-4-methylbenzenesulfonamide;
4-bromo-N-[5-(ethylthio)-1,3,4-thiadiazol-2-yl]benzenesulfonamide;
N-(5-cyclohexyl-1,3,4-thiadiazol-2-yl)-4-fluorobenzenesulfonamide;
4-chloro-N-(5-isobutyl-1,3,4-thiadiazol-2-yl)benzenesulfonamide;
N-(5-cyclohexyl-1,3,4-thiadiazol-2-yl)-2,4,6-trimethylbenzenesulfonamide;
4-chloro-N-(5-cyclohexyl-1,3,4-thiadiazol-2-yl)benzenesulfonamide;
N-[5-(2,2-dimethylpropyl)-1,3,4-thiadiazol-2-yl]-4-nitrobenzenesulfonamide;
N-1,3-benzodioxol-5-yl-2-[(5-{[(4-methylphenyl)sulfonyl]amino}-1,3,4-thiadiazol-2-yl)thio]acetamide;
N-(5-ethyl-1,3,4-thiadiazol-2-yl)-4-[(4-methylphthalazin-1-yl)amino]benzenesulfonamide; and
N-(5-isopropyl-1,3,4-thiadiazol-2-yl)-4-methylbenzenesulfonamide.

16. A method for promoting wound healing or for the treatment of a disease or disorder selected from type-2 diabetes, obesity, glaucoma, hyperlipidemia, hyperglycemia, hypertension, osteoporosis and depression, said method comprising administering to a mammal, including a human, in need of such treatment an effective amount of a compound of formula (I):

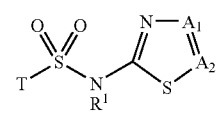

wherein
$A_1$ and $A_2$ are a nitrogen atom or C—Z, provided that $A_1$ and $A_2$ have different meanings, wherein, when $A_2$ is nitrogen and $A_1$ is C—Z, then
Z is:
methoxy;
—C(O)-piperidinyl-$(R^B)_n$;

—CH($R^A$)-phenyl-($R^B$)$_n$;
—CH($R^A$)—C(O)—N$R_2^A$;
—(CH$_2$)$_m$—CH($R^A$)-$R^D$-phenyl-($R^B$)$_n$;
—CR$_3^C$; where $R^C$ is halogen;
—(CH$_2$)$_m$—CH($R^A$)—$R^D$-heteroaryl-($R^B$)$_n$;
—C(O)N$R_2^A$;
—CH($R^A$)—(CH$_2$)$_m$—N—C$_{1-6}$ amido;
—C$_3$–C$_6$-cycloalkyl; or
morpholinyl;
where $R^A$ is independently H or C$_{1-6}$ alkyl or C$_{1-6}$ alkyl substituted with C$_{1-6}$ alkoxy;
$R^B$ is independently COOR$^A$, CH$_2$OH, N—C$_{1-6}$ amido, C$_{1-6}$ alkoxy, optionally halogenated C$_{1-6}$ alkyl, halogen, or nitro;
$R^D$ is 0, S, SO, SO$_2$ or OSO$_2$;
n is 0–4 and
m is 0–1;
where T is selected from the group consisting of:
2-acetylamino-4-methylthiazol-5-yl; benzyl; 5-bromo-6-chloropyridin-3-yl; 5-chloro-1,3-dimethyl-1H-pyrazol-4-yl; 2,3-dihydro-1,4-benzodioxin-6-yl; 2,3-dihydro-1-benzofuran-5-yl; 5-(dimethylamino)-1-naphthyl; 1,2-dimethyl-1H-imidazol-4-yl; 3,5-dimethylisoxazol-4-yl; 4-methyl-3,4-dihydro-2H-1,4-benzoxazin-7-yl; 1-methyl-1H-imidazol-4-yl; 5-methyl-2-(trifluoromethyl)3-furyl; 4-morpholin-4-ylpyridin-3-yl; 1-naphthyl; 2-naphthyl; 2,2,4,6,7-pentamethyl-2,3-dihydro-1-benzofuran-5-yl; 6-phenoxypyridin-3-yl; quinolin-8-yl; and 1,3,5-trimethyl-1H-pyrazol-4-yl;
thienyl optionally substituted with one or more of acetylamino; chloro; methyl; 2-(methylthio)pyrimidin-4-yl; nitro; phenylsulfonyl; pyridinyl;
phenyl substituted with one or more of acetyl; acetylamino; amino; 4-(1,3-benzothiazol-2-ylthio)acetylamino; benzoylamino; bromo; chloro; 3-chloro-2-cyanophenoxy; (5-chloro-2-hydroxybenzyl)amino; 4-chloro-3-nitrophenylcarbonylamino; [(4-chlorophenyl)amino]carbonylamino; cyano; 2,4-dichlorophenoxyacetylamino; fluoro; 4-{[(4-fluorophenyl)amino]carbonothioyl}amino; 4-fluorophenylcarbonylamino; hydroxy; methoxy; methyl; 5-methyl-1,3,4-oxadiazol-2-yl; (4-methylphthalazin-1-yl)amino; 1,3-oxazol-5-yl; 2-methyl-4-pyrimidyl; n-butoxy; nitro; N-phthalimido; phenoxy; phenyl; 1H-pyrazol-1-yl; tert-butyl; tetrazolyl; 2,2,2-trifluoroethoxy; trifluoromethoxy; trifluoromethyl; and
$R^1$ is hydrogen or methyl,
pharmaceutically acceptable salts, solvates, hydrates, geometrical isomers, tautomers, optical isomers, N-oxides and prodrug forms thereof.

17. A method for promoting wound healing or for the treatment of a disease or disorder selected from type-2 diabetes, obesity, glaucoma, hyperlipidemia, hyperglycemia, hypertension, osteoporosis and depression, said method comprising administering to a mammal, including a human, in need of such treatment an effective amount of a compound of formula (I):

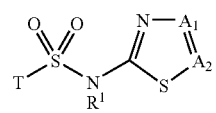

I wherein
$A_1$ and $A_2$ are a nitrogen atom or C—Z, provided that $A_1$ and $A_2$ have different meanings, wherein:

when $A_1$ is nitrogen and $A_2$ is C—Z, then
Z is:
—S—C$_{1-6}$ alkyl;
—S—CH$_2$—C(O)—O—C$_{1-6}$ alkyl;
t-butyl;
—CH$_2$—S—CH$_2$—CH$_2$—O-phenyl-4-methyl; or
—S—CH$_2$—C(O)—NH-benzodioxol-5-yl,
where T is selected from the group consisting of:
2-acetylamino-4-methylthiazol-5-yl; benzyl; 5-bromo-6-chloropyridin-3-yl; 5-chloro-1,3-dimethyl-1H-pyrazol-4-yl; 2,3-dihydro-1,4-benzodioxin-6-yl; 2,3-dihydro-1-benzofuran-5-yl; 5-(dimethylamino)-1-naphthyl; 1,2-dimethyl-1H-imidazol-4-yl; 3,5-dimethylisoxazol-4-yl; 4-methyl-3,4-dihydro-2H-1,4-benzoxazin-7-yl; 1-methyl-1H-imidazol-4-yl; 5-methyl-2-(trifluoromethyl)-3-furyl; 4-morpholin-4-ylpyridin-3-yl; 1-naphthyl; 2-naphthyl; 2,2,4,6,7-pentamethyl-2,3-dihydro-1-benzofuran-5-yl; 6-phenoxypyridin-3-yl; quinolin-8-yl; and 1,3,5-trimethyl-1H-pyrazol-4-yl;
thienyl optionally substituted with one or more of acetylamino; chloro; methyl; 2-(methylthio)pyrimidin-4-yl; nitro; phenylsulfonyl; pyridinyl;
phenyl substituted with one or more of acetyl; acetylamino; amino; 4-(1,3-benzothiazol-2-ylthio)acetylamino; benzoylamino; bromo; chloro; 3-chloro-2-cyanophenoxy; (5-chloro-2-hydroxybenzyl)amino; 4-chloro-3-nitrophenylcarbonylamino; [(4-chlorophenyl)amino]carbonylamino; cyano; 2,4-dichlorophenoxyacetylamino; fluoro; 4-{[(4-fluorophenyl)amino]carbonothioyl}amino; 4-fluorophenylcarbonylamino; hydroxy; methoxy; methyl; 5-methyl-1,3,4-oxadiazol-2-yl; (4-methylphthalazin-1-yl)amino; 1,3-oxazol-5-yl; 2-methyl-4-pyrimidyl; n-butoxy; nitro; N-phthalimido; phenoxy; phenyl; 1H-pyrazol-1-yl; tert-butyl; tetrazolyl; 2,2,2-trifluoroethoxy; trifluoromethoxy; trifluoromethyl; and
$R^1$ is hydrogen or methyl,
pharmaceutically acceptable salts, solvates, hydrates, geometrical isomers, tautomers, optical isomers, N-oxides and prodrug forms thereof.

18. A method for promoting wound healing or for the treatment of a disease or disorder selected from type-2 diabetes, obesity, glaucoma, hyperlipidemia, hyperglycemia, hypertension, osteoporosis and depression, said method comprising administering to a mammal, including a human, in need of such treatment an effective amount of a compound of formula (I):

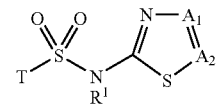

I wherein
$A_1$ and $A_2$ are a nitrogen atom or C—Z, provided that $A_1$ and $A_2$ have different meanings, wherein, when $A_1$ is nitrogen and $A_2$ is C—Z, then
T is phenyl substituted with:
4-methylphthalazinylamino;
3-nitro-4-chloro-phenyl-carbonylamino;
4-fluorophenylcarbonylamino;
4-chlorophenylurea;
4-fluorophenylthiourea;
1,3-benzothiazolylthioacetamido;

2,4-dichlorophenoxyacetamido or
5-chloro-2-hydroxy-benzylamino;

Z is [(1,3-benzodioxol-5-ylaminocarbonyl)methyl]thio; n-butylthio; (R)-2-[(3-chloro-2-methylbenzenesulfonyl)oxy]propyl; cyclohexyl; cyclopropyl; ethoxycarbonylmethylthio; ethylthio; (R)-2-[(3-fluorophenyl)thio]propyl; 3-furyl; methoxy; 2-methylpyridin-3-yl; morpholin-4-yl; (R)-1-phenoxy-n-propyl; phenyl; (R)-1-phenyl-n-propyl; tert-butyl; tert-butylphenyl; 2-thienyl; 3-thienyl; (trichloromethyl); (trifluoromethyl); $A_3$; or —CH($CH_3$)$A_3$, wherein $A_3$ is selected from methyl; carbamoyl; N-(n-butanamidyl); phenylsulfonyl; phenyl; phenoxy optionally substituted with one or more fluoro; phenylthio optionally substituted with one or more acetylamino, methoxy, trifluoromethyl, fluoro; pyridin-3-yloxy; 4-methylpyrimidin-2-ylthio; pyridin-4-ylthio; 1-methyl-1H-imidazol-2-ylthio;

or X—Y—$R^2$, wherein
X is $CH_2$ or CO;
Y is $CH_2$, CO or a single bond;
$R^2$ is selected from the group consisting of
  4-acetylaminophenylsulfonyl; N-(n-butanamidyl); 1-(3-chloro-2-methylphenylsulfonyloxyl)ethyl; 1-[(3-fluorophenyl)thio]ethyl; 4-chlorophenyl; 3-ethoxy-n-propyl, hydrogen; isopropyl; 4-methoxyphenyl; methyl; phenylsulfonyl; pyridin-3-yl; tert-butyl;
  $NR^3R^4$, wherein $R^3$ and $R^4$ are each independently selected from 3-ethoxy-n-propyl; ethyl; hydrogen; methyl;
  $NR^3R^4$ represent together 3-carbethoxypiperidin-1-yl; 4-carbethoxypiperidin-1-yl; 3-hydroxymethylpiperidin-1-yl; 3-hydroxypiperidin-1-yl; 4-methylpiperazin-1-yl; morpholin-4-yl; 3-oxopiperazin-1-yl;
  $R^5O$, wherein $R^5$ is 2-allylphenyl; 4-chlorophenyl; ethyl; 2-fluorophenyl; 4-fluorophenyl; hydrogen; methyl; 4-nitrophenyl; and
  $R^6S$, wherein $R^6$ is 2-acetylaminophenyl; 3-acetylaminophenyl; 4-acetylaminophenyl; benzyl; 2,4-difluorophenyl; 3,4-difluorophenyl; 3,4-dimethoxyphenyl; 4-fluorobenzyl; 3-fluorophenyl; 2-methoxyphenyl; 3-methoxyphenyl; 1-methyl-1H-imidazol-2-yl; 2-(4-methylphenoxy)ethyl; 4-methylpyrimidin-2-yl; phenyl; pyridin-2-yl; pyridin-4-yl;

pharmaceutically acceptable salts, solvates, hydrates, geometrical isomers, tautomers, optical isomers, N-oxides and prodrug forms thereof.

19. The method according to any one of claims 16–18, for promoting wound healing.

20. The method according to any one of claims 16–18, wherein the method is for the treatment of a disease or disorder is selected from type-2 diabetes, obesity, glaucoma, hyperlipidemia, hyperglycemia, hypertension, osteoporosis, and depression.

21. The method according to any of claims 16–18 for the treatment or prophylaxis of a medical condition involving delayed or impaired wound healing.

22. The method according to claim 21, wherein the medical condition involving delayed or impaired wound healing is diabetes.

23. The method according to claim 21, wherein the medical condition involving delayed or impaired wound healing is caused by treatment with glucocorticoids.

24. The method according to any one of claims 16–18 for the promotion of wound healing in chronic wounds, such as diabetic ulcers, venous ulcers or pressure ulcers.

\* \* \* \* \*